(12) United States Patent
Choi et al.

(10) Patent No.: US 11,208,412 B2
(45) Date of Patent: Dec. 28, 2021

(54) PYRROLO-PYRIMIDINE DERIVATIVE COMPOUND, PREPARATION METHOD THEREFOR, AND PHARMACEUTICAL COMPOSITION COMPRISING SAME COMPOUND AS EFFECTIVE INGREDIENT FOR PREVENTING OR TREATING PROTEIN KINASE-RELATED DISEASE

(71) Applicants: DAEGU-GYEONGBUK MEDICAL INNOVATION FOUNDATION, Daegu (KR); NATIONAL CANCER CENTER, Gyeonggi-do (KR); SAMSUNG LIFE PUBLIC WELFARE FOUNDATION, Seoul (KR)

(72) Inventors: Hwan Geun Choi, Seoul (KR); Jong Bae Park, Gyeonggi-do (KR); Eunhwa Ko, Daegu (KR); Jung Beom Son, Daegu (KR); Joong-heui Cho, Daegu (KR); Yi Kyung Ko, Daegu (KR); Jin-Hee Park, Jeollanam-do (KR); So Young Kim, Daegu (KR); Seock Yong Kang, Seoul (KR); Seungyeon Lee, Daegu (KR); Nam Doo Kim, Daegu (KR); Yunho Lee, Daegu (KR); Sun-Hwa Lee, Daegu (KR); Dayea Kim, Daegu (KR); Sun Joo Lee, Daegu (KR); Jae Hyun Bae, Daegu (KR); Eunmi Hong, Daegu (KR); Tae-ho Jang, Gyeongsangbuk-do (KR); Sang Bum Kim, Daegu (KR); Seung Hoon Lee, Daejeon (KR); Do-Hyun Nam, Seoul (KR)

(73) Assignees: Daegu-Gyeongbuk Medical Innovation Foundation, Daegu (KR); National Cancer Center, Gyeonggi-do (KR); Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 16/488,194

(22) PCT Filed: Feb. 22, 2018

(86) PCT No.: PCT/KR2018/002164
§ 371 (c)(1),
(2) Date: Aug. 22, 2019

(87) PCT Pub. No.: WO2018/155916
PCT Pub. Date: Aug. 30, 2018

(65) Prior Publication Data
US 2020/0239474 A1    Jul. 30, 2020

(30) Foreign Application Priority Data

Feb. 22, 2017 (KR) .................. 10-2017-0023393

(51) Int. Cl.
| | | |
|---|---|---|
| C07D 487/04 | (2006.01) |
| A61P 35/00 | (2006.01) |
| A61P 29/00 | (2006.01) |
| A61P 25/28 | (2006.01) |
| A61K 31/519 | (2006.01) |

(52) U.S. Cl.
CPC ............ *C07D 487/04* (2013.01); *A61P 25/28* (2018.01); *A61P 29/00* (2018.01); *A61P 35/00* (2018.01); *C07B 2200/07* (2013.01)

(58) Field of Classification Search
CPC .................................................. C07D 487/04
See application file for complete search history.

(56) References Cited

U.S. PATENT DOCUMENTS

2008/0004295 A1 *  1/2008  Gore .................. A61P 11/00
                                                514/265.1

FOREIGN PATENT DOCUMENTS

| CA | 2937430 A1 * | 8/2015 | ............. A61P 25/16 |
|---|---|---|---|
| KR | 10-2009-0117830 | 11/2009 | |

(Continued)

*Primary Examiner* — Susanna Moore
(74) *Attorney, Agent, or Firm* — Klarquist Sparkman, LLP

(57) ABSTRACT

The present invention relates to a novel pyrrolo-pyrimidine derivative compound, a preparation method therefor, and a pharmaceutical composition comprising the same compound as an effective ingredient for preventing or treating a protein kinase-related disease. The compound represented by Chemical Formula 1 according to the present invention, an optical isomer thereof, or a pharmaceutically acceptable salt thereof, and a pharmaceutical composition comprising the same as an effective ingredient has outstanding inhibitory activity against LRRK2 kinase and against phosphorylation in the NIH-3T3 cell line, which is an LRRK2-expressing cell line, and NCC01 and 448T cell lines, which are both derived from patients with brain tumors. Verified to have inhibitory activity against various protein kinases in addition to LRRK2, the compound can find effective applications in the treatment or prevention of protein kinase-related diseases.

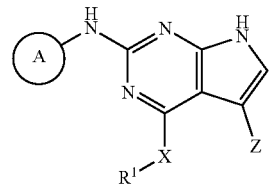

Formula 1

7 Claims, 2 Drawing Sheets

(56) References Cited

FOREIGN PATENT DOCUMENTS

| | | |
|---|---|---|
| KR | 10-2014-0059246 | 5/2014 |
| KR | 10-2016-0106622 | 9/2016 |
| KR | 10-2016-0106623 | 9/2016 |
| WO | WO 2007/042299 A1 | 4/2007 |
| WO | WO 2009/131687 A2 | 10/2009 |
| WO | WO 2015/113451 A1 | 8/2015 |

\* cited by examiner

【Figure 1】
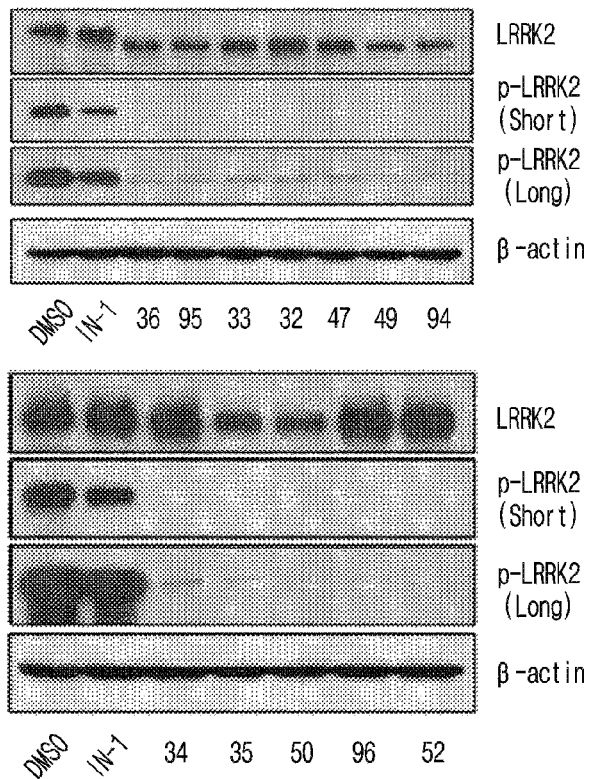
【Figure 2】
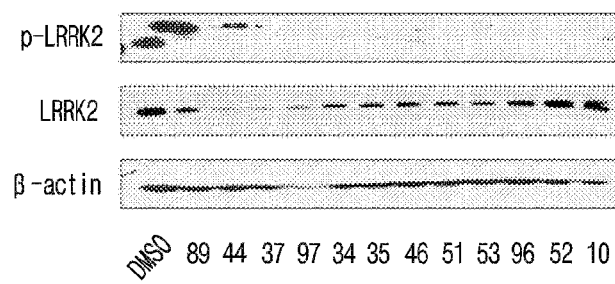

[Figure 3]
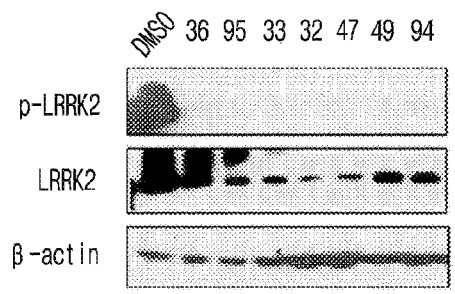

PYRROLO-PYRIMIDINE DERIVATIVE COMPOUND, PREPARATION METHOD THEREFOR, AND PHARMACEUTICAL COMPOSITION COMPRISING SAME COMPOUND AS EFFECTIVE INGREDIENT FOR PREVENTING OR TREATING PROTEIN KINASE-RELATED DISEASE

CROSS REFERENCE TO RELATED APPLICATIONS

This is the § 371 U.S. National Stage of International Application No. PCT/KR2018/002164, filed Feb. 22, 2018, which in turn claims the benefit of Korean Patent Application No. 10-2017-0023393, filed Feb. 22, 2017, which is incorporated by reference herein in its entirety.

BACKGROUND OF THE INVENTION

1. Field of the Invention

The present invention relates to a pyrrolo-pyrimidine derivative compound, a preparation method therefor, and a pharmaceutical composition comprising the same compound as an effective ingredient for preventing or treating a protein kinase-related disease.

2. Description of the Related Art

Protein kinase is an enzyme that catalyses the reaction to transfer the terminal phosphate group of adenosine triphosphate (ATP) to a specific residue of protein (tyrosine, serine, threonine), and is involved in signals that regulate cell activation, growth, and differentiation according to extracellular mediators and environmental changes.

Inappropriately high protein kinase activity is directly or indirectly involved in various diseases resulting from abnormal cellular functions. For example, mutation, over-expression or failure of appropriate regulatory mechanism of kinases involved in inappropriate enzyme activity, or over-synthesis or deficiency of factors involved in upstream or downstream signal transduction of cytokines or kinases can cause disease. Therefore, selective inhibition of kinase activity can be a beneficial target for the development of new drugs for the treatment of disease.

Brain cancer is a general term for primary brain cancer that occurs in the brain tissue and the cerebral meninges surrounding the brain and secondary brain cancer that has metastasized from the skull or other parts of the body. Such brain cancer is distinguished from other cancers developed in other organs in many aspects. First, cancers developed in lung, stomach and breast are limited in one or two types of cancer for each organ and their properties are the same or similar. However, many different types of cancers can be developed in the brain. For example, polymorphic glioblastoma, malignant glioma, lymphoma, blastoma, and metastatic tumor can be developed in the brain.

Parkinson's disease is the result of chronic progressive degeneration of neurons, but the cause has not been fully disclosed yet. Although the major causes are unknown, Parkinson's disease is characterized by the degeneration of dopaminergic neurons in the substantia nigra (SN). The substantia nigra is a part of the lower brain or the brainstem that helps the regulation of unconscious movement. Dopamine deficiency in the brain caused by loss of these neurons is known to cause observable symptoms. Clinically, the main symptoms of Parkinson's disease are resting tremor, rigidity, bradykinesia, and postural instability. Not only the MAO-B inhibitor selegiline and the COMT inhibitor entacapone but also levodopa, dopamine agonists (for example, rotigotine, pramipexole, bromocriptine, ropinirole, cabergoline, pergolide, apomorphine and lisuride), anticholinergic drugs, NMDA antagonists and β-blockers are used as medications for relieving symptoms relating to motion. Most of these drugs are involved in dopamine and/or choline signal transduction, by which they affect typical motion dysfunction symptoms of Parkinson's disease (Patent Reference 1: Korean Patent Publication No. 10-2009-0117830).

LRRK2 (leucine-rich repeat kinase-2) is a protein belonging to leucine-rich repeat kinase family, which is composed of 2527 amino acids with high interspecies similarity. Characteristically, it contains both GTPase activity and serine-threonine kinase activity in one protein. The expressed LRRK2 is observed in various organs and tissues including the brain, and is known to exist in cytoplasm or cell membrane and mitochondrial outer membrane at the cellular level. Currently, studies on in vivo functions of LRRK2 are actively under-going. LRRK2 has 5 functionally important domains which are involved in self-active regulation by autophosphorylation and cell function regulation by protein interaction and enzymatic action. Particularly, it is known that chaperone machinery, cytoskeleton arrangement, protein translational machinery, synaptic vesicle endocytosis, mitogen-activated protein kinases signaling cascades and ubiquitin/autophageprotein degradation pathways are regulated by LRRK2.

Parkinson's disease occurs sporadically in most cases, but 5-10% of the patients have family history. From the studies with the samples of these patients, the locations of PARK 1-16 genes were identified, among which a few locations have been confirmed to have mutations to cause Parkinson's disease. The known causing genes of Parkinson's disease that cause Parkinson's disease by mutation are parkin, PINK1, DN-1, α-synuclein and LRRK2 (leucine-rich repeat kinase 2), etc. Among them, the said LRRK2 gene was first reported in 2004 as a dominant gene of a homologous chromosome like α-synuclein. Patients with Parkinson's disease caused by LRRK2 mutation display very similar symptoms to patients with sporadic Parkinson's disease, unlike patients with Parkinson's disease caused by mutations of other genes. LRRK2 mutation is observed not only in those Parkinson's disease patients who have family history but also in 1-2% of sporadic Parkinson's disease patients. Thus, identification of the pathogenesis of Parkinson's disease by mutation of this gene would be very helpful in understanding the pathogenesis of Parkinson's disease and in the development of therapeutic agents.

LRRK2 is known to be involved in mild cognitive impairment associated with Alzheimer's disease, L-Dopa induced dyskinesia, CNS disorder associated with neuronal progenitor differentiation, cancer such as brain cancer, kidney cancer, breast cancer, prostate cancer, blood cancer, lung cancer and acute myelogenous leukemia, papillary kidney and thyroid carcinoma, multiple myeloma, amyotrophic lateral sclerosis, rheumatoid arthritis and ankylosing spondylitis. Therefore, a compound or a composition that is effective in regulating LRRK2 activity can provide therapeutic effects on neurodegenerative disease, CNS disorder, cancer, acute myelogenous leukemia and multiple myeloma, and inflammatory disease.

In the course of our study on a compound capable of inhibiting the activation of protein kinases, the present inventors found that a pyrrolo-pyrimidine derivative compound was not only able to inhibit the expressions of LRRK2 and various protein kinases significantly but also able to inhibit those cell lines expressing brain cancer and Parkinson's disease, leading to the completion of the present invention.

SUMMARY OF THE INVENTION

It is an object of the present invention to provide a pyrrolo-pyrimidine derivative compound and a preparation method thereof.

It is another object of the present invention to provide a preparation method of the pyrrolo-pyrimidine derivative compound.

It is also an object of the present invention to provide a pharmaceutical composition for the prevention or treatment of protein kinase related disease.

It is further an object of the present invention to provide a health functional food composition for the prevention or amelioration of protein kinase related disease.

To achieve the above objects, the present invention provides a compound represented by formula 1 below, an optical isomer thereof or a pharmaceutically acceptable salt thereof:

[Formula 1]

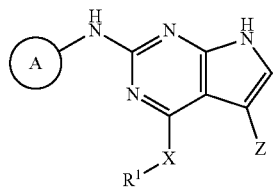

(In formula 1,

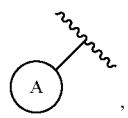

Z, X and $R^1$ are as defined in this specification.)

The present invention also provides a preparation method of the compound represented by formula 1 comprising the following steps, as shown in reaction formula 1 below:

preparing a compound represented by formula 4 by reacting a compound represented by formula 2 with a compound represented by formula 3 (step 1); and preparing a compound represented by formula 1 by reacting the compound represented by formula 4 prepared in step 1 above in the presence of an acid (step 2):

[Reaction Formula 1]

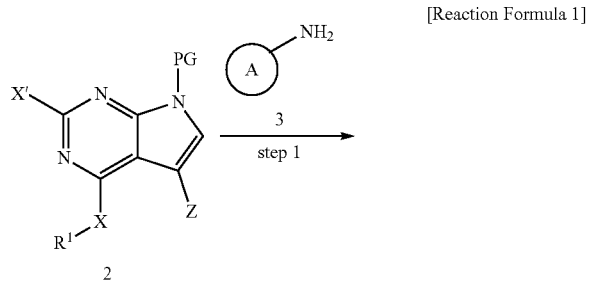

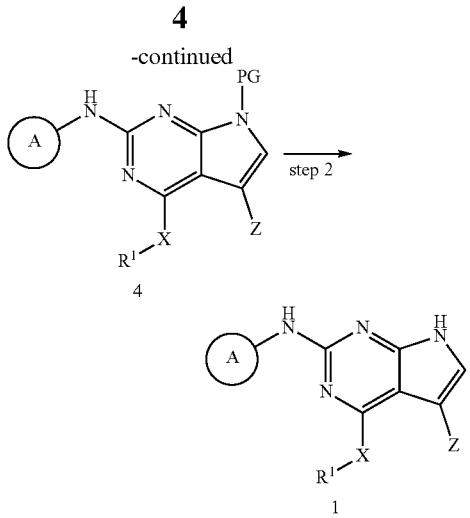

(In reaction formula 1,

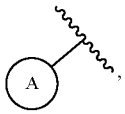

Z, X, $R^1$, X' and PG are as defined in this specification.)

The present invention also provides a pharmaceutical composition comprising a compound represented by formula 1, an optical isomer thereof or a pharmaceutically acceptable salt thereof as an active ingredient for the prevention or treatment of protein kinase related disease.

The present invention also provides a health functional food composition comprising a compound represented by formula 1, an optical isomer thereof or a pharmaceutically acceptable salt thereof as an active ingredient for the prevention or amelioration of protein kinase related disease.

The present invention also provides a method for preventing or treating protein kinase related disease, which comprises the step of administering a pharmaceutical composition or a health functional food composition comprising a compound represented by formula 1 or a pharmaceutically acceptable salt thereof as an active ingredient to a subject in need.

In addition, the present invention provides a use of the pharmaceutical composition or the health functional food composition above comprising a compound represented by formula 1 or a pharmaceutically acceptable salt thereof as an active ingredient for the prevention or treatment of protein kinase related disease.

Advantageous Effect

The compound represented by formula 1, the optical isomer thereof or the pharmaceutically acceptable salt thereof according to the present invention has an excellent activity of inhibiting various protein kinases including LRRK2, so that a pharmaceutical composition comprising the same as an active ingredient can be effectively used for the prevention or treatment of protein kinase related disease.

BRIEF DESCRIPTION OF THE DRAWINGS

FIG. 1 is a photograph illustrating the inhibition of LRRK2 phosphorylation in NIH-3T3 cell line by the compounds of the present invention.

FIG. 2 is a photograph illustrating the inhibition of LRRK2 phosphorylation in NCC01 cell line by the compounds of the present invention.

FIG. 3 is a photograph illustrating the inhibition of LRRK2 phosphorylation in 448T cell line by the compounds of the present invention.

DESCRIPTION OF THE PREFERRED EMBODIMENTS

Hereinafter, the present invention is described in detail.

The present invention provides a compound represented by formula 1 below, an optical isomer thereof or a pharmaceutically acceptable salt thereof:

[Formula 1]

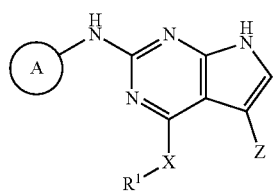

In formula 1,

X is —NH—, —O— or —S—;

Z is cyano (—CN); or straight or branched $C_1$-$C_3$ alkyl substituted with one or more halogens;

$R^1$ is straight or branched $C_1$-$C_6$ alkyl; $C_3$-$C_6$ cycloalkyl nonsubstituted or substituted with one or more straight or branched $C_1$-$C_3$ alkyls; or 3-8 membered heterocycloalkyl containing one or more heteroatoms selected from the group consisting of N and O; and

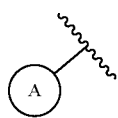

is

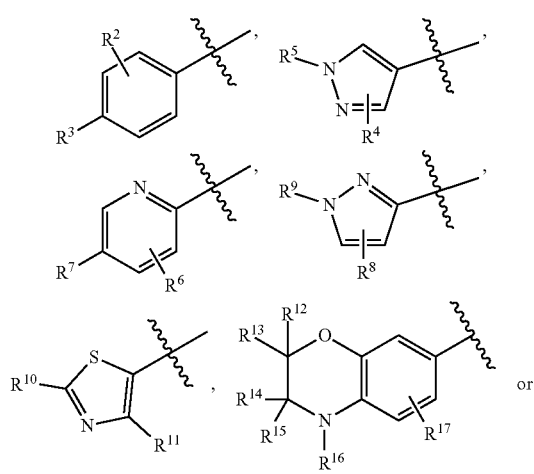

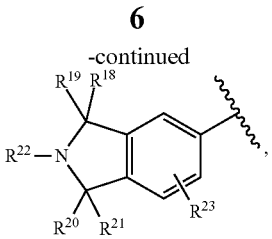

wherein, each $R^2$, $R^4$, $R^6$, $R^8$, $R^{11}$, $R^{17}$, and $R^{23}$ are independently one or more substituents selected from the group consisting of hydrogen, halogen, straight or branched $C_1$-$C_3$ alkyl and straight or branched $C_1$-$C_3$ alkoxy, $R^3$, $R^5$, $R^7$ and $R^9$ are independently straight or branched $C_1$-$C_3$ alkyl; straight or branched $C_1$-$C_3$ alkoxy; straight or branched $C_1$-$C_3$ alkyl substituted with one or more substituents selected from the group consisting of hydroxy, straight or branched $C_1$-$C_3$ alkyl, straight or branched $C_1$-$C_3$ alkoxy, aminocarboxy group (—(C=O)NH$_2$) and —CN; 3-8 membered heterocycloalkyl containing one or more heteroatoms selected from the group consisting of N and O nonsubstituted or substituted with one or more substituents selected from the group consisting of halogen and 3-5 membered heterocycloalkyl containing one or more oxygen atoms; 3-8 membered heterocycloalkyl containing one or more heteroatoms selected from the group consisting of N and O non-substituted or substituted with one or more straight or branched $C_1$-$C_3$ alkyls; or —(C=O)NR$^{24}$R$^{25}$, wherein, $R^{24}$ and $R^{25}$ are independently hydrogen; 3-8 membered heterocycloalkyl containing one or more heteroatoms selected from the group consisting of N and O substituted with straight or branched $C_1$-$C_3$ alkyl or 3-5 membered heterocycloalkyl containing one or more oxygen atoms; or $R^{24}$ and $R^{25}$ form 3-8 membered heterocycloalkyl containing one or more heteroatoms selected from the group consisting of N and O along with nitrogen atom to which they are attached, wherein, the substituted heterocycloalkyl is substituted with one or more substituents selected from the group consisting of halogen; straight or branched $C_1$-$C_3$; and 3-6 membered heterocycloalkyl containing one or more heteroatoms selected from the group consisting of N and O nonsubstituted or substituted with one or more straight or branched $C_1$-$C_3$ alkyls, $R^{10}$ is —CR$^{26}$R$^{27}$—CN, wherein $R^{26}$ and $R^{27}$ are independently hydrogen, or straight or branched $C_{1-3}$ alkyl, $R^{12}$, $R^{13}$, $R^{14}$, $R^{15}$, $R^{18}$, $R^{19}$, $R^{20}$, and $R^{21}$ are independently hydrogen, or straight or branched $C_{1-3}$ alkyl, or two of $R^{12}$, $R^{13}$, $R^{14}$, $R^{15}$, $R^{18}$, $R^{19}$, $R^{20}$, and $R^{21}$ bonded to the same carbon can form carbonyl along with the carbon to which they are attached, and $R^{16}$ and $R^{22}$ are independently hydrogen, or straight or branched $C_{1-3}$ alkyl.

In formula 1 above,

X is —NH— or —O—;

Z is —CN or methyl substituted with one or more halogens;

$R^1$ is straight or branched $C_1$-$C_3$ alkyl; $C_3$-$C_5$ cycloalkyl nonsubstituted or substituted with one or more methyls; or 5-6 membered heterocycloalkyl containing one or more heteroatoms selected from the group consisting of N and O; and

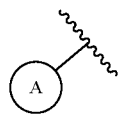

is

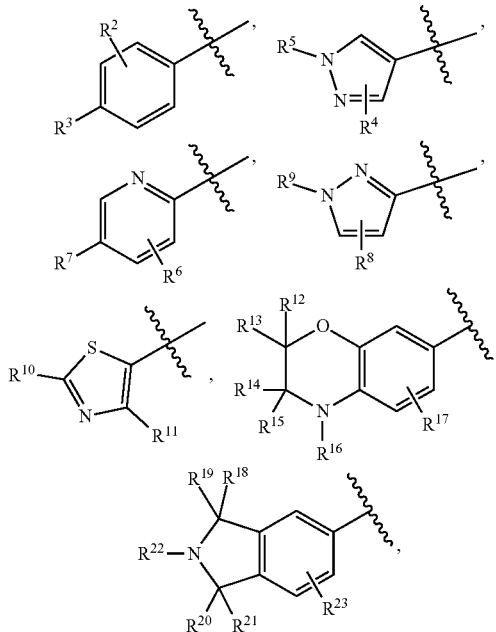

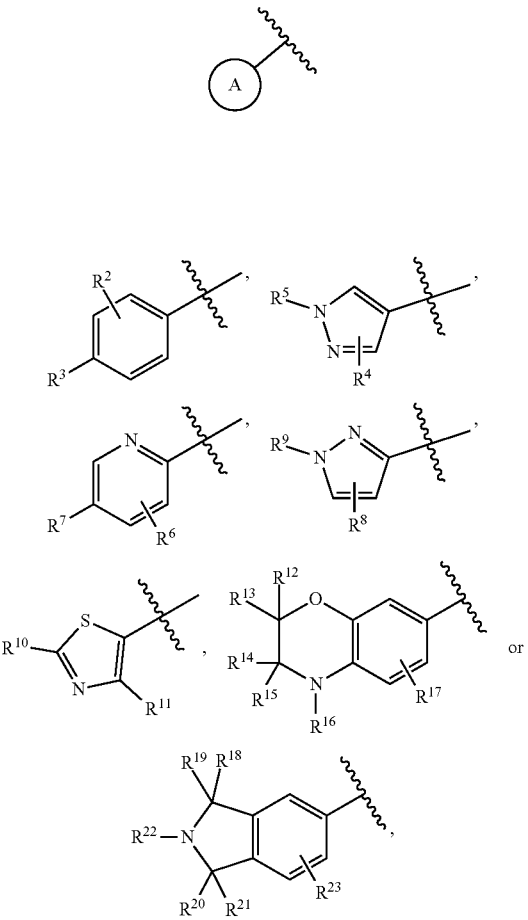

wherein, $R^2$, $R^4$, $R^6$, $R^8$, $R^{11}$, $R^{17}$, and $R^{23}$ are independently one or more substituents selected from the group consisting of hydrogen, fluoro, chloro, bromo, methyl, ethyl, methoxy and ethoxy, $R^3$, $R^5$, $R^7$ and $R^9$ are independently methyl; isopropyl; methoxy; straight or branched $C_1$-$C_3$ alkyl substituted with one or more substituents selected from the group consisting of hydroxy, methoxy, methyl, aminocarboxy group (—(C=O)NH$_2$) and —CN; piperidinyl substituted with one or more substituents selected from the group consisting of fluoro, chloro and oxetanyl; piperazinyl or morpholinyl nonsubstituted or substituted with one or more methyls; or —(C=O)NR$^{24}$R$^{25}$, wherein, $R^{24}$ and $R^{25}$ are independently hydrogen; piperidinyl substituted with methyl, isopropyl or oxetanyl; or $R^{24}$ and $R^{25}$ form nonsubstituted or substituted piperazinyl, morpholinyl or piperidinyl along with nitrogen atom to which they are attached, wherein, the substituted piperazinyl, morpholinyl or piperidinyl can be substituted with one or more substituents selected from the group consisting of fluoro, methyl, oxetanyl, piperazinyl and morpholinyl, $R^{10}$ is —CR$^{26}$R$^{27}$—CN, wherein $R^{26}$ and $R^{27}$ are independently hydrogen, methyl or ethyl, $R^{12}$, $R^{13}$, $R^{14}$, $R^{15}$, $R^{18}$, $R^{19}$, $R^{20}$, and $R^{21}$ are independently hydrogen, methyl or ethyl, or two of $R^{12}$, $R^{13}$, $R^{14}$, $R^{15}$, $R^{18}$, $R^{19}$, $R^{20}$, and $R^{21}$ bonded to the same carbon can form carbonyl along with the carbon to which they are attached, and $R^{16}$ and $R^{22}$ are independently hydrogen, methyl or ethyl.

In formula 1 above,

X is —NH— or —O—;

Z is —CN or —CF$_3$;

$R^1$ is methyl, ethyl, n-propyl, isopropyl, cyclopropyl, 1-methylcyclopropyl, tetrahydropyranyl or tetrahydrofuranyl;

wherein, $R^2$, $R^4$, $R^6$, $R^8$, $R^{11}$, $R^{17}$, and $R^{23}$ are independently one or more substituents selected from the group consisting of hydrogen, chloro, fluoro, bromo, methyl and methoxy;

$R^3$ and $R^7$ are independently methoxy,

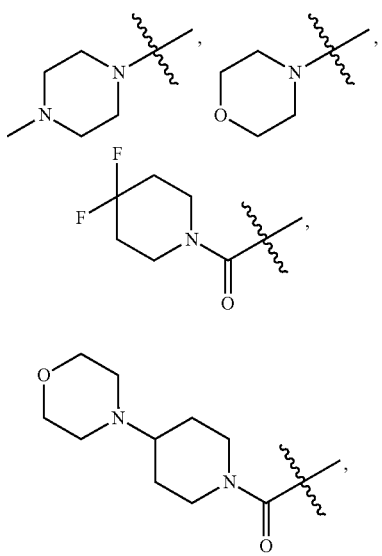

-continued

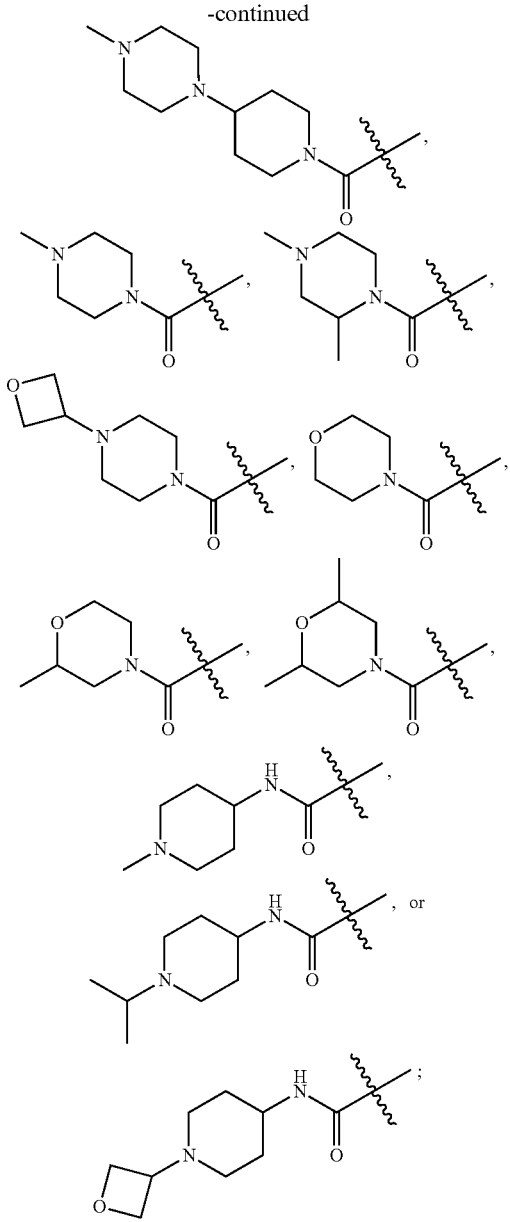

and

R⁵ and R⁹ are independently methyl, isopropyl,

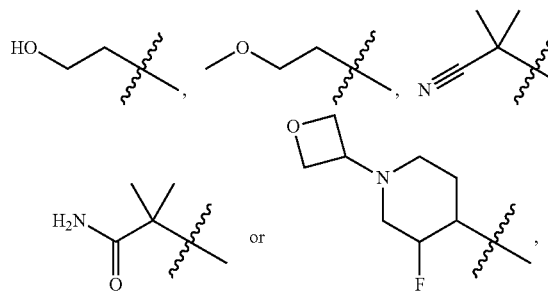

$R^{10}$ is —$CR^{26}R^{27}$—CN, wherein $R^{26}$ and $R^{27}$ are independently hydrogen or methyl, $R^{12}$, $R^{13}$, $R^{14}$, $R^{15}$, $R^{18}$, $R^{19}$, $R^{20}$, and $R^{21}$ are independently hydrogen or methyl, or two of $R^{12}$, $R^{13}$, $R^{14}$, $R^{15}$, $R^{18}$, $R^{19}$, $R^{20}$, and $R^{21}$ bonded to the same carbon can form carbonyl along with the carbon to which they are attached, and $R^{16}$ and $R^{22}$ are independently hydrogen or methyl.

In formula 1 above,

X is —NH— or —O—;

Z is —CN or —CF₃;

$R^1$ is methyl, ethyl, n-propyl, isopropyl, cyclopropyl, 1-methylcyclopropyl, tetrahydropyran-4-yl or tetrahydrofuran-3-yl; and

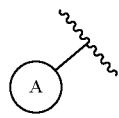

is

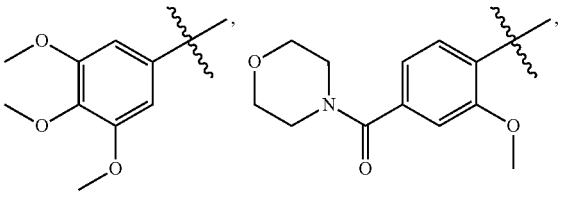

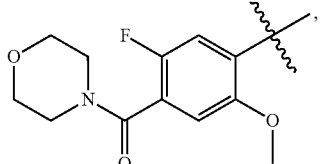

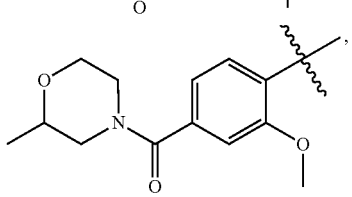

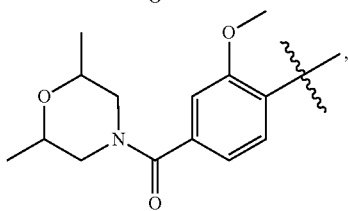

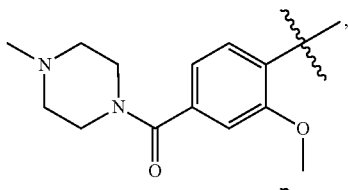

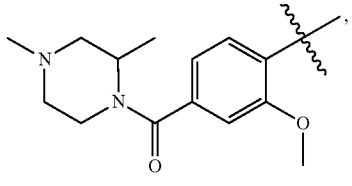

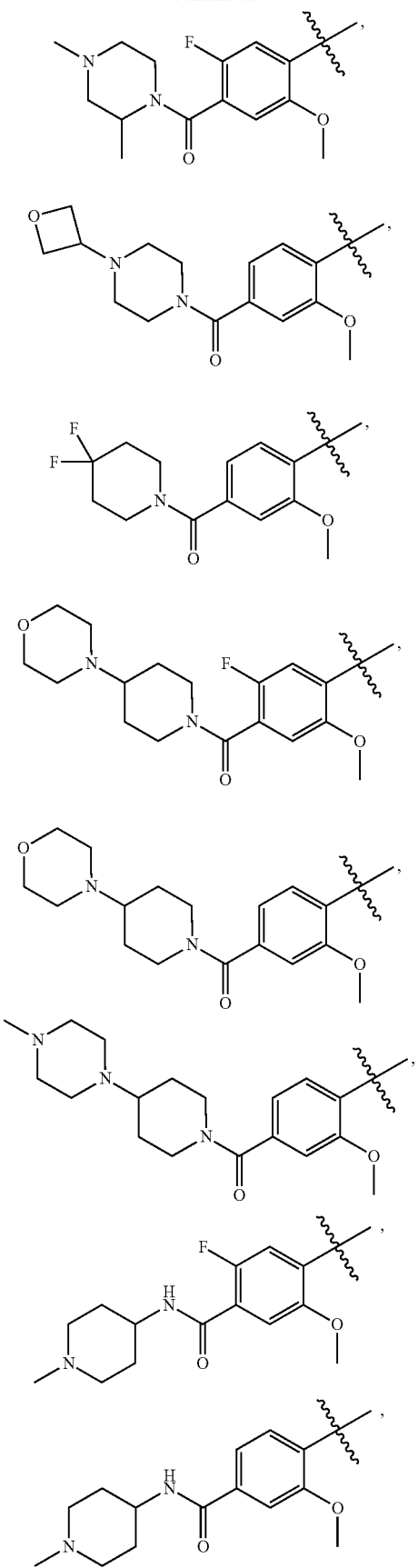
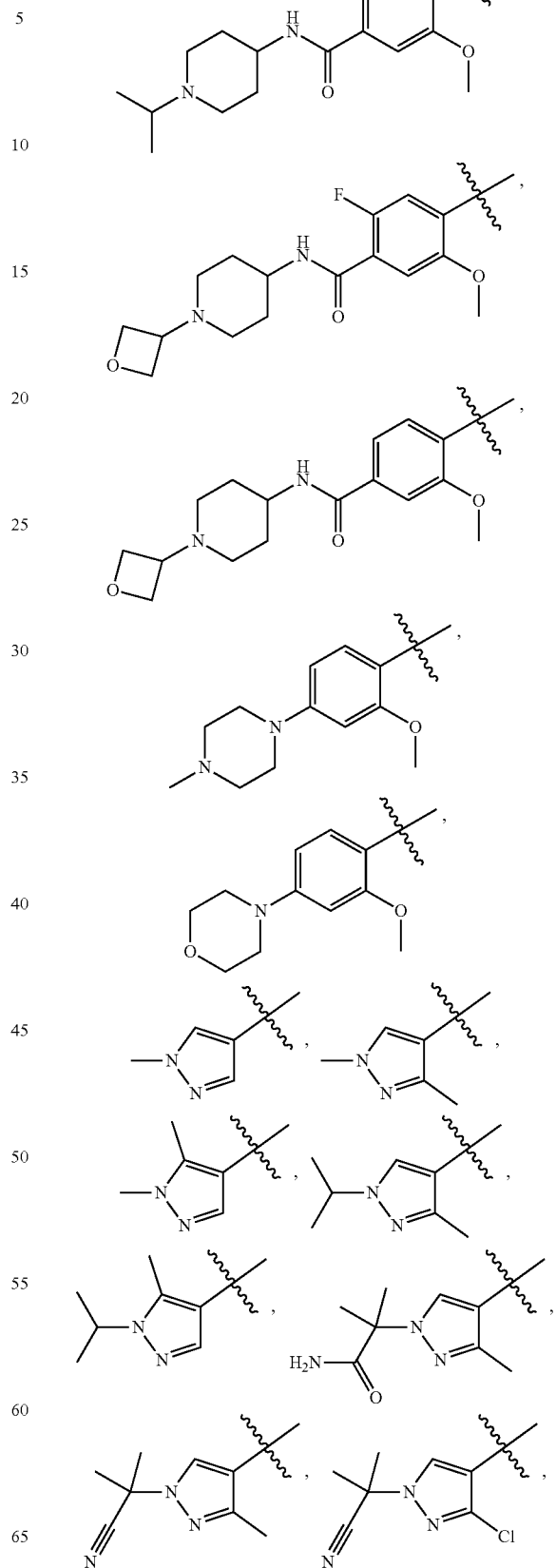

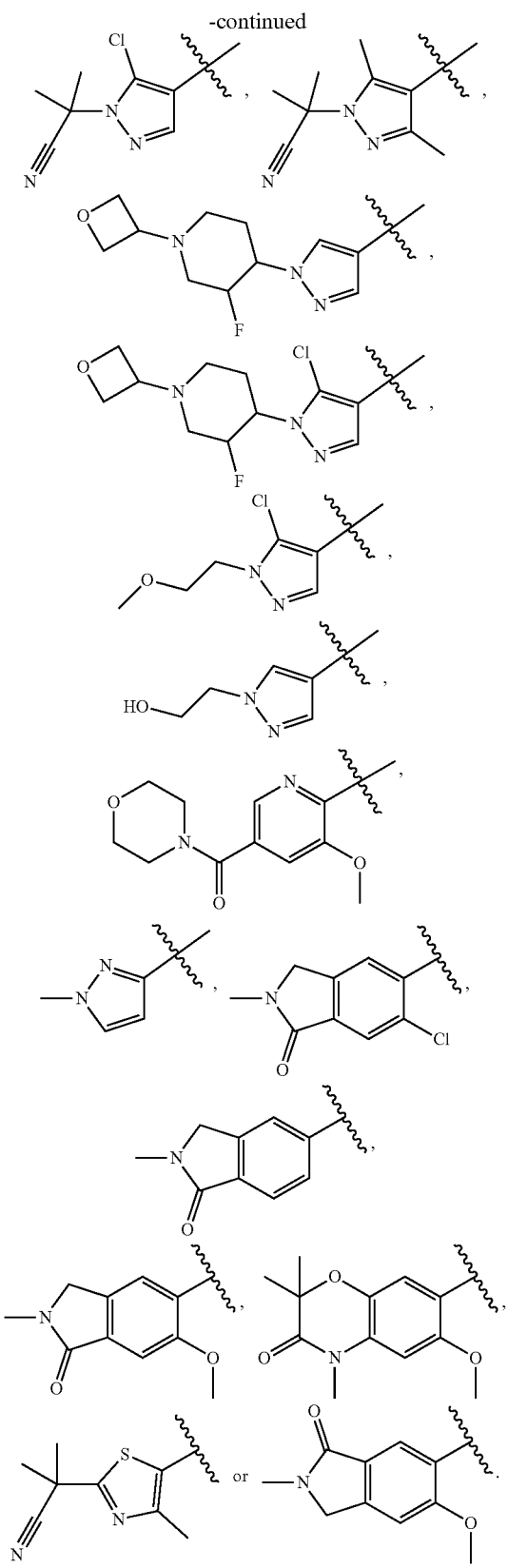

Preferable examples of the compound represented by formula 1 above include the following compounds:
(1) 2-((2-methoxy-4-(morpholine-4-carbonyl)phenyl)amino)-4-(methylamino)-7H-pyrrolo[2,3-d]pyrimidine-5-carbonitrile; (2) 4-(ethylamino)-2-((2-methoxy-4-(morpholine-4-carbonyl)phenyl)amino)-7H-pyrrolo[2,3-d]pyrimidine-5-carbonitrile; (3) 4-(ethylamino)-2-((3,4,5-trimethoxyphenyl)amino)-7H-pyrrolo[2,3-d]pyrimidine-5-carbonitrile; (4) 4-(ethylamino)-2-((1-methyl-1H-pyrazole-4-yl)amino)-7H-pyrrolo[2,3-d]pyrimidine-5-carbonitrile; (5) 4-(ethylamino)-2-((1-methyl-1H-pyrazole-3-yl)amino)-7H-pyrrolo[2,3-d]pyrimidine-5-carbonitrile; (6) 4-(ethylamino)-2-((5-fluoro-2-methoxy-4-(morpholine-4-carbonyl)phenyl)amino)-7H-pyrrolo[2,3-d]pyrimidine-5-carbonitrile; (7) 4-(ethylamino)-2-((5-fluoro-2-methoxy-4-(4-morpholinopiperidine-1-carbonyl)phenyl)amino)-7H-pyrrolo[2,3-d]pyrimidine-5-carbonitrile; (8) 4-(ethylamino)-2-((2-methoxy-4-(4-morpholinopiperidine-1-carbonyl)phenyl)amino)-7H-pyrrolo[2,3-d]pyrimidine-5-carbonitrile; (9) 2-((2-methoxy-4-(4-morpholinylpiperidine-1-carbonyl)phenyl)amino)-4-(methylamino)-7H-pyrrolo[2,3-d]pyrimidine-5-carbonitrile; (10) 2-((5-fluoro-2-methoxy-4-(morpholine-4-carbonyl)phenyl)amino)-4-(methylamino)-7H-pyrrolo[2,3-d]pyrimidine-5-carbonitrile; (11) 2-((5-fluoro-2-methoxy-4-(4-morpholinopiperidine-1-carbonyl)phenyl)amino)-4-(methyl amino)-7H-pyrrolo[2,3-d]pyrimidine-5-carbonitrile; (12) 2-((2-methoxy-4-(morpholine-4-carbonyl)phenyl)amino)-4-(propylamino)-7H-pyrrolo[2,3-d]pyrimidine-5-carbonitrile; (13) 2-((2-methoxy-4-(4-morpholinopiperidine-1-carbonyl)phenyl)amino)-4-(propylamino)-7H-pyrrolo[2,3-d]pyrimidine-5-carbonitrile; (14) 2-((5-fluoro-2-methoxy-4-(morpholine-4-carbonyl)phenyl)amino)-4-(propylamino)-7H-pyrrolo[2,3-d]pyrimidine-5-carbonitrile; (15) 2-((5-fluoro-2-methoxy-4-(4-morpholinopiperidine-1-carbonyl)phenyl)amino)-4-(propylamino)-7H-pyrrolo[2,3-d]pyrimidine-5-carbonitrile; (16) 4-(cyclopropylamino)-2-((2-methoxy-4-(morpholine-4-carbonyl)phenyl)amino)-7H-pyrrolo[2,3-d]pyrimidine-5-carbonitrile; (17) 4-(cyclopropylamino)-2-((2-methoxy-4-(4-morpholinopiperidine-1-carbonyl)phenyl)amino)-7H-pyrrolo[2,3-d]pyrimidine-5-carbonitrile; (18) 4-(cyclopropylamino)-2-((5-fluoro-2-methoxy-4-(morpholine-4-carbonyl)phenyl)amino)-7H-pyrrolo[2,3-d]pyrimidine-5-carbonitrile; (19) 4-(cyclopropylamino)-2-((5-fluoro-2-methoxy-4-(4-morpholinopiperidine-1-carbonyl)phenyl)amino)-7H-pyrrolo[2,3-d]pyrimidine-5-carbonitrile; (20) (R)-2-((2-methoxy-4-(2-methylmorpholine-4-carbonyl)phenyl)amino)-4-(methylamino)-7H-pyrrolo[2,3-d]pyrimidine-5-carbonitrile; (21) (S)-2-((2-methoxy-4-(2-methylmorpholine-4-carbonyl)phenyl)amino)-4-(methylamino)-7H-pyrrolo[2,3-d]pyrimidine-5-carbonitrile; (22) 2-((4-((2R,6S)-2,6-dimethylmorpholine-4-carbonyl)-2-methoxyphenyl)amino)-4-(methylamino)-7H-pyrrolo[2,3-d]pyrimidine-5-carbonitrile; (23) 2-((4-(4,4-difluoropiperidine-1-carbonyl)-2-methoxyphenyl amino)-4-(methylamino)-7H-pyrrolo[2,3-d]pyrimidine-5-carbonitrile; (24) 2-((4-((2R,6S)-2,6-dimethylmorpholine-4-carbonyl)-2-methoxyphenyl)amino)-4-(ethylamino)-7H-pyrrolo[2,3-d]pyrimidine-5-carbonitrile; (25) (R)-4-(ethylamino)-2-((2-methoxy-4-(2-methylmorpholine-4-carbonyl)phenyl)amino)-7H-pyrrolo[2,3-d]pyrimidine-5-carbonitrile; (26) (S)-4-(ethylamino)-2-((2-methoxy-4-(2-methylmorpholine-4-carbonyl)phenyl)amino)-7H-pyrrolo[2,3-d]pyrimidine-5-carbonitrile; (27) 2-((4-(4,4-difluoropiperidine-1-carbonyl)-2-methoxyphenyl)amino)-4-(ethylamino)-7H-pyrrolo[2,3-d]pyrimidine-5-carbonitrile; (28) 6-((1,3-dimethyl-1H-pyrazole-4-yl)amino)-4-(methylamino)-1H-pyrrolo[2,3-b]pyrimidine-3-carbonitrile; (29) 6-((1,5-dimethyl-1H-pyrazole-4-yl)amino)-4-(methyl amino)-1H-pyrrolo[2,3-b]pyrimidine-3-carbonitrile; (30) 6-((1-isopropyl-3-methyl-1H-pyrazole-4-yl)amino)-4-(methylamino)-1H-pyrrolo[2,3- b]pyrimidine-3-carbonitrile; (31) 6-((1-isopropyl-5-methyl-1H-pyrazole-4-yl)amino)-4-(methylamino)-1H-pyrrolo[2,3-b]pyrimidine-3-carbonitrile; (32) 2-((1,3-dimethyl-1H-pyrazole-4-yl)amino)-4-(ethylamino)-7H-pyrrolo[2,3-d]pyrimidine-5-carbonitrile; (33) 2-((1,5-dimethyl-1H-pyrazole-4-yl)amino)-4-(ethylamino)-7H-pyrrolo[2,3-d]pyrimidine-5-carbonitrile; (34) 4-(ethylamino)-2-((1-isopropyl-3-methyl-1H-pyrazole-4-yl)amino)-7H-pyrrolo[2,3-d]pyrimidine-5-carbonitrile; (35) 4-(ethylamino)-2-((1-isopropyl-5-methyl-1H-pyrazole-4-yl)amino)-7H-pyrrolo[2,3-d]pyrimidine-5-carbonitrile; (36) 2-((2-methoxy-4-(morpholine-4-carbonyl)phenyl)amino)-4-((1-methylcyclopropyl)amino)-7H-pyrrolo[2,3-d]pyrimidine-5-carbonitrile; (37) 2-((5-fluoro-2-methoxy-4-(morpholine-4-carbonyl)phenyl)amino)-4-((1-methylcyclopropyl)amino)-7H-pyrrolo[2,3-d]pyrimidine-5-carbonitrile; (38) 2-((1-isopropyl-5-methyl-1H-pyrazole-4-yl)amino)-4-((1-methylcyclopropyl)amino)-7H-pyrrolo[2,3-d]pyrimidine-5-carbonitrile; (39) 2-((1-isopropyl-3-methyl-1H-pyrazole-4-yl)amino)-4-((1-methylcyclopropyl)amino)-7H-pyrrolo[2,3-d]pyrimidine-5-carbonitrile; (40) 2-((1,3-dimethyl-1H-pyrazole-4-yl)amino)-4-((1-methylcyclopropyl)amino)-7H-pyrrolo[2,3-d]pyrimidine-5-carbonitrile; (41) 2-((1,5-dimethyl-1H-pyrazole-4-yl)amino)-4-((1-methylcyclopropyl)amino)-7H-pyrrolo[2,3-d]pyrimidine-5-carbonitrile; (42) (R)-2-((2-methoxy-4-(2-methylmorpholine-4-carbonyl)phenyl)amino)-4-((1-methylcyclopropyl)amino)-7H-pyrrolo[2,3-d]pyrimidine-5-carbonitrile; (43) (S)-2-((2-methoxy-4-(2-methylmorpholine-4-carbonyl)phenyl)amino)-4-((1-methylcyclopropyl)amino)-7H-pyrrolo[2,3-d]pyrimidine-5-carbonitrile; (44) 2-((4-((2R,6S)-2,6-dimethylmorpholine-4-carbonyl)-2-methoxyphenyl)amino)-4-((1-methylcyclopropyl)amino)-7H-pyrrolo[2,3-d]pyrimidine-5-carbonitrile; (45) 2-((4-(4,4-difluoropiperidine-1-carbonyl)-2-methoxyphenyl)amino)-4-((1-methylcyclopropyl)amino)-7H-pyrrolo[2,3-d]pyrimidine-5-carbonitrile; (46) 2-(4-((5-cyano-4-(methylamino)-7H-pyrrolo[2,3-d]pyrimidine-2-yl)amino)-3-methyl-1H-pyrazole-1-yl)-2-methylpropaneamide; (47) 2-((1-(2-cyanopropane-2-yl)-3-methyl-1H-pyrazole-4-yl)amino)-4-(methylamino)-7H-pyrrolo[2,3-d]pyrimidine-5-carbonitrile; (48) 4-(ethylamino)-2-((3-methoxy-5-(morpholine-4-carbonyl)pyridine-2-yl)amino)-7H-pyrrolo[2,3-d]pyrimidine-5-carbonitrile; (49) 2-((1-(2-cyanopropane-2-yl)-3-methyl-1H-pyrazole-4-yl)amino)-4-((1-methylcyclopropyl)amino)-7H-pyrrolo[2,3-d]pyrimidine-5-carbonitrile; (50) 2-((5-chloro-1-((3S,4S)-3-fluoro-1-(oxetane-3-yl)piperidine-4-yl)-1H-pyrazole-4-yl)amino)-4-(methylamino)-7H-pyrrolo[2,3-d]pyrimidine-5-carbonitrile; (51) 2-((5-chloro-1-((3S,4S)-3-fluoro-1-(oxetane-3-yl)piperidine-4-yl)-1H-pyrazole-4-yl)amino)-4-(ethylamino)-7H-pyrrolo[2,3-d]pyrimidine-5-carbonitrile; (52) 2-((5-chloro-1-((3S,4S)-3-fluoro-1-(oxetane-3-yl)piperidine-4-yl)-1H-pyrazole-4-yl)amino)((1-methylcyclopropyl)amino)-7H-pyrrolo[2,3-d]pyrimidine-5-carbonitrile; (53) 4-(ethylamino)-2-((1-(3S,4S)-3-fluoro-1-(oxetane-3-yl)piperidine-4-yl)-1H-pyrazole-4-yl)amino)-7H-pyrrolo[2,3-d]pyrimidine-5-carbonitrile; (54) 2-((1-((3S,4S)-3-fluoro-1-(oxetane-3-yl)piperidine-4-yl)-1H-pyrazole-4-yl)amino)-4-((methylcyclopropyl)amino)-7H-pyrrolo[2,3-d]pyrimidine-5-carbonitrile; (55) 4-((5-cyano-4-(methylamino)-7H-pyrrolo[2,3-d]pyrimidine-2-yl)amino)-3-methoxy-N-(1-methylpiperidine-4-yl)benzamide; (56) 4-((5-cyano-4-(ethylamino)-7H-pyrrolo[2,3-d]pyrimidine-2-yl)amino)-3-methoxy-N-(1-methylpiperidine-4-yl)benzamide; (57) 2-((2-methoxy-4-(oxetane-3-yl)piperazine-1-carbonyl)phenyl)amino)-4-(methylamino)-7H-pyrrolo[2,3-d]pyrimidine-5-carbonitrile; (58) 4-(ethylamino)-2-((2-methoxy-4-(4-(oxetane-3-yl)piperazine-1-carbonyl)phenyl)amino)-7H-pyrrolo[2,3-d]pyrimidine-5-carbonitrile; (59) 2-((5-chloro-1-(2-methoxyethyl)-1H-pyrazole-4-yl)amino)-4-(methylamino)-7H-pyrrolo[2,3-d]pyrimidine-5-carbonitrile; (60) 4-((5-cyano-4-(ethylamino)-7H-pyrrolo[2,3-d]pyrimidine-2-yl)amino)-3-methoxy-N-(1-(oxetane-3-yl)piperidine-4-yl)benzylamide; (61) 4-((5-cyano-4-(methylamino)-7H-pyrrolo[2,3-d]pyrimidine-2-yl)amino)-3-methoxy-N-(1-(oxetane-3-yl)piperidine-4-yl)benzylamide; (62) 2-((5-chloro-1-(2-methoxyethyl)-1H-pyrazole-4-yl)amino)-4-(ethylamino)-7H-pyrrolo[2,3-d]pyrimidine-5-carbonitrile; (63) 4-((5-cyano-4-(methylamino)-7H-pyrrolo[2,3-d]pyrimidine-2-yl)amino)-2-fluoro-5-methoxy-N-(1-(oxetane-3-pyrrolidine-1-yl)piperidine-4-yl)benzamide; (64) 4-((5-cyano-4-(ethylamino)-7H-pyrrolo[2,3-d]pyrimidine-2-yl)amino)-2-fluoro-5-methoxy-N-(1-(oxetane-3-pyrrolidine-1-yl)piperidine-4-yl)benzamide; (65) 4-((5-cyano-4-(methylamino)-7H-pyrrolo[2,3-d]pyrimidine-2-yl)amino)-2-fluoro-5-methoxy-N-(1-methylpiperidine-4-yl)benzamide; (66) 4-((5-cyano-4-(ethylamino)-7H-pyrrolo[2,3-d]pyrimidine-2-yl)amino)-2-fluoro-5-methoxy-N-(1-methylpiperidine-4-yl)benzamide; (67) 4-((5-cyano-4-(methylamino)-7H-pyrrolo[2,3-d]pyrimidine-2-yl)amino)-2-fluoro-N-(1-isopropylpiperidine-4-yl)-5-methoxybenzamide; (68) 4-((5-cyano-4-(ethylamino)-7H-pyrrolo[2,3-d]pyrimidine-2-yl)amino)-2-fluoro-N-(1-isopropylpiperidine-4-yl)-5-methoxybenzamide; (69) 2-((1-(2-hydroxyethyl)-1H-pyrazole-4-yl)amino)-4-(methylamino)-7H-pyrrolo[2,3-d]pyrimidine-5-carbonitrile; (70) 4-(ethylamino)-2-((1-(2-hydroxyethyl)-1H-pyrazole-4-yl)amino)-7H-pyrrolo[2,3-d]pyrimidine-5-carbonitrile; (71) 2-((3-chloro-1-(2-cyanopropane-2-yl)-1H-pyrazole-4-yl)amino)-4-(methylamino)-7H-pyrrolo[2,3-d]pyrimidine-5-carbonitrile; (72) 2-((3-chloro-1-(2-cyanopropane-2-yl)-1H-pyrazole-4-yl)amino)-4-(ethylamino)-7H-pyrrolo[2,3-d]pyrimidine-5-carbonitrile; (73) 2-((5-chloro-1-(2-cyanopropane-2-yl)-1H-pyrazole-4-yl)amino)-4-(methylamino)-7H-pyrrolo[2,3-d]pyrimidine-5-carbonitrile; (74) 2-((5-chloro-1-(2-cyanopropane-2-yl)-1H-pyrazole-4-yl)amino)-4-(ethylamino)-7H-pyrrolo[2,3-d]pyrimidine-5-carbonitrile; (75) (R)-2-((4-(2,4-dimethylpiperazine-1-carbonyl)-2-methoxyphenyl)amino)-4-(methylamino)-7H-pyrrolo[2,3-d]pyrimidine-5-carbonitrile; (76) (R)-2-((4-(2,4-dimethylpiperazine-1-carbonyl)-2-methoxyphenyl)amino)-4-(ethylamino)-7H-pyrrolo[2,3-d]pyrimidine-5-carbonitrile; (77) 2-((1-(2-cyanopropane-2-yl)-3,5-dimethyl-1H-pyrazole-4-yl)amino)-4-(methylamino)-7H-pyrrolo[2,3-d]pyrimidine-5-carbonitrile; (78) 2-((1-(2-cyanopropane-2-yl)-3,5-dimethyl-1H-pyrazole-4-yl)amino)-4-(ethylamino)-7H-pyrrolo[2,3-d]pyrimidine-5-carbonitrile; (79) (R)-2-((4-(2,4-dimethylpiperazine-1-carbonyl)-5-fluoro-2-methoxyphenyl)amino)-4-(ethylamino)-7H-pyrrolo[2,3-d]pyrimidine-5-carbonitrile; (80) (R)-2-((4-(2,4-dimethylpiperazine-1-carbonyl)-5-fluoro-2-methoxyphenyl)amino)-4-(methylamino)-7H-pyrrolo[2,3-d]pyrimidine-5-carbonitrile; (81) 4-((5-cyano-4-((1-methylcyclopropyl)amino)-7H-pyrrolo[2,3-]pyrimidine-2-yl)amino)-2-fluoro-5-methoxy-N-(1-(oxetane-3-yl)piperidine-4-yl)benzamide; (82) 4-((5-cyano-4-((1-methylcyclopropyl)amino)-7H-pyrrolo[2,3-d]pyrimidine-2-yl)amino)-2-fluoro-N-(1-isopropylpiperidine-4-yl)-5-methoxybenzamide; (83) 4-((5-cyano-4-((1-methylcyclopropyl)amino)-7H-pyrrolo[2,3-d]pyrimidine-2-yl)amino)-2-fluoro-5-methoxy-N-(1-methylpiperidine-4-yl)benzamide; (84) 2-((2-methoxy-4-(morpholine-4-carbonyl)

phenyl)amino)-4-((tetrahydro-2H-pyran-4-yl)oxy)-7H-pyrrolo[2,3-d]pyrimidine-5-carbonitrile; (85) 2-((2-methoxy-4-(morpholine-4-carbonyl)phenyl)amino)-4-((tetrahydro-2H-pyran-4-yl)oxy)-7H-pyrrolo[2,3-d] pyrimidine-5-carbonitrile; (86) 2-((2-methoxy-4-(morpholine-4-carbonyl)phenyl)amino)-4-((tetrahydrofuran-3-yl)oxy)-7H-pyrrolo[2,3-d]pyrimidine-5-carbonitrile; (87) 2-((2-methoxy-4-(4-morpholinopiperidine-1-carbonyl)phenyl)amino)-4-((tetrahydrofuran-3-yl)oxy)-7H-pyrrolo[2,3-d]pyrimidine-5-carbonitrile; (88) (S)-2-((2-methoxy-4-(morpholine-4-carbonyl)phenyl)amino)-4-((tetrahydrofuran-3-yl)oxy)-7H-pyrrolo[2,3-d]pyrimidine-5-carbonitrile; (89) (R)-2-((2-methoxy-4-(morpholine-4-carbonyl)phenyl)amino)-4-((tetrahydrofuran-3-yl)oxy)-7H-pyrrolo[2,3-d]pyrimidine-5-carbonitrile; (90) 4-isoprofoxy-2-((2-methoxy-4-(morpholine-4-carbonyl)phenyl)amino)-7H-pyrrolo[2,3-d]pyrimidine-5-carbonitrile; (91) 4-isoprofoxy-2-((2-methoxy-4-(4-morpholinopiperidine-1-carbonyl)phenyl)amino)-7H-pyrrolo[2,3-d] pyrimidine-5-carbonitrile; (92) (S)-2-((5-fluoro-2-methoxy-4-(morpholine-4-carbonyl)phenyl)amino)-4-((tetrahydrofuran-3-yl)oxy)-7H-pyrrolo[2,3 d]pyrimidine-5-carbonitrile; (93) (S)-2-((5-fluoro-2-methoxy-4-(4-morpholinopiperidine-1-carbonyl)phenyl) amino)-4-((tetrahydrofuran-3-yl)oxy)-7H-pyrrolo[2,3-d]pyrimidine-5-carbonitrile; (94) 2-((1-(2-cyanopropane-2-yl)-3-methyl-1H-pyrazole-4-yl)amino)-4-(1-methylcyclopropoxy)-7H-pyrrolo[2,3-d]pyrimidine-5-carbonitrile; (95) 2-((2-methoxy-4-(morpholine-4-carbonyl) phenyl)amino)-4-(1-methylcyclopropoxy)-7H-pyrrolo[2,3-d]pyrimidine-5-carbonitrile; (96) 2-((5-chloro-1-((3S,4S)-3-fluoro-1-(oxetane-3-yl)piperidine-4-yl)-1H-pyrazole-4-yl) amino)(1-methylcyclopropoxy)-7H-pyrrolo[2,3-]pyrimidine-5-carbonitrile; (97) 2-((5-fluoro-2-methoxy-4-(morpholine-4-carbonyl)phenyl)amino)-4-(1-methyl cyclopropoxy)-7H-pyrrolo[2,3-d]pyrimidine-5-carbonitrile; (98) (R)-2-((2-methoxy-4-(2-methylmorpholine-4-carbonyl)phenyl)amino)-4-(1-methylcyclopropoxy)-7H-pyrrolo[2,3d]carbonitrile; (99) (S)-2-((2-methoxy-4-(2-methylmorpholine-4-carbonyl)phenyl)amino)-4-(1-methyl cyclopropoxy)-7H-pyrrolo[2,3-d]pyrimidine-5-carbonitrile; (100) 2-((4-((2R,6S)-2,6-dimethylmorpholine-4-carbonyl)-2-methoxyphenyl)amino)-4-(1-methylcyclopropoxy)-7H-pyrrolo[2,3-d]pyrimidine-5-carbonitrile; (101) 2-((1-((3S,4S)-3-fluoro-1-(oxetane-3-yl)piperidine-4-yl)-1H-pyrazole-4-yl)amino)-4-(1-methylcyclopropoxy)-7H-pyrrolo[2,3-d]pyrimidine-5-carbonitrile; (102) $N^2$-(5-chloro-1-((3S,4S)-3-fluoro-1-(oxetane-3-yl)piperidine-4-yl)-1H-pyrazole-4-yl)-$N^4$-ethyl-5-(trifluoromethyl)-7H-pyrrolo[2,3-d]pyrimidine-2,4-diamine; (103) 2-(4-((4-(ethylamino)-5-(trifluoromethyl)-7H-pyrrolo[2,3-d]pyrimidine-2-yl)amino)-3-methyl-1H-pyrazole-1-yl)-2-methylpropanenitrile; (104) (4-((4-(ethylamino)-5-(trifluoromethyl)-7H-pyrrolo[2,3-d]pyrimidine-2-yl)amino)-3-methoxyphenyl)(4-morpholinopiperidine-1-yl)methanone; (105) (4-((4-(ethylamino)-5-(trifluoromethyl)-7H-pyrrolo[2,3-d]pyrimidine-2-yl)amino)-3-methoxyphenyl)(morpholino)methanone; (106) (4-(ethylamino)-(trifluoromethyl)-7H-pyrrolo[2,3-d]pyrimidine-2-yl)amino)-3-methoxyphenyl)(4-(4-methylpiperazine-1-yl)piperidine-1-yl)methanone; (107) (4-((4-(ethylamino)-5-(trifluoromethyl)-7H-pyrrolo[2,3-d]pyrimidine-2-yl)amino)-3-methoxyphenyl)(4-methylpiperazine-1-yl)methanone; (108) (R)-(4-((4-(ethylamino)-5-(trifluoromethyl)-7H-pyrrolo[2,3-d]pyrimidine-2-yl)amino)-3-methoxyphenyl)(2-methylmorpholino)methanone; (109) ((2R,6S)-2,6-dimethylmorpholino)((4-((4-(ethylamino)-5-(trifluoromethyl)-7H-pyrrolo[2,3-d]pyrimidine-2-yl)amino)-3-methoxyphenyl)methanone; (110) (4,4-difluoropiperidine-1-yl)(4-((4-(ethylamino)-5-(trifluoromethyl)-7H-pyrrolo[2,3-d]pyrimidine-2-yl)amino)-3-methoxy phenyl)methanone; (111) (S)-(4-((4-(ethylamino)-5-(trifluoromethyl)-7H-pyrrolo[2,3-d]pyrimidine-2-yl)amino)-3-methoxyphenyl)(2-methylmorpholino)methanone; (112) (3-methoxy-4-((4-(methylamino)-5-(trifluoromethyl)-7H-pyrrolo[2,3-d] pyrimidine-2-yl)amino)phenyl)(morpholino)methanone; (113) 2-(4-((4-(ethylamino)-5-(trifluoromethyl)-7H-pyrrolo[2,3-d]pyrimidine-2-yl)amino)-3-methyl-1H-pyrazole-1-yl)-2-methylpropaneamide; (114) $N^4$-ethyl-$N^2$-(2-methoxy-4-(4-methylpiperazine-1-yl)phenyl)-5-(trifluoromethyl)-7H-pyrrolo[2,3-d]pyrimidine-2,4-diamine; (115) $N^4$-ethyl-$N^2$-(2-methoxy-4-morpholinophenyl)-5-(trifluoromethyl)-7H-pyrrolo[2,3-d]pyrimidine-2,4-diamine; (116) 4-((4-(ethylamino)-5-(trifluoromethyl)-7H-pyrrolo[2,3-d]pyrimidine-2-yl)amino)-2-fluoro-5-methoxy-N-(1-(oxetanepiperidine-4-yl)benzamide; (117) $N^2$-(5-chloro-1-((3S,4S)-3-fluoro-1-(oxetane-3-yl)piperidine-4-yl)-1H-pyrazole-4-yl)-$N^4$-cyclopropyl-5-(trifluoromethyl)-7H-pyrrolo[2,3-d]pyrimidine-2,4-diamine; (118) (4-((4-(cyclopropylamino)-5-(trifluoromethyl)-7H-pyrrolo[2,3-d]pyrimidine-2-yl)amino)-3-methoxyphenyl)(morpholino)methanone; (119) (4-((4-(cyclopropylamino)-5-(trifluoromethyl)-7H-pyrrolo[2,3-d]pyrimidine-2-yl)amino)-3-methoxyphenyl)(4-methylpiperazine-1-yl)methanone; (120) (4-((4-(cyclopropylamino)-5-(trifluoromethyl)-7H-pyrrolo[2,3-d]pyrimidine-2-yl)amino)-3-methoxyphenyl)(4-(4-methylpiperazine-1-yl)piperidine-1-yl)methanone; (121) (3-methoxy-4-((4-((1-methylcyclopropyl)amino)-5-(trifluoromethyl)-7H-pyrrolo[2,3-d]pyrimidine-2-yl)amino)phenyl)(4-methylpiperazine-1-yl)methanone; (122) (3-methoxy-4-((4-((1-methylcyclopropyl)amino)-5-(trifluoromethyl)-7H-pyrrolo[2,3-d]pyrimidine-2-yl)amino)phenyl)(4-(4-methylpiperazine-1-yl)piperidine-1-yl)methanol; (123) (R)-(2,4-dimethylpiperazine-1-yl)(2-fluoro-5-methoxy-4-((4-(methylamino)-5-(trifluoromethyl)-7H-pyrrolo[2,3-d] pyrimidine-2-yl)amino)phenyl)methanone; (124) (3-methoxy-4-((4-(((tetrahydrofuran-3-yl)oxy)-5-(trifluoromethyl)-7H-pyrrolo[2,3-d]pyrimidine-2-yl)amino)phenyl)(morpholino)methanone; (125) (3-methoxy-4-((4-(((tetrahydrofuran-3-yl)oxy)-5-(trifluoromethyl)-7H-pyrrolo[2, 3-d]pyrimidine-2-yl)amino)phenyl)-methylpiperazine-1-yl) methanone; (126) (3-methoxy-4-((4-(((tetrahydrofuran-3-yl)oxy)-5-(trifluoromethyl)-7H-pyrrolo[2,3-d]pyrimidine-2-yl)amino)phenyl)-(4-methylpiperazine-1-yl)piperidine-1-yl)methanone; (127) N-(5-chloro-1-((3S,4S)-3-fluoro-1-(oxetane-3-yl)piperidine-4-yl)-1H-pyrazole-4-yl)-4-((tetrahydrofuranoxy)-5-(trifluoromethyl)-7H-pyrrolo[2,3-d]pyrimidine-2-amine; (128) 2-((6-chloro-2-methyl-1-oxoisoindol-5-yl)amino)-4-(ethylamino)-7H-pyrrolo[2,3-d]pyrimidine-5-carbonitrile; (129) 4-(ethylamino)-2-((2-methyl-1-oxoisoindol-5-yl)amino)-7H-pyrrolo[2,3-d] pyrimidine-5-carbonitrile; (130) 4-(ethylamino)-2-((6-methoxy-2-methyl-1-oxoisoindol-5-yl)amino)-7H-pyrrolo[2,3-d]pyrimidine-5-carbonitrile; (131) 4-(ethylamino)-2-((6-methoxy-2,2,4-trimethyl-3-oxo-3,4-dihydro-2H-benzo[b][1,4]oxazine-7-yl)amino)-7H-pyrrolo[2,3-d]pyrimidine-5-carbonitrile; (132) 2-((2-(2-cyanopropane-2-yl)-4-methylthiazole-5-yl)amino)-4-(ethyl amino)-7H-pyrrolo[2,3-d]pyrimidine-5-carbonitrile; (133) 5-((4-(ethylamino)-5-(trifluoromethyl)-7H-pyrrolo[2,3-d]pyrimidine-2-yl)amino)-6-methoxy-2-methylisoindolin-1-one; (134) 6-((4-(ethylamino)-5-(trifluoromethyl)-7H-pyrrolo[2,3-d]

pyrimidine-2-yl)amino)-5-methoxy-2-methylisoindolin-1-one; (135) 6-chloro-5-((4-(ethylamino)-5-(trifluoromethyl)-7H-pyrrolo[2,3-d]pyrimidine-2-yl)amino)-2-methyl isoindolin-1-one; (136) 5-((4-(ethylamino)-5-(trifluoromethyl)-7H-pyrrolo[2,3-d]pyrimidine-2-yl)amino)-2-methylisoindolin-1-one; and (137) 7-((4-(ethylamino)-5-(trifluoromethyl)-7H-pyrrolo[2,3-d]pyrimidine-2-yl)amino)-6-methoxy-2,2,4-trimethyl-2H-benzo[1,4]oxazine-3(4H)-one.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. Wherein, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, an optical isomer, or a hydrate possibly produced from the same.

The compound represented by formula 1 according to the present invention, an optical isomer thereof or a pharmaceutically acceptable salt thereof has excellent activity of inhibiting LRRK2 kinase, inhibiting phosphorylation in NIH-3T3 cell line expressing LRRK2 and inhibiting phosphorylation in NCC01 and 448T cell lines which are the cell lines derived from brain tumor patients. Therefore, the compound represented by formula 1 according to the present invention, an optical isomer thereof or a pharmaceutically acceptable salt thereof can be effectively used for the treatment or prevention of LRRK2 related disease (see Experimental Examples 1-3).

The compound represented by formula 1 according to the present invention, an optical isomer thereof or a pharmaceutically acceptable salt thereof has the activity of inhibiting not only LRRK2 kinase but also other kinases such as ABL, ALK, BUB1, CAMK1B, CAMK4, CAMKK1, CAMKK2, CHEK2m, CLK1, CLK2, CLK3, CLK4, CSNK1A1, CSNK1A1L, CSNK1D, CSNK1E, CSNK1G2, CSNK1G3, CSNK2A1, DAPK1, DAPK2, DAPK3, DCAMKL1, DRAK1, DRAK2, DYRK1A, DYRK1B, ERK5, FAK, FER, FES, FLT, GAK, HIPK1, HIPK2, HIPK3, HUNK, IGF1R, INSR, INSRR, IRAK4, JAK1, JNK1, JNK2, JNK3, KIT, LRRK2, LTK, MAP3K15, MAPKAPK2, MAPKAPK5, MEK3, MEK4, MEK5, MEK6, MKNK2, MYLK, MYO3B, NEK10, NIK, OSR1, PDGFRA, PHKG1, PHKG2, PIP5K1C, PIP5K2C, PLK1, PLK3, PLK4, PRKD1, PRKD2, PRKD3, PYK2, RIOK2, RIPK5, ROS1, RPS6KA4, RPS6KA5, RSK3, STK33, STK39, SYK, TAK1, TGFBR1, TNK1, TNK2, TSSK1B, TTK, YSK4 or ZAP70, so that it can be effectively used for the treatment of ABL, ALK, BUB1, CAMK1B, CAMK4, CAMKK1, CAMKK2, CHEK2m, CLK1, CLK2, CLK3, CLK4, CSNK1A1, CSNK1A1L, CSNK1D, CSNK1E, CSNK1G2, CSNK1G3, CSNK2A1, DAPK1, DAPK2, DAPK3, DCAMKL1, DRAK1, DRAK2, DYRK1A, DYRK1B, ERK5, FAK, FER, FES, FLT, GAK, HIPK1, HIPK2, HIPK3, HUNK, IGF1R, INSR, INSRR, IRAK4, JAK1, JNK1, JNK2, JNK3, KIT, LRRK2, LTK, MAP3K15, MAPKAPK2, MAPKAPK5, MEK3, MEK4, MEK5, MEK6, MKNK2, MYLK, MYO3B, NEK10, NIK, OSR1, PDGFRA, PHKG1, PHKG2, PIP5K1C, PIP5K2C, PLK1, PLK3, PLK4, PRKD1, PRKD2, PRKD3, PYK2, RIOK2, RIPK5, ROS1, RPS6KA4, RPS6KA5, RSK3, STK33, STK39, SYK, TAK1, TGFBR1, TNK1, TNK2, TSSK1B, TTK, YSK4 or ZAP70 related diseases as well (see Experimental Example 4).

As shown in FIG. 1, when the compound of the present invention was treated, the amount of detectable P-LRRK2 was significantly low, compared with when the compound was not treated. The result indicates that the compound of the present invention can inhibit phosphorylation of LRRK2 efficiently.

Therefore, the pyrrolo-pyrimidine derivative compound of the present invention can inhibit phosphorylation of intracellular LRRK2 efficiently, so that it can be effectively used as a pharmaceutical composition for the prevention or treatment of LRRK2 related disease.

The present invention also provides a preparation method of the compound represented by formula 1 comprising the following steps, as shown in reaction formula 1 below:

preparing a compound represented by formula 4 by reacting a compound represented by formula 2 with a compound represented by formula 3 (step 1); and preparing a compound represented by formula 1 by reacting the compound represented by formula 4 prepared in step 1 above in the presence of an acid (step 2):

[Reaction Formula 1]

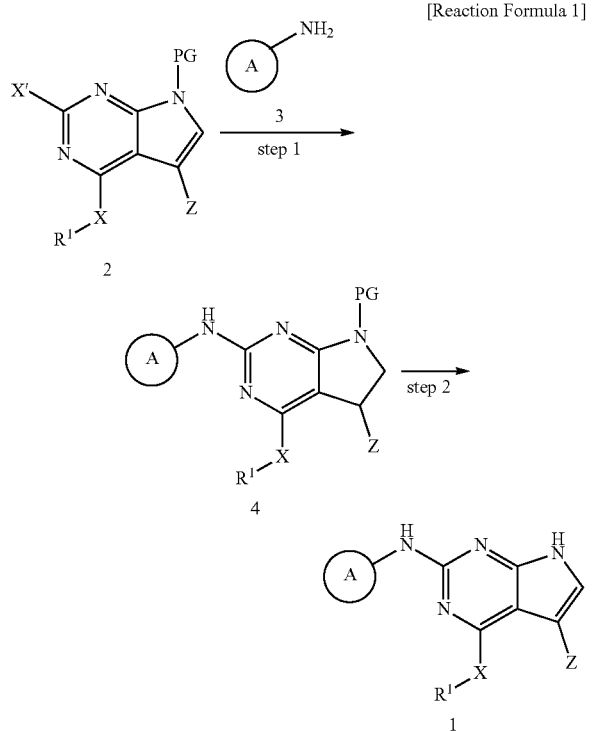

(In reaction formula 1, X, Z, R¹ and

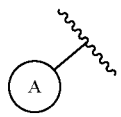

are as defined in formula 1 above;

X' is halogen; and

PG is (2-(trimethylsilyl)methoxy)methyl (SEM), p-methoxybenzyl (PMB), t-butyloxycarbonyl (BOC), carbobenzyloxy (Cbz), 9-fluorenylmethyloxycarbonyl (Fmoc), acetyl (Ac), benzoyl (Bz), benzyl (Bn), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), aryloxycarbonyl (Alloc) or p-methoxybenzyl (PMB)).

Hereinafter, the preparation method according to the present invention is described in more detail.

In the preparation method of the present invention, step 1 is to prepare a compound represented by formula 4 by reacting a compound represented by formula 2 with a compound represented by formula 3.

As a preferable example of step 1, a compound represented by formula 2 and a compound represented by formula 3 are dissolved in a solvent in the presence of a base and then gas is eliminated by ultrasonic treatment. A palladium catalyst and Xphos are added to the prepared reaction mixture at 100° C., followed by reaction for 2 hours.

Wherein, the base herein can be selected from the group consisting of such inorganic bases as cesium carbonate, sodium t-butoxide, potassium t-butoxide, sodium hydroxide, sodium carbonate, potassium carbonate and sodium hydride; and such organic bases as N,N-diaisopropylethylamine (DIPEA), 1,8-diazabicyclo[5.4.0]-7-undecene (DBU), pyridine and triethylamine. The selected base can be used in an equivalent amount or excess amount, alone or in combination. Herein, it is preferable to use potassium carbonate.

The palladium catalyst can be exemplified by tris(dibenzylideneacetone)palladium (Pd$_2$(dba)$_3$), tetrakis(triphenylphosphine)palladium (Pd(Ph$_3$P)$_4$), palladium charcoal (Pd—C), bis(triphenylphosphine)palladium dichloride (PdCl$_2$(PPh$_3$)$_2$), [1,1-bis(diphenylphosphino)ferrocene]dichloropalladium (PdCl$_2$(dppf)), allylpalladium chloride dimer ([PdCl(allyl)]$_2$), palladium acetate (Pd(OAc)$_2$) and palladium chloride(PdCl$_2$), among which tris(dibenzylideneacetone)palladium (Pd$_2$(dba)$_3$) is preferred.

The reaction solvent usable herein is exemplified by toluene, dimethylacetamide (DMA), dimethylformamide (DMF), dimethylsulfoxide (DMSO), methylenechloride, dichloroethane, water, ethylacetate, acetonitrile; lower alcohols including isopropanol, methanol, ethanol, propanol and butanol; and ether solvents including tetrahydrofuran (THF), dioxane, ethylether and 1,2-dimethoxyethane, which can be used independently or together, and sec-butanol is more preferred herein.

After the reaction, the reaction mixture can be filtered with a filtration membrane and washed with an organic solvent. The solid compound 4 obtained after the concentration of the filtrate can be used in the next step without further purification.

Wherein, the reaction solvent is exemplified by toluene, dimethylacetamide (DMA), dimethylformamide (DMF), dimethylsulfoxide (DMSO), methylenechloride, dichloroethane, water, ethylacetate, acetonitrile; lower alcohols including isopropanol, methanol, ethanol, propanol and butanol; and ether solvents including tetrahydrofuran (THF), dioxane, ethylether and 1,2-dimethoxyethane, which can be used independently or together, and EtOAc (ethyl acetate) and MeOH (methanol) are more preferred herein.

Next step (step 2) is to prepare a compound represented by formula 1 by reacting the compound represented by formula 4 prepared in step 1 above in the presence of an acid.

As a preferable example of step 2, a compound represented by formula 3 was dissolved in dichloromethane, to which TFA (trifluoroacetic acid) was added at room temperature. After 4 hours of the reaction, the solvent was removed. Then, the concentrated mixture was dissolved in an organic solvent again. A base was added thereto at room temperature, followed by reaction for 14 hours.

Wherein, the base herein can be selected from the group consisting of such inorganic bases as cesium carbonate, sodium t-butoxide, potassium t-butoxide, sodium hydroxide, sodium carbonate, potassium carbonate and sodium hydride; and such organic bases as N,N-diaisopropylethylamine (DIPEA), 1,8-diazabicyclo[5.4.0]-7-undecene (DBU), pyridine and triethylamine. The selected base can be used in an equivalent amount or excess amount, alone or in combination. Herein, it is preferable to use saturated potassium carbonate.

Upon completion of the reaction, the reaction product was diluted in EtOAc (ethyl acetate), followed by washing with water and brine stepwise. The organic layer was dried over MgSO$_4$ (magnesium sulfate). Then, the reaction mixture was purified by prep-HPLC and as a result a solid compound 1 was obtained.

The present invention also provides a pharmaceutical composition comprising a compound represented by formula 1, an optical isomer thereof or a pharmaceutically acceptable salt thereof as an active ingredient for the prevention or treatment of protein kinase related disease.

Wherein, the protein kinase can be ABL, ALK, BUB1, CAMK1B, CAMK4, CAMKK1, CAMKK2, CHEK2m, CLK1, CLK2, CLK3, CLK4, CSNK1A1, CSNK1A1L, CSNK1D, CSNK1E, CSNK1G2, CSNK1G3, CSNK2A1, DAPK1, DAPK2, DAPK3, DCAMKL1, DRAK1, DRAK2, DYRK1A, DYRK1B, ERK5, FAK, FER, FES, FLT, GAK, HIPK1, HIPK2, HIPK3, HUNK, IGF1R, INSR, INSRR, IRAK4, JAK1, JNK1, JNK2, JNK3, KIT, LRRK2, LTK, MAP3K15, MAPKAPK2, MAPKAPK5, MEK3, MEK4, MEK5, MEK6, MKNK2, MYLK, MYO3B, NEK10, NIK, OSR1, PDGFRA, PHKG1, PHKG2, PIP5K1C, PIP5K2C, PLK1, PLK3, PLK4, PRKD1, PRKD2, PRKD3, PYK2, RIOK2, RIPK5, ROS1, RPS6KA4, RPS6KA5, RSK3, STK33, STK39, SYK, TAK1, TGFBR1, TNK1, TNK2, TSSK1B, TTK, YSK4 or ZAP70.

In addition, the protein kinase related disease can be one or more selected from the group consisting of cancer, degenerative brain disease and inflammatory disease.

The cancer can be one or more selected from the group consisting of brain cancer, brain tumor, benign astrocytoma, malignant astrocytoma, pituitary adenoma, meningioma, brain lymphoma, oligodendroglioma, intracranial carcinoma, ependymoma, brainstem tumor, head and neck tumor, larynx cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cell cancer, female urethral cancer and skin cancer. The degenerative brain disease can be one or more selected from the group consisting of Alzheimer's disease, Parkinson's disease, Lou Gehrig's disease, dementia, Huntington's disease, multiple sclerosis, proximal lateral sclerosis, apoplexy, stroke and mild cognitive impairment. In addition, the inflammatory disease can be one or more diseases selected from the group consisting of dermatitis, allergy, gastric ulcer, duodenal ulcer, hepatitis, esophagitis, gastritis, enteritis, pancreatitis, colitis, nephritis, systemic edema, local edema, arthritis, keratitis, bronchitis, pleurisy, peritonitis, spondylitis, inflammatory pain, Urethritis, cystitis, periodontitis and gingivitis.

The compound represented by formula 1 or the pharmaceutically acceptable salt thereof included in the pharmaceutical composition of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

To prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The effective dosage of the pharmaceutical composition comprising the compound represented by formula 1 or the pharmaceutically acceptable salt thereof as an active ingredient can be determined according to age, weight, gender, administration method, health condition, and severity of disease. The dosage is generally 0.1~1000 mg/day, and preferably 1~500 mg/day based on an adult patient weighing 70 kg, which can be administered once or several times a day at intervals of a certain time depending on the judgment of a doctor or a pharmacist.

The compound represented by formula 1, the optical isomer thereof or the pharmaceutically acceptable salt thereof according to the present invention was confirmed by Experimental Example 1 to be excellent in inhibiting LRRK2 kinase activity, confirmed by Experimental Example 2 to be excellent in inhibiting phosphorylation of NIH-3T3 cell line expressing LRRK2, and also confirmed by Experimental Example 3 to be excellent in inhibiting phosphorylation of NCC01 and 448T cell lines derived from brain tumor patients.

Particularly, as shown in FIG. 1, when the compound of the present invention was treated, the amount of P-LRRK2 was significantly reduced, compared with when the compound of the present invention was not treated. On the other hand, as shown in FIG. 2 and FIG. 3, when the compound of the present invention was treated to the cell line, P-LRRK2 was detected in a very small amount or not detected. Compared with when the compound of present invention was not treated, the amount of detectable P-LRRK2 was significantly low. The results above indicate that the compound of the present invention can inhibit phosphorylation of LRRK2 effectively.

Therefore, the pharmaceutical composition or the health functional food composition comprising the compound represented by formula 1, the optical isomer thereof or the pharmaceutically acceptable salt thereof as an active ingredient can be effectively used for the treatment or prevention of LRRK2 related disease.

The compound represented by formula 1 or the pharmaceutically acceptable salt thereof included in the pharmaceutical composition of the present invention can be administered orally or parenterally and be used in general forms of pharmaceutical formulation. That is, the composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds of the invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc.

The present invention also provides a health functional food composition comprising a compound represented by formula 1, an optical isomer thereof or a pharmaceutically acceptable salt thereof as an active ingredient for the prevention or amelioration of protein kinase related disease.

Wherein, the protein kinase related disease can be one or more diseases selected from the group consisting of cancer, degenerative brain disease and inflammatory disease.

The cancer can be one or more selected from the group consisting of brain cancer, brain tumor, benign astrocytoma, malignant astrocytoma, pituitary adenoma, meningioma, brain lymphoma, oligodendroglioma, intracranial carcinoma, ependymoma, brainstem tumor, head and neck tumor, larynx cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cell cancer, female urethral cancer and skin cancer. The degenerative brain disease can be one or more selected from the group consisting of Alzheimer's disease, Parkinson's disease, Lou Gehrig's disease, dementia, Huntington's disease, multiple sclerosis, proximal lateral sclerosis, apoplexy, stroke and mild cognitive impairment. In addition, the inflammatory disease can be one or more diseases selected from the group consisting of dermatitis, allergy, gastric ulcer, duodenal ulcer, hepatitis, esophagitis, gastritis, enteritis, pancreatitis, colitis, nephritis, systemic edema, local edema, arthritis, keratitis, bronchitis, pleurisy, peritonitis, spondylitis, inflammatory pain, Urethritis, cystitis, periodontitis and gingivitis.

The compound represented by formula 1 of the present invention can be used as a food additive. In that case, the compound represented by formula 1 of the present invention can be added as it is or as mixed with other food components according to the conventional method. The mixing ratio of active ingredients can be regulated according to the purpose of use (prevention or amelioration). In general, the compound of the present invention is preferably added to food or beverages by 0.1~90 weight part for the total weight of the food or beverages. However, if long term administration is required for health and hygiene or regulating health condition, the content can be lower than the above but higher content can be accepted as well since the compound of the present invention has been proved to be very safe.

The health beverage composition of the present invention can additionally include various flavors or natural carbohydrates, etc, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (thaumatin, *stevia* extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

The present invention also provides a method for preventing or treating protein kinase related disease, which comprises the step of administering a pharmaceutical composition or a health functional food composition comprising a compound represented by formula 1 or a pharmaceutically acceptable salt thereof as an active ingredient to a subject in need.

Wherein, the protein kinase related disease can be one or more diseases selected from the group consisting of cancer, degenerative brain disease and inflammatory disease.

The cancer can be one or more selected from the group consisting of brain cancer, brain tumor, benign astrocytoma, malignant astrocytoma, pituitary adenoma, meningioma, brain lymphoma, oligodendroglioma, intracranial carcinoma, ependymoma, brainstem tumor, head and neck tumor, larynx cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cell cancer, female urethral cancer and skin cancer. The degenerative brain disease can be one or more selected from the group consisting of Alzheimer's disease, Parkinson's disease, Lou Gehrig's disease, dementia, Huntington's disease, multiple sclerosis, proximal lateral sclerosis, apoplexy, stroke and mild cognitive impairment. In addition, the inflammatory disease can be one or more diseases selected from the group consisting of dermatitis, allergy, gastric ulcer, duodenal ulcer, hepatitis, esophagitis, gastritis, enteritis, pancreatitis, colitis, nephritis, systemic edema, local edema, arthritis, keratitis, bronchitis, pleurisy, peritonitis, spondylitis, inflammatory pain, Urethritis, cystitis, periodontitis and gingivitis.

In addition, the present invention provides a use of the pharmaceutical composition or the health functional food composition above comprising a compound represented by formula 1 or a pharmaceutically acceptable salt thereof as an active ingredient for the prevention or treatment of protein kinase related disease.

Wherein, the protein kinase related disease can be one or more diseases selected from the group consisting of cancer, degenerative brain disease and inflammatory disease.

The cancer can be one or more selected from the group consisting of brain cancer, brain tumor, benign astrocytoma, malignant astrocytoma, pituitary adenoma, meningioma, brain lymphoma, oligodendroglioma, intracranial carcinoma, ependymoma, brainstem tumor, head and neck tumor, larynx cancer, oropharyngeal cancer, nasal cavity/paranasal sinus cancer, nasopharyngeal cancer, salivary gland cancer, hypopharyngeal cancer, thyroid cancer, oral cancer, thoracic tumor, small cell lung cancer, non-small cell lung cancer, thymus cancer, mediastinal tumor, esophageal cancer, breast cancer, male breast cancer, abdominal tumor, stomach cancer, liver cancer, gallbladder cancer, biliary cancer, pancreatic cancer, small bowel cancer, colon cancer, rectal cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cell cancer, female urethral cancer and skin cancer. The degenerative brain disease can be one or more selected from the group consisting of Alzheimer's disease, Parkinson's disease, Lou Gehrig's disease, dementia, Huntington's disease, multiple sclerosis, proximal lateral sclerosis, apoplexy, stroke and mild cognitive impairment. In addition, the inflammatory disease can be one or more diseases selected from the group consisting of dermatitis, allergy, gastric ulcer, duodenal ulcer, hepatitis, esophagitis, gastritis, enteritis, pancreatitis, colitis, nephritis, systemic edema, local edema, arthritis, keratitis, bronchitis, pleurisy, peritonitis, spondylitis, inflammatory pain, Urethritis, cystitis, periodontitis and gingivitis.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Preparative Example 1-1> Preparation of 2-chloro-4-(methylamino)-7-((2-(trimethylsilyl)ethoxy)methyl)-7H-pyrrolo[2,3-d]pyrimidine-5-carbonitrile

[Reaction Formula 2]

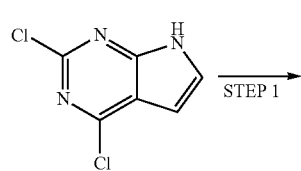

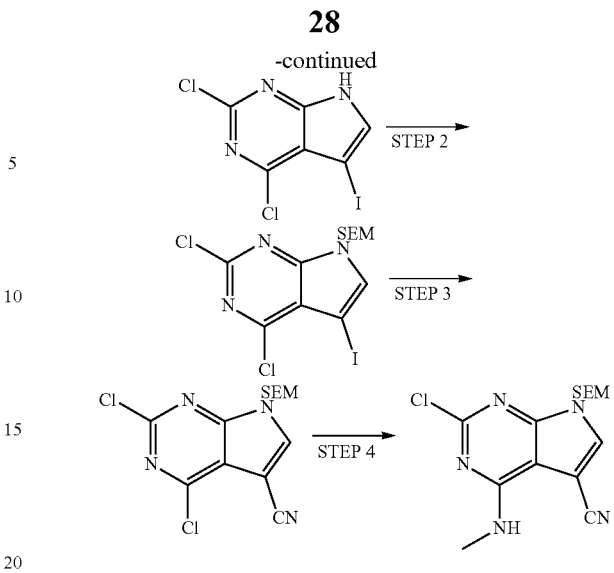

Step 1: 2,4-Dichloro-7H-pyrrolo[2,3-d]pyrimidine (1.0 e.q.) was dissolved in DMF, followed by lowering the temperature to −10° C. N-iodosuccinimide (1.1 e.q.) was added to the mixture, followed by raising the temperature to room temperature. Upon completion of the reaction, iced water was added thereto to induce precipitation. The formed precipitate was filtered and as a result a white target compound was obtained (yield: 100%).

Step 2: The 2,4-dichloro-5-iodo-7H-pyrrolo[2,3-d]pyrimidine (1.0 e.q.) prepared in step 1 was dissolved in DMF (0.5 M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over MgSO$_4$. The mixture was purified by MPCL (EtOAc:Hex) and as a result a white solid target compound was obtained (yield: 100%).

Step 3: Isopropyl magnesium chloride lithium chloride complex solution (5.0 e.q., 1.3 M in THF) was dissolved in THF (0.5 M), followed by lowering the temperature to −78° C., to which the 2,4-dichloro-5-iodo-7-((2-(trimethylsilyl)ethoxy)methyl)-7H-pyrrolo[2,3-d]pyrimidine (1.0 e.q.) solution dissolved in THF was slowly added. After 30 minutes of reaction, HOAc was added to the reaction mixture, followed by further reaction at −78° C. for 15 minutes. Water was added to the reactant, and organic materials were extracted with EtOAc (×3). The collected organic layer was washed with brine and the remaining water was dried over MgSO$_4$. The mixture was purified by MPCL (EtOAc:Hex) and as a result a yellow solid target compound was obtained (yield: 52%).

Step 4: 2,4-Dichloro-7-((2-(trimethylsilyl)ethoxy)methyl)-7H-pyrrolo[2,3-d]pyrimidine-5-carbonitrile (1.0 e.q.) was dissolved in THF, to which methylamine (1.0 e.q., 35 wt % in ethanol) and DIPEA (1.0 e.q.) were added thereto stepwise at room temperature. The mixture was stirred at room temperature for 18 hours. Upon completion of the reaction, water was added thereto, followed by extraction of organic materials with EtOAc (×3). The collected organic layer was dried over MgSO$_4$. The mixture was purified by MPCL (EtOAc:Hex) and as a result a yellow solid target compound (2-chloro-4-(methylamino)-7-((2-(trimethylsilyl)ethoxy)methyl)-7H-pyrrolo[2,3-d]pyrimidine-5-carbonitrile) was obtained (yield: 57%).

<Preparative Example 1-2> Preparation of 2-chloro-4-(ethylamino)-7-((2-(trimethylsilyl)ethoxy)methyl)-7H-pyrrolo[2,3-d]pyrimidine-5-carbonitrile 2-Chloro-4-(ethylamino)-7-((2-(trimethylsilyl)ethoxy)methyl)-7H-pyrrolo[2,3-d]pyrimidine-5-carbonitrile was prepared by the similar manner to the method described in <Preparative Example 1-1> (yield: 67%).

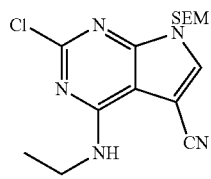 [SMILES: CCNc1nc(Cl)nc2c1c(C#N)cn2COCC[Si](C)(C)C]

<Preparative Example 1-3> Preparation of 2-chloro-4-(propylamino)-7-((2-(trimethylsilyl)ethoxy)methyl)-7H-pyrrolo[2,3-d]pyrimidine-5-carbonitrile 2-Chloro-4-(propylamino)-7-((2-(trimethylsilyl)ethoxy)methyl)-7H-pyrrolo[2,3-d]pyrimidine-5-carbonitrile was prepared by the similar manner to the method described in <Preparative Example 1-1> (yield: 45%).

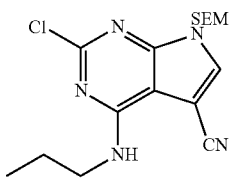 [SMILES: CCCNc1nc(Cl)nc2c1c(C#N)cn2COCC[Si](C)(C)C]

<Preparative Example 1-4> Preparation of 2-chloro-4-(cyclopropylamino)-7-((2-(trimethylsilyl)ethoxy)methyl)-7H-pyrrolo[2,3-d]pyrimidine-5-carbonitrile 2-Chloro-4-(cyclopropylamino)-7-((2-(trimethylsilyl)ethoxy)methyl)-7H-pyrrolo[2,3-d]pyrimidine-5-carbonitrile was prepared by the similar manner to the method described in <Preparative Example 1-1> (yield: 50%).

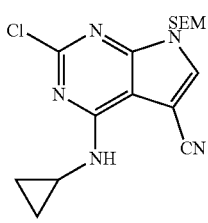 [SMILES: C[Si](C)(C)CCOCn1cc(C#N)c2c(NC3CC3)nc(Cl)nc21]

<Preparative Example 1-5> Preparation of 2-chloro-4-(1-methylcyclopropylamino)-7-((2-(trimethylsilyl)ethoxy)methyl)-7H-pyrrolo[2,3-d]pyrimidine-5-carbonitrile 2-Chloro-4-(1-methylcyclopropylamino)-7-((2-(trimethylsilyl)ethoxy)methyl)-7H-pyrrolo[2,3-d]pyrimidine-5-carbonitrile was prepared by the similar manner to the method described in <Preparative Example 1-1>.

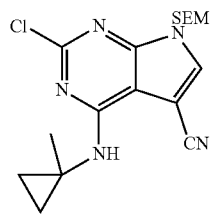 [SMILES: CC1(Nc2nc(Cl)nc3c2c(C#N)cn3COCC[Si](C)(C)C)CC1]

<Preparative Example 2-1> Preparation of 2-chloro-4-(tetrahydro-2H-pyran-4-yloxy)-7-((2-(trimethylsilyl)ethoxy)methyl)-7H-pyrrolo[2,3-d]pyrimidine-5-carbonitrile

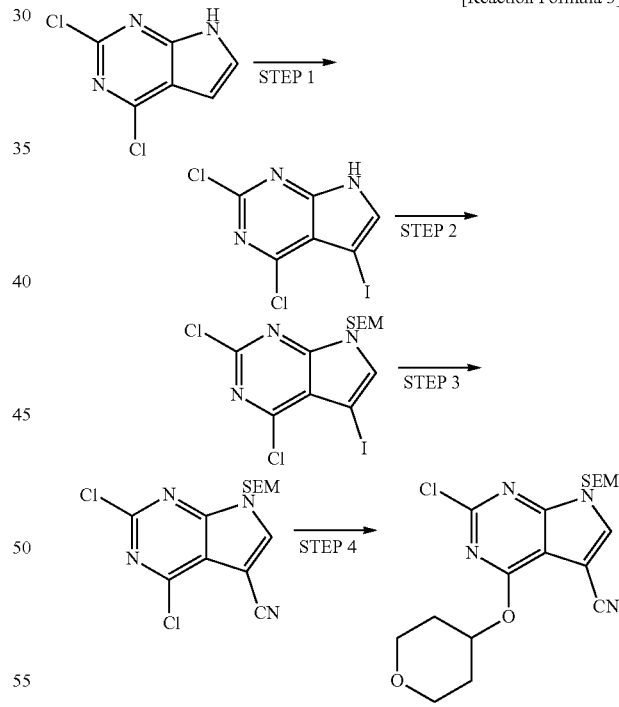

Step 1: 2,4-Dichloro-7H-pyrrolo[2,3-d]pyrimidine (1.0 e.q.) was dissolved in DMF, followed by lowering the temperature to −10° C. N-iodosuccinimide (1.1 e.q.) was added to the mixture, followed by raising the temperature to room temperature. Upon completion of the reaction, iced water was added thereto to induce precipitation. The formed precipitate was filtered and as a result a white target compound was obtained (yield: 100%).

Step 2: 2,4-Dichloro-5-iodo-7H-pyrrolo[2,3-d]pyrimidine (1.0 e.q.) prepared in step 1 was dissolved in DMF (0.5

M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over MgSO₄. The mixture was purified by MPCL (EtOAc:Hex) and as a result a white solid target compound was obtained (yield: 100%).

Step 3: Isopropyl magnesium chloride lithium chloride complex solution (5.0 e.q., 1.3 M in THF) was dissolved in THF (0.5 M), followed by lowering the temperature to −78° C., to which the 2,4-dichloro-5-iodo-7-((2-(trimethylsilyl)ethoxy)methyl)-7H-pyrrolo[2,3-d]pyrimidine (1.0 e.q.) solution dissolved in THF was slowly added. After 30 minutes of reaction, HOAc was added to the reaction mixture, followed by further reaction at −78° C. for 15 minutes. Water was added to the reactant, and organic materials were extracted with EtOAc (×3). The collected organic layer was washed with brine and the remaining water was dried over MgSO₄. The mixture was purified by MPCL (EtOAc:Hex) and as a result a yellow solid target compound was obtained (yield: 52%).

Step 4: Tetrahydro-2H-pyran-4-ol (1.8 e.q.) was dissolved in 1,4-dioxane (0.25 M), to which NaH (2.0 e.q.) was added at room temperature in the presence of nitrogen, followed by reaction for 5 minutes. Upon completion of the reaction, 2,4-dichloro-7-((2-(trimethylsilyl)ethoxy)methyl)-7H-pyrrolo[2,3-d]pyrimidine-5-carbonitrile (1.0 e.q.) dissolved in 1,4-dioxane was added slowly to the mixed solution above. The reactant was stirred at 100° C. for 18 hours. Upon completion of the reaction, the mixture was cooled down to room temperature and the remaining NaH activity was eliminated by adding sat. NH₄Cl. Organic materials were extracted with EtOAc (×3). The collected organic layer was dried over MgSO₄. The mixture was purified by MPCL (MeOH:CH₂Cl₂) and as a result a yellow oil target compound (2-chloro-4-(tetrahydro-2H-pyran-4-yloxy)-7-((2-(trimethylsilyl)ethoxy)methyl)-7H-pyrrolo[2,3-d]pyrimidine-5-carbonitrile) was obtained (yield: 33%).

<Preparative Example 2-2> Preparation of 2-chloro-4-(tetrahydrofuran-3-yloxy)-7-((2-(trimethylsilyl)ethoxy)methyl)-7H-pyrrolo[2,3-d]pyrimidine-5-carbonitrile 2-Chloro-4-(tetrahydrofuran-3-yloxy)-7-((2-(trimethylsilyl)ethoxy)methyl)-7H-pyrrolo[2,3-d]pyrimidine-5-carbonitrile was prepared by the similar manner to the method described in <Preparative Example 2-1> (yield: 87%).

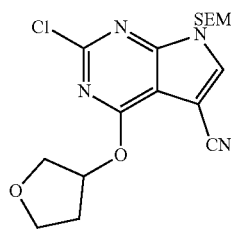 [SMILES: C[Si](C)(C)CCOCn1cc(C#N)c2c(OC3CCOC3)nc(Cl)nc21]

<Preparative Example 2-3> Preparation of 2-chloro-4-isoprofoxy-7-((2-(trimethylsilyl)ethoxy)methyl)-7H-pyrrolo[2,3-d]pyrimidine-5-carbonitrile 2-Chloro-4-isoprofoxy-7-((2-(trimethylsilyl)ethoxy)methyl)-7H-pyrrolo[2,3-d]pyrimidine-5-carbonitrile was prepared by the similar manner to the method described in <Preparative Example 2-1> (yield: 62%).

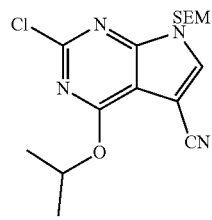 [SMILES: CC(C)Oc1nc(Cl)nc2c1c(C#N)cn2COCC[Si](C)(C)C]

<Preparative Example 2-4> Preparation of 2-chloro-4-(1-methylcyclopropoxy)-7-((2-(trimethylsilyl)ethoxy)methyl)-7H-pyrrolo[2,3-d]pyrimidine-5-carbonitrile 2-Chloro-4-(1-methylcyclopropoxy)-7-((2-(trimethylsilyl)ethoxy)methyl)-7H-pyrrolo[2,3-d]pyrimidine-5-carbonitrile was prepared by the similar manner to the method described in <Preparative Example 2-1>.

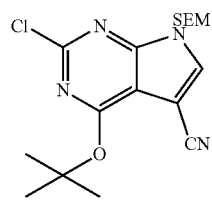 [SMILES: CC(C)(C)Oc1nc(Cl)nc2c1c(C#N)cn2COCC[Si](C)(C)C]

<Preparative Example 3-1> Preparation of 2-chloro-N-methyl-5-(trifluoromethyl)-7-((2-(trimethylsilyl)ethoxy)methyl)-7H-pyrrolo[2,3-d]pyrimidine-4-amine

[Reaction Formula 4]

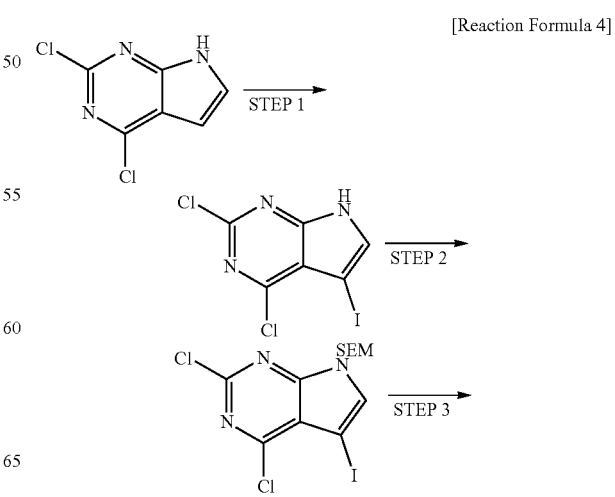

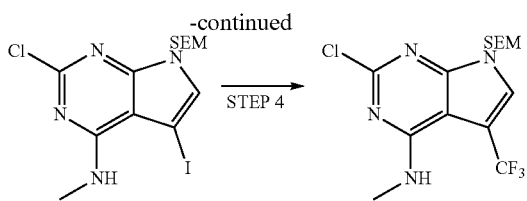

Step 1: 2,4-Dichloro-7H-pyrrolo[2,3-d]pyrimidine (1.0 e.q.) was dissolved in DMF, followed by lowering the temperature to −10° C. N-iodosuccinimide (1.1 e.q.) was added to the mixture, followed by raising the temperature to room temperature. Upon completion of the reaction, iced water was added thereto to induce precipitation. The formed precipitate was filtered and as a result a white target compound was obtained (yield: 100%).

Step 2: 2,4-Dichloro-5-iodo-7H-pyrrolo[2,3-d]pyrimidine (1.0 e.q.) prepared in step 1 was dissolved in DMF (0.5 M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over MgSO$_4$. The mixture was purified by MPCL (EtOAc:Hex) and as a result a white solid target compound was obtained (yield: 100%).

Step 3: 2,4-Dichloro-5-iodo-7-((2-(trimethylsilyl)ethoxy)methyl)-7H-pyrrolo[2,3-d]pyrimidine (1.0 e.q.) was dissolved in EtOH in a sealed tube, to which methylamine (3.5 wt % in EtOH) was added at room temperature, followed by stirring at 100° C. for 18 hours. Upon completion of the reaction, the solvent was removed and the resulting product was diluted in EtOAc, followed by washing with water. The organic layer was dried over MgSO$_4$. The mixture was purified by MPCL (EtOAc:Hex) and as a result a clear oil target compound was obtained (yield: 64%).

Step 4: A two-necked round-bottom flask was filled with nitrogen gas, to which CuI (5.0 e.q.) and KF (5.0 e.q.) were added. The temperature of the mixture was raised to 150° C., followed by stirring under reduced pressure for 2 hours. Upon completion of the reaction, the temperature was lowered to room temperature. Trimethyl(trifluoromethyl)silane (5.0 e.q.) dissolved in DMF/NMP (1:1) was added thereto using a syringe in the presence of nitrogen. After reacting for 30 minutes, 2-chloro-5-iodo-N-methyl-7-((2-(trimethylsilyl)ethoxy)methyl)-7H-pyrrolo[2,3-d]pyrimidine-4-amine (1.0 e.q.) dissolved in DMF/NMP (1:1) was added thereto using a syringe, followed by reaction at 45° C. for 48 hours. Upon completion of the reaction, water was added to the reactant to induce precipitation, and the formed precipitate was removed by filtration. Organic materials were extracted from the collected filtrate with EtOAc (×3). The collected organic layer was washed with brine and the remaining water was dried over Na$_2$SO$_4$. The mixture was purified by MPCL (EtOAc:Hex) and as a result a yellow solid target compound was obtained (yield: 65%).

<Preparative Example 3-2> Preparation of 2-chloro-N-ethyl-5-(trifluoromethyl)-7-((2-(trimethylsilyl)ethoxy)methyl)-7H-pyrrolo[2,3-d]pyrimidine-4-amine 2-Chloro-N-ethyl-5-(trifluoromethyl)-7-((2-(trimethylsilyl)ethoxy)methyl)-7H-pyrrolo[2,3-d]pyrimidine-4-amine was prepared by the similar manner to the method described in <Preparative Example 3-1>.

<Preparative Example 3-3> Preparation of 2-chloro-N-cyclopropyl-5-(trifluoromethyl)-7-((2-(trimethylsilyl)ethoxy)methyl)-7H-pyrrolo[2,3-d]pyrimidine-4-amine 2-Chloro-N-cyclopropyl-5-(trifluoromethyl)-7-((2-(trimethylsilyl)ethoxy)methyl)-7H-pyrrolo[2,3-d]pyrimidine-4-amine was prepared by the similar manner to the method described in <Preparative Example 3-1>.

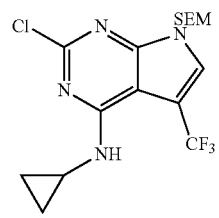 [SMILES: C[Si](C)(C)CCOCn1cc(C(F)(F)F)c2c(NC3CC3)nc(Cl)nc21]

<Preparative Example 3-4> Preparation of 2-chloro-N-(1-methylcyclopropyl)-5-(trifluoromethyl)-7-((2-(trimethylsilyl)ethoxy)methyl)-7H-pyrrolo[2,3-d]pyrimidine-4-amine 2-Chloro-N-(1-methylcyclopropyl)-5-(trifluoromethyl)-7-((2-(trimethylsilyl)ethoxy)methyl)-7H-pyrrolo[2,3-d]pyrimidine-4-amine was prepared by the similar manner to the method described in <Preparative Example 3-1>.

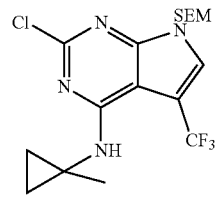 [SMILES: CC1(Nc2nc(Cl)nc3c2c(C(F)(F)F)cn3COCC[Si](C)(C)C)CC1]

<Preparative Example 4-1> Preparation of 2-chloro-4-(tetrahydrofuran-3-yloxy)-5-(trifluoromethyl)-7-((2-(trimethylsilyl)ethoxy)methyl)-7H-pyrrolo[2,3-d]pyrimidine

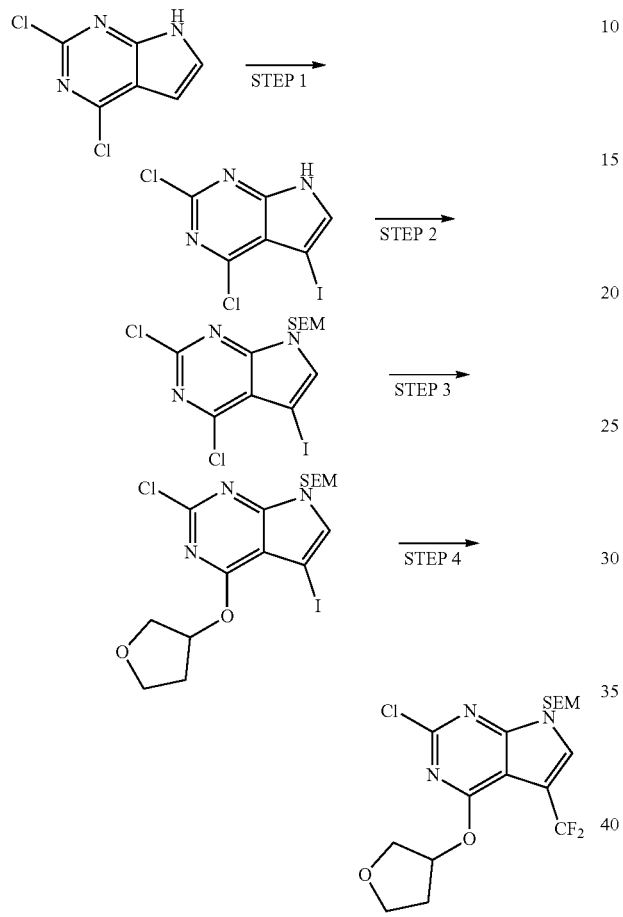

Step 1: 2,4-Dichloro-7H-pyrrolo[2,3-d]pyrimidine (1.0 e.q.) was dissolved in DMF, followed by lowering the temperature to −10° C. N-iodosuccinimide (1.1 e.q.) was added to the mixture, followed by raising the temperature to room temperature. Upon completion of the reaction, iced water was added thereto to induce precipitation. The formed precipitate was filtered and as a result a white target compound was obtained (yield: 100%).

Step 2: 2,4-Dichloro-5-iodo-7H-pyrrolo[2,3-d]pyrimidine (1.0 e.q.) prepared in step 1 was dissolved in DMF (0.5 M), followed by lowering the temperature to −78° C. NaH (1.5 e.q.) was added to the mixture above, followed by stirring for 5 minutes. Upon completion of the reaction, SEM-Cl (1.2 e.q.) was added thereto at −78° C. Then, the temperature of the reaction mixture was raised to room temperature, followed by stirring for 1 hour. Iced water was added to the reaction mixture above, followed by extracting organic materials with EtOAc (×3). The collected organic layer was washed with brine and the remaining water was dried over $MgSO_4$. The mixture was purified by MPCL (EtOAc:Hex) and as a result a white solid target compound was obtained (yield: 100%).

Step 3: Tetrahydrofuran-3-ol (2.0 e.q.) was dissolved in 1,4-dioxane (0.15 M) in the presence of nitrogen, followed by lowering the temperature to 0° C. NaH (1.1 e.q.) was added thereto, followed by stirring for 5 minutes, to which 2,4-dichloro-5-iodo-7-((2-(trimethylsilyl)ethoxy)methyl)-7H-pyrrolo[2,3-d]pyrimidine (1.0 e.q.) was added. The reactant was heated at 70° C., followed by stirring for 1 hour. Upon completion of the reaction, the mixture was cooled down to room temperature and the remaining NaH activity was eliminated by adding sat. $NH_4Cl$. Organic materials were extracted with EtOAc (×3). The collected organic layer was washed with brine, and the remaining water was dried over $MgSO_4$. The mixture was purified by MPCL (Hex:$CH_2Cl_2$) and as a result a white solid target compound was obtained (yield: 81%).

Step 4: A two-necked round-bottom flask was filled with nitrogen gas, to which CuI (5.0 e.q.) and KF (5.0 e.q.) were added. The temperature of the mixture was raised to 150° C., followed by stirring under reduced pressure for 2 hours. Upon completion of the reaction, the temperature was lowered to room temperature. Trimethyl(trifluoromethyl)silane (5.0 e.q.) dissolved in DMF/NMP (1:1) was added thereto using a syringe in the presence of nitrogen. After reacting for 30 minutes, 2-chloro-5-iodo-N-methyl-7-((2-(trimethylsilyl)ethoxy)methyl)-7H-pyrrolo[2,3-d]pyrimidine-4-amine (1.0 e.q.) dissolved in DMF/NMP (1:1) was added thereto using a syringe, followed by reaction at 45° C. for 48 hours. Upon completion of the reaction, water was added to the reactant to induce precipitation, and the formed precipitate was removed by filtration. Organic materials were extracted from the collected filtrate with EtOAc (×3). The collected organic layer was washed with brine and the remaining water was dried over $Na_2SO_4$. The mixture was purified by MPCL (EtOAc:Hex) and as a result a yellow solid target compound (2-chloro-4-(tetrahydrofuran-3-yloxy)-5-(trifluoromethyl)-7-((2-(trimethylsilyl)ethoxy)methyl)-7H-pyrrolo[2,3-d]pyrimidine) was obtained (yield: 65%).

<Example 1> Preparation 1 of the Compound of the Invention

The pyrrolo-pyrimidine derivative for the treatment of Parkinson's disease and brain cancer of the present invention was prepared according to the following reaction formula 6.

[Reaction Formula 6]

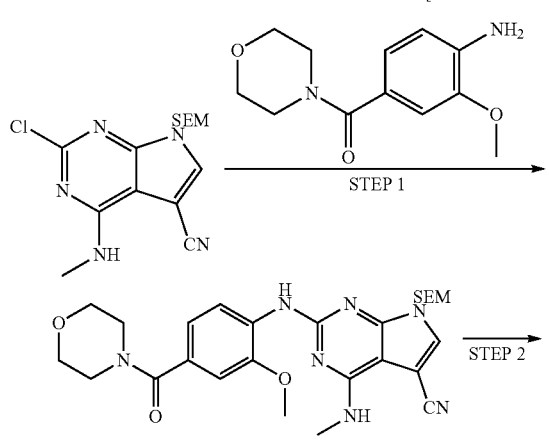

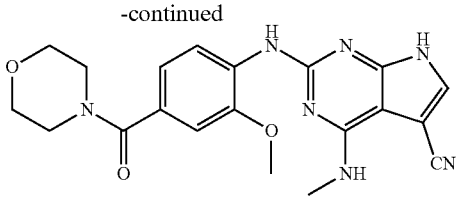

Step 1: The compound of <Preparative Example 1-1> (1.0 e.q.), (4-amino-3-methoxyphenyl)(morpholino)methanone (1.0 e.q.) and $K_2CO_3$ (5.0 e.q.) were dissolved in sec-BuOH (0.1 M), followed by ultrasonication for 1 minute to eliminate gas. $Pd_2(dba)_3$ (0.1 e.q.) and Xphos (0.1 e.q.) were added to the reaction mixture at 100° C., followed by reaction for 2 hours. Upon completion of the reaction, the reaction mixture was filtered with celite and then washed with EtOAc and MeOH. The obtained filtrate was concentrated and as a result a yellow solid target compound was obtained. The obtained target compound was used in the next step without any additional purification.

Step 2: 2-((2-Methoxy-4-(morpholine-4-carbonyl)phenyl)amino)-4-(methylamino)-7-((2-(trimethylsilyl)ethoxy)methyl)-7H-pyrrolo[2,3-d]pyrimidine-5-carbonitrile (1.0 e.q.) was dissolved in $CH_2Cl_2$ (0.05 M), to which TFA (100 e.q.) was added at room temperature. After 4 hours of the reaction, the solvent was eliminated. The concentrated reaction mixture was dissolved in THF (0.03 M) again, to which sat. $Na_2CO_3$ (0.03 M) was added at room temperature, followed by reaction for 14 hours. Upon completion of the reaction, the resulting product was diluted in EtOAc, and then washed with water and brine stepwise. The organic layer was dried over $MgSO_4$. The mixture was purified by prep-HPLC and as a result a yellow solid target compound (2-((2-methoxy-4-(morpholine-4-carbonyl)phenyl)amino)-4-(methylamino)-7H-pyrrolo[2,3-d]pyrimidine-5-carbonitrile) was obtained (yield: 91%).

<Example 2>~<Example 137> Preparation 2 of the Compound of the Invention

The pyrrolo-pyrimidine derivatives of the present invention for the treatment of Parkinson's disease and brain cancer were prepared by the similar manner to the method described in Example 1 using the compounds of <Preparative Example 1-1>~<Preparative Example 1-4>, <Preparative Example 2-1>~<Preparative Example 2-4>, <Preparative Example 3-1>~<Preparative Example 3-4> and <Preparative Example 4-1>. Chemical structural formulas of the compounds of Examples 1~137 are shown in Tables 1~4 below. Compound names, $H^1$ NMR data, yields and HPLC results are summarized in Table 5 below.

TABLE 1

| Example | Chemical Structure |
|---|---|
| 1 | 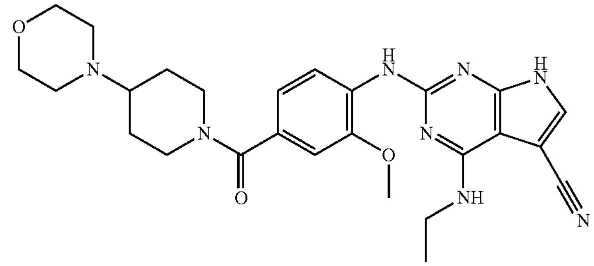 [SMILES: CCNc1nc(Nc2ccc(C(=O)N3CCC(N4CCOCC4)CC3)cc2OC)nc2[nH]cc(C#N)c12] |
| 2 | 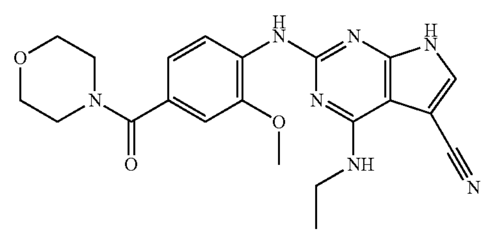 [SMILES: CCNc1nc(Nc2ccc(C(=O)N3CCOCC3)cc2OC)nc2[nH]cc(C#N)c12] |
| 3 | 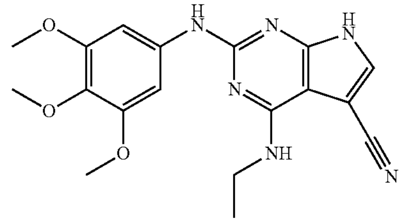 [SMILES: CCNc1nc(Nc2cc(OC)c(OC)c(OC)c2)nc2[nH]cc(C#N)c12] |

TABLE 1-continued

| Example | Chemical Structure |
|---|---|
| 4 | 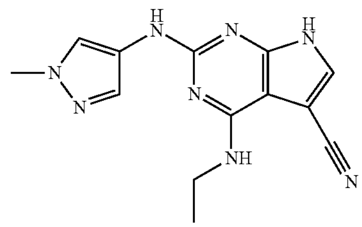 [SMILES: CCNc1nc(Nc2cnn(C)c2)nc2[nH]cc(C#N)c12] |
| 5 | 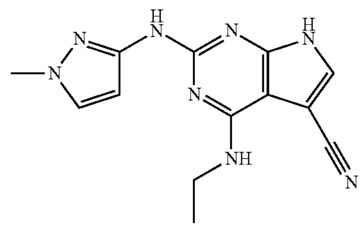 [SMILES: CCNc1nc(Nc2ccn(C)n2)nc2[nH]cc(C#N)c12] |
| 6 | 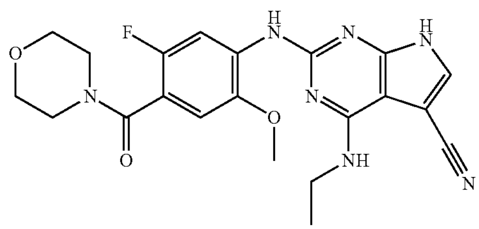 [SMILES: CCNc1nc(Nc2cc(F)c(C(=O)N3CCOCC3)cc2OC)nc2[nH]cc(C#N)c12] |
| 7 | 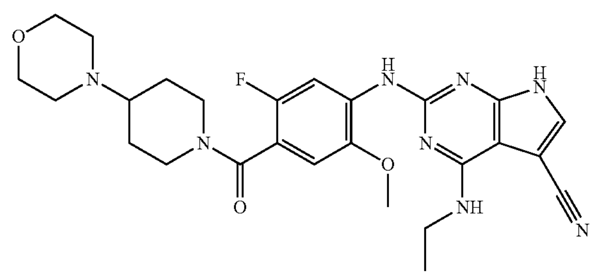 [SMILES: CCNc1nc(Nc2cc(F)c(C(=O)N3CCC(N4CCOCC4)CC3)cc2OC)nc2[nH]cc(C#N)c12] |
| 8 | 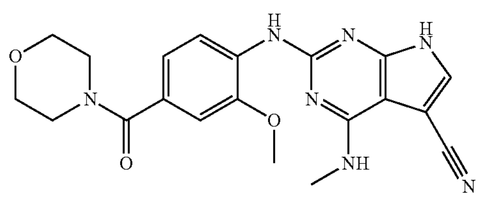 [SMILES: CNc1nc(Nc2ccc(C(=O)N3CCOCC3)cc2OC)nc2[nH]cc(C#N)c12] |
| 9 | 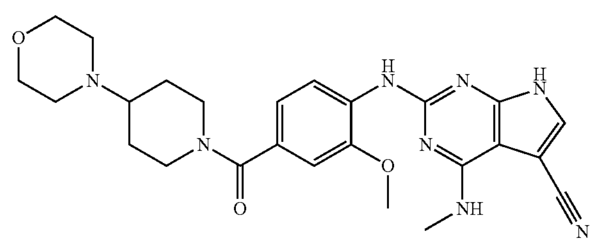 [SMILES: CNc1nc(Nc2ccc(C(=O)N3CCC(N4CCOCC4)CC3)cc2OC)nc2[nH]cc(C#N)c12] |
| 10 | 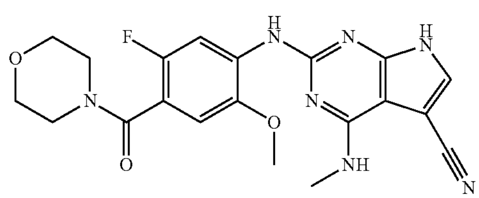 [SMILES: CNc1nc(Nc2cc(F)c(C(=O)N3CCOCC3)cc2OC)nc2[nH]cc(C#N)c12] |

TABLE 1-continued
| Example | Chemical Structure |
|---|---|
| 11 | 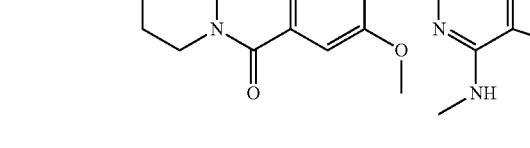 |
| 12 | 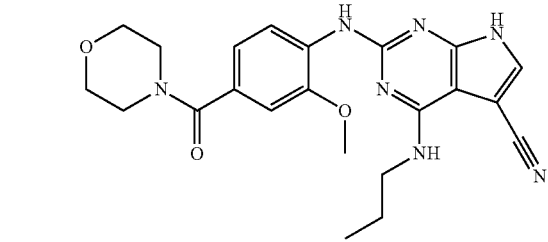 [SMILES: CCCNc1nc(Nc2ccc(C(=O)N3CCOCC3)cc2OC)nc2[nH]cc(C#N)c12] |
| 13 | 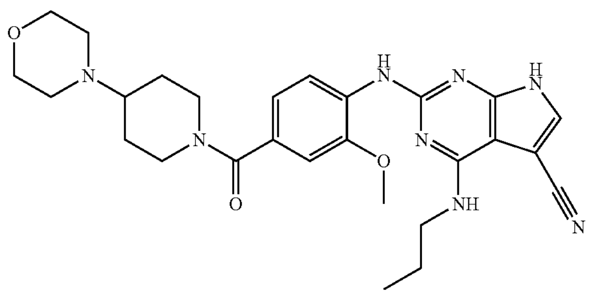 [SMILES: CCCNc1nc(Nc2ccc(C(=O)N3CCC(N4CCOCC4)CC3)cc2OC)nc2[nH]cc(C#N)c12] |
| 14 | 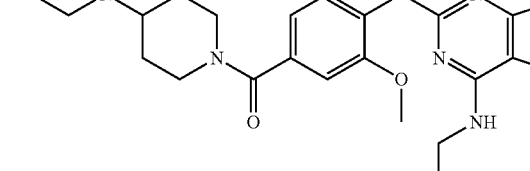 |
| 15 | 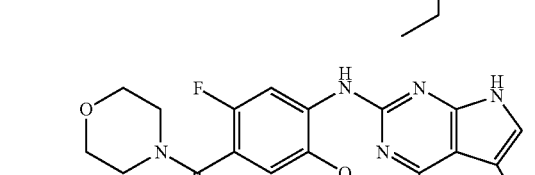 |
| 16 | 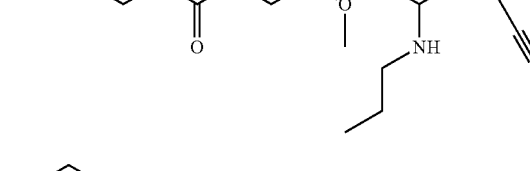 |

TABLE 1-continued
| Example | Chemical Structure |
|---|---|
| 17 | 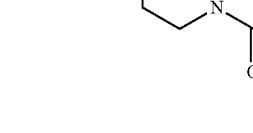 |
| 18 | 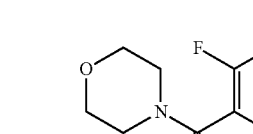 |
| 19 | 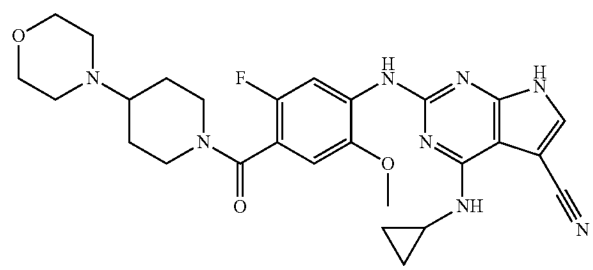 [SMILES: COc1cc(C(=O)N2CCC(N3CCOCC3)CC2)c(F)cc1Nc1nc(NC2CC2)c2c(C#N)c[nH]c2n1] |
| 20 | 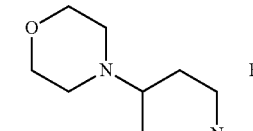 |
| 21 | 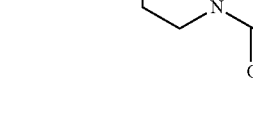 |
| 22 | 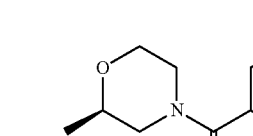 |
| 23 | 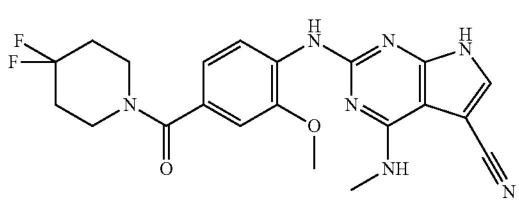 [SMILES: CNc1nc(Nc2ccc(C(=O)N3CCC(F)(F)CC3)cc2OC)nc2[nH]cc(C#N)c12] |

TABLE 1-continued

| Example | Chemical Structure |
|---|---|
| 24 | 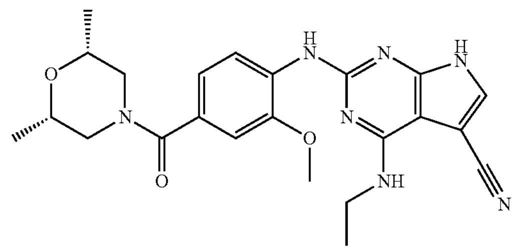 [SMILES: CCNc1nc(Nc2ccc(C(=O)N3C[C@@H](C)O[C@@H](C)C3)cc2OC)nc2[nH]cc(C#N)c12] |
| 25 | 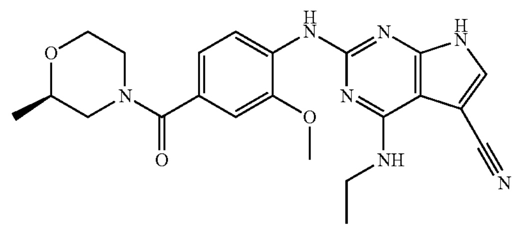 [SMILES: CCNc1nc(Nc2ccc(C(=O)N3CCO[C@H](C)C3)cc2OC)nc2[nH]cc(C#N)c12] |
| 26 | 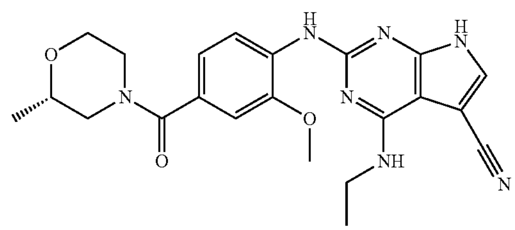 [SMILES: CCNc1nc(Nc2ccc(C(=O)N3CCO[C@@H](C)C3)cc2OC)nc2[nH]cc(C#N)c12] |
| 27 | 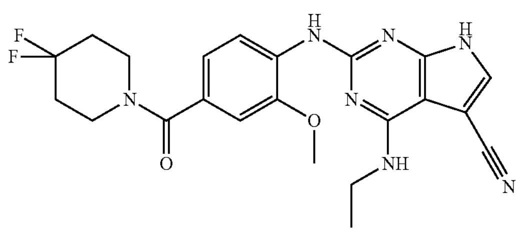 [SMILES: CCNc1nc(Nc2ccc(C(=O)N3CCC(F)(F)CC3)cc2OC)nc2[nH]cc(C#N)c12] |
| 28 | 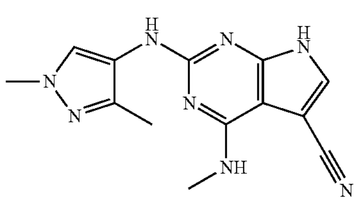 [SMILES: CNc1nc(Nc2cn(C)nc2C)nc2[nH]cc(C#N)c12] |
| 29 | 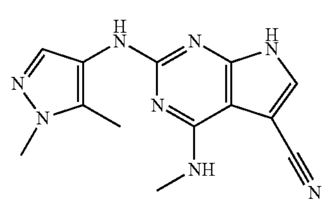 [SMILES: CNc1nc(Nc2cnn(C)c2C)nc2[nH]cc(C#N)c12] |
| 30 | 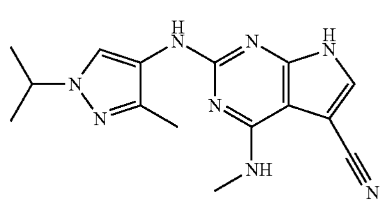 [SMILES: CNc1nc(Nc2cn(C(C)C)nc2C)nc2[nH]cc(C#N)c12] |

TABLE 1-continued

| Example | Chemical Structure |
|---|---|
| 31 | 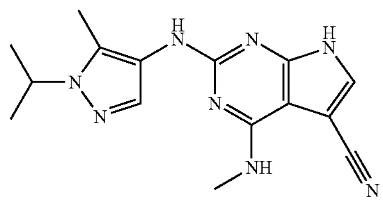 [SMILES: CNc1nc(Nc2cnn(C(C)C)c2C)nc2[nH]cc(C#N)c12] |
| 32 | 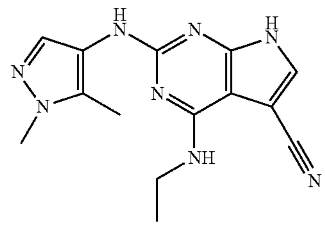 [SMILES: CCNc1nc(Nc2cnn(C)c2C)nc2[nH]cc(C#N)c12] |
| 33 | 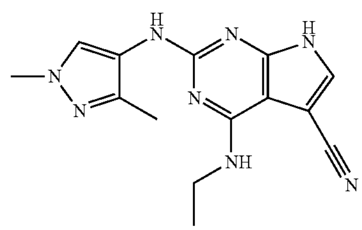 [SMILES: CCNc1nc(Nc2cn(C)nc2C)nc2[nH]cc(C#N)c12] |
| 34 | 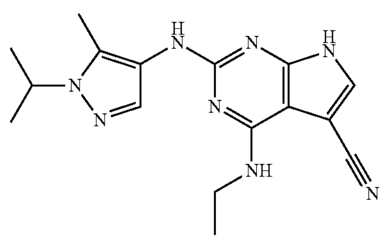 [SMILES: CCNc1nc(Nc2cnn(C(C)C)c2C)nc2[nH]cc(C#N)c12] |
| 35 | 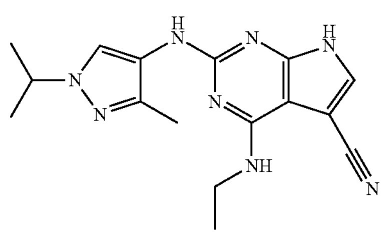 [SMILES: CCNc1nc(Nc2cn(C(C)C)nc2C)nc2[nH]cc(C#N)c12] |
| 36 | 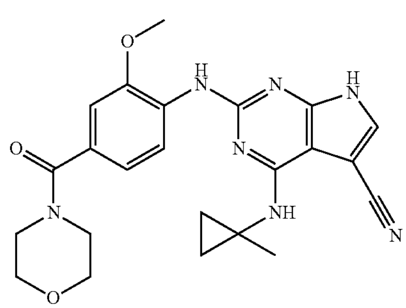 [SMILES: COc1cc(C(=O)N2CCOCC2)ccc1Nc1nc(NC2(C)CC2)c2c(C#N)c[nH]c2n1] |

TABLE 1-continued
| Example | Chemical Structure |
|---|---|
| 37 | 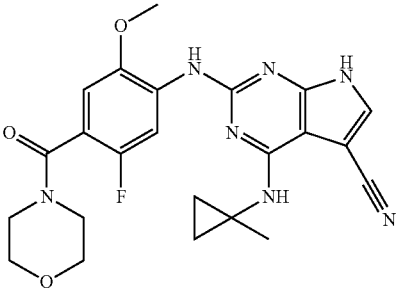 [SMILES: COc1cc(C(=O)N2CCOCC2)c(F)cc1Nc1nc(NC2(C)CC2)c2c(C#N)c[nH]c2n1] |
| 38 | 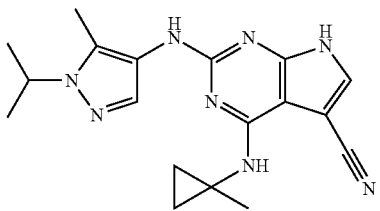 [SMILES: Cc1c(Nc2nc(NC3(C)CC3)c3c(C#N)c[nH]c3n2)cnn1C(C)C] |
| 39 | 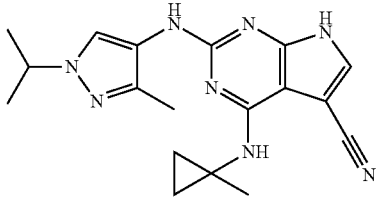 [SMILES: Cc1nn(C(C)C)cc1Nc1nc(NC2(C)CC2)c2c(C#N)c[nH]c2n1] |
| 40 | 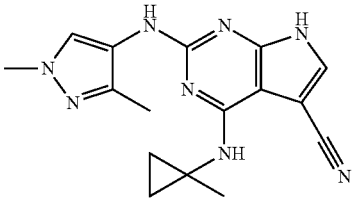 [SMILES: Cc1nn(C)cc1Nc1nc(NC2(C)CC2)c2c(C#N)c[nH]c2n1] |
TABLE 2
| Example | Chemical Structure |
|---|---|
| 41 | 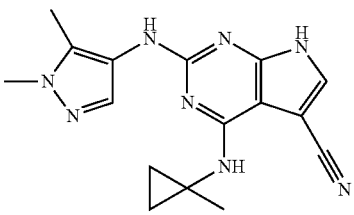 [SMILES: Cc1c(Nc2nc(NC3(C)CC3)c3c(C#N)c[nH]c3n2)cnn1C] |
| 42 | 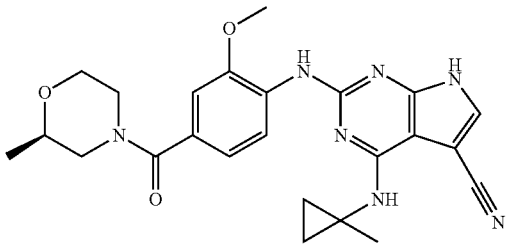 [SMILES: COc1cc(C(=O)N2CCO[C@H](C)C2)ccc1Nc1nc(NC2(C)CC2)c2c(C#N)c[nH]c2n1] |

TABLE 2-continued

| Example | Chemical Structure |
|---|---|
| 43 | 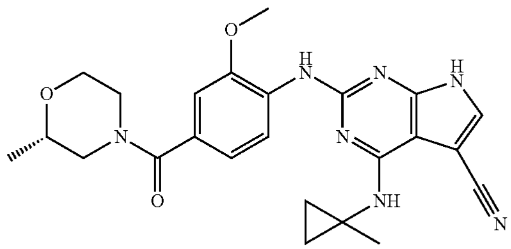 |
| 44 | 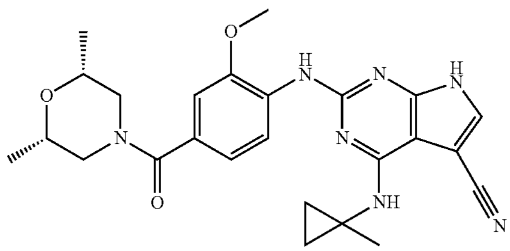 |
| 45 | 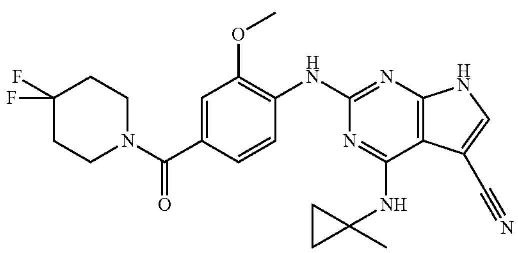 [SMILES: COc1cc(C(=O)N2CCC(F)(F)CC2)ccc1Nc1nc(NC2(C)CC2)c2c(C#N)c[nH]c2n1] |
| 46 | 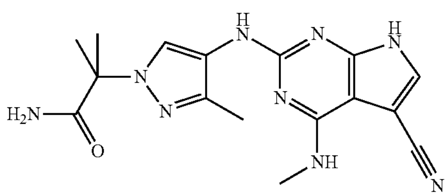 [SMILES: CNc1nc(Nc2cn(C(C)(C)C(N)=O)nc2C)nc2[nH]cc(C#N)c12] |
| 47 | 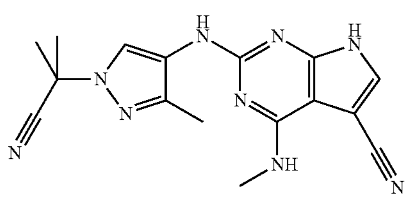 [SMILES: CNc1nc(Nc2cn(C(C)(C)C#N)nc2C)nc2[nH]cc(C#N)c12] |
| 48 | 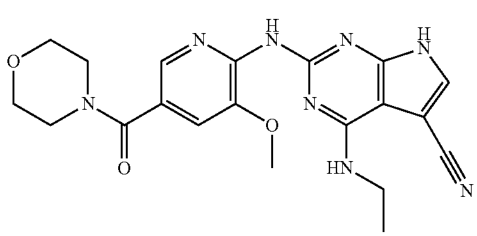 [SMILES: CCNc1nc(Nc2ncc(C(=O)N3CCOCC3)cc2OC)nc2[nH]cc(C#N)c12] |
| 49 | 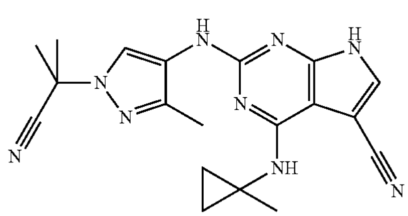 [SMILES: Cc1nn(C(C)(C)C#N)cc1Nc1nc(NC2(C)CC2)c2c(C#N)c[nH]c2n1] |

TABLE 2-continued

| Example | Chemical Structure |
|---------|-------------------|
| 50 | 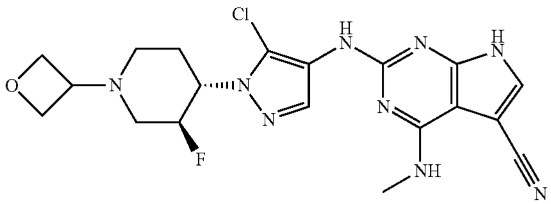 [SMILES: CNc1nc(Nc2cnn([C@H]3CCN(C4COC4)C[C@@H]3F)c2Cl)nc2[nH]cc(C#N)c12] |
| 51 | 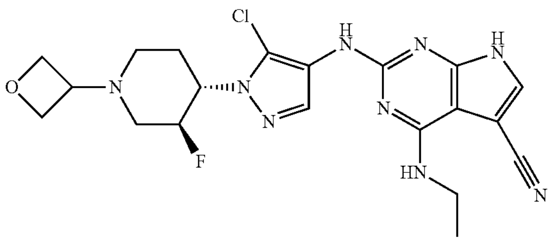 [SMILES: CCNc1nc(Nc2cnn([C@H]3CCN(C4COC4)C[C@@H]3F)c2Cl)nc2[nH]cc(C#N)c12] |
| 52 | 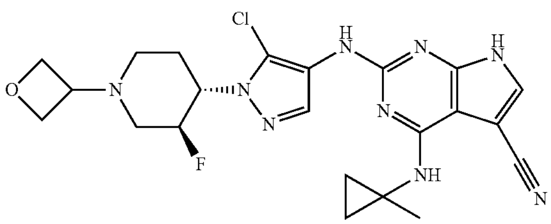 [SMILES: CC1(Nc2nc(Nc3cnn([C@H]4CCN(C5COC5)C[C@@H]4F)c3Cl)nc3[nH]cc(C#N)c23)CC1] |
| 53 | 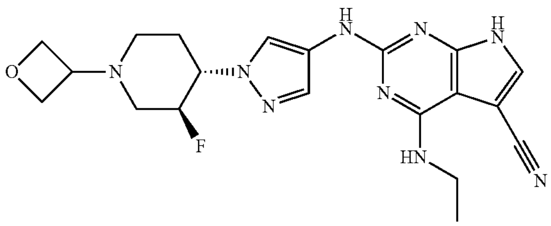 [SMILES: CCNc1nc(Nc2cnn([C@H]3CCN(C4COC4)C[C@@H]3F)c2)nc2[nH]cc(C#N)c12] |
| 54 | 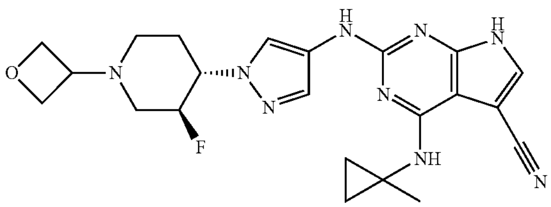 [SMILES: CC1(Nc2nc(Nc3cnn([C@H]4CCN(C5COC5)C[C@@H]4F)c3)nc3[nH]cc(C#N)c23)CC1] |
| 55 | 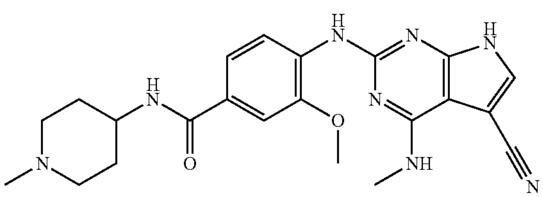 [SMILES: CNc1nc(Nc2ccc(C(=O)NC3CCN(C)CC3)cc2OC)nc2[nH]cc(C#N)c12] |
| 56 | 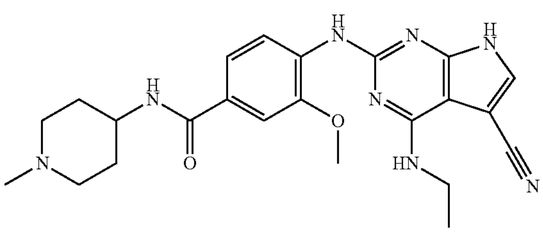 [SMILES: CCNc1nc(Nc2ccc(C(=O)NC3CCN(C)CC3)cc2OC)nc2[nH]cc(C#N)c12] |

TABLE 2-continued
| Example | Chemical Structure |
|---|---|
| 57 | 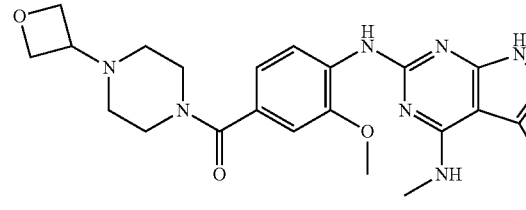 |
| 58 | 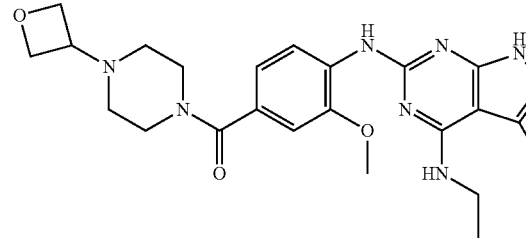 |
| 59 | 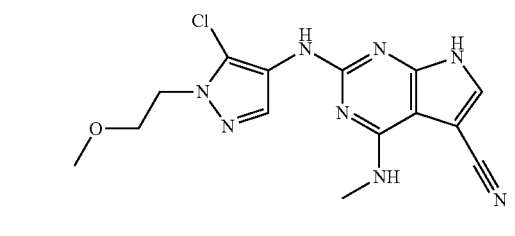 [SMILES: CNc1nc(Nc2cnn(CCOC)c2Cl)nc2[nH]cc(C#N)c12] |
| 60 | 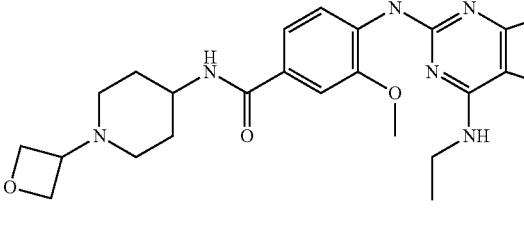 |
| 61 | 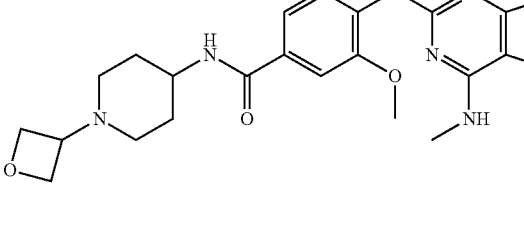 |
| 62 | 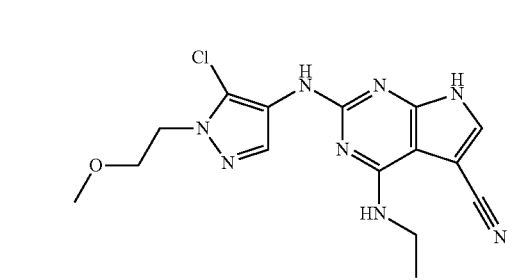 [SMILES: CCNc1nc(Nc2cnn(CCOC)c2Cl)nc2[nH]cc(C#N)c12] |

TABLE 2-continued

| Example | Chemical Structure |
|---|---|
| 63 | 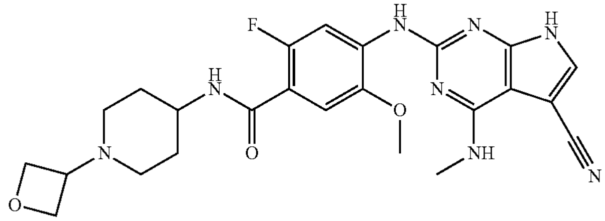 [SMILES: CNc1nc(Nc2cc(F)c(C(=O)NC3CCN(C4COC4)CC3)cc2OC)nc2[nH]cc(C#N)c12] |
| 64 | 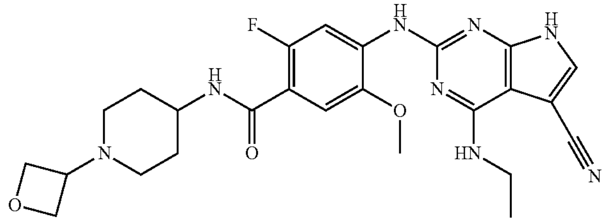 [SMILES: CCNc1nc(Nc2cc(F)c(C(=O)NC3CCN(C4COC4)CC3)cc2OC)nc2[nH]cc(C#N)c12] |
| 65 | 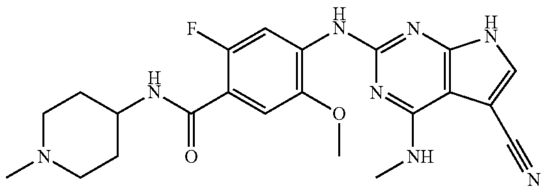 [SMILES: CNc1nc(Nc2cc(F)c(C(=O)NC3CCN(C)CC3)cc2OC)nc2[nH]cc(C#N)c12] |
| 66 | 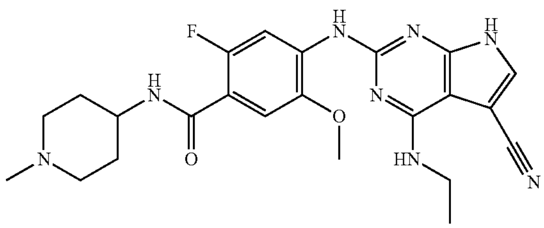 [SMILES: CCNc1nc(Nc2cc(F)c(C(=O)NC3CCN(C)CC3)cc2OC)nc2[nH]cc(C#N)c12] |
| 67 | 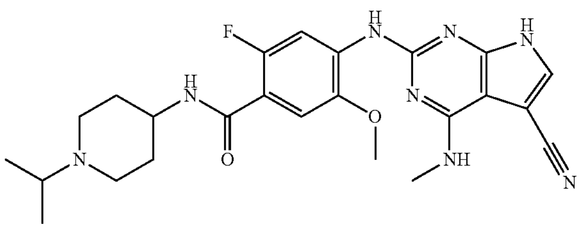 [SMILES: CNc1nc(Nc2cc(F)c(C(=O)NC3CCN(C(C)C)CC3)cc2OC)nc2[nH]cc(C#N)c12] |
| 68 | 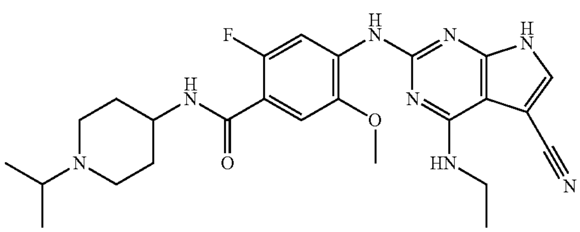 [SMILES: CCNc1nc(Nc2cc(F)c(C(=O)NC3CCN(C(C)C)CC3)cc2OC)nc2[nH]cc(C#N)c12] |
| 69 | 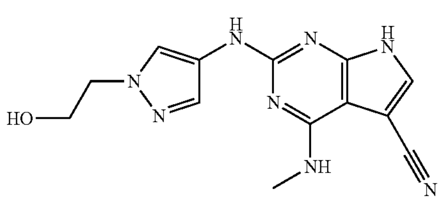 [SMILES: CNc1nc(Nc2cnn(CCO)c2)nc2[nH]cc(C#N)c12] |

TABLE 2-continued
| Example | Chemical Structure |
|---|---|
| 70 | 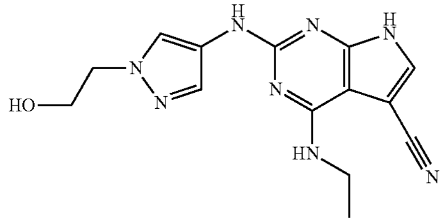 [SMILES: CCNc1nc(Nc2cnn(CCO)c2)nc2[nH]cc(C#N)c12] |
| 71 | 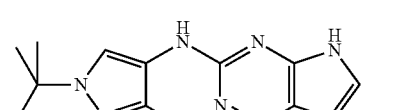 |
| 72 | 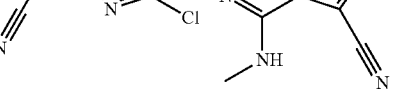 |
| 73 | 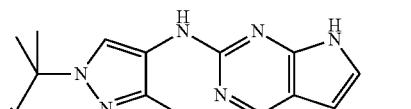 |
| 74 | 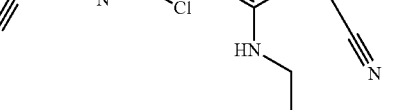 |
| 75 | 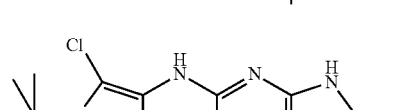 |
| 76 | 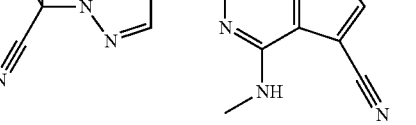 |

TABLE 2-continued

| Example | Chemical Structure |
|---|---|
| 77 | 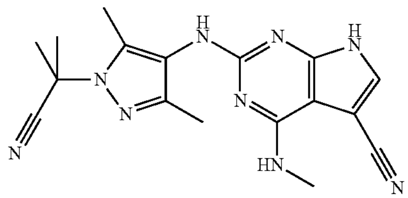 [SMILES: CNc1nc(Nc2c(C)nn(C(C)(C)C#N)c2C)nc2[nH]cc(C#N)c12] |
| 78 | 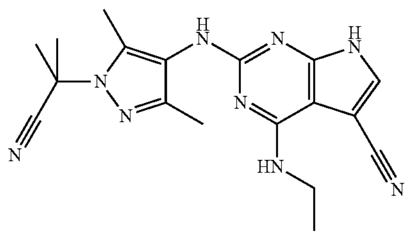 [SMILES: CCNc1nc(Nc2c(C)nn(C(C)(C)C#N)c2C)nc2[nH]cc(C#N)c12] |
| 79 | 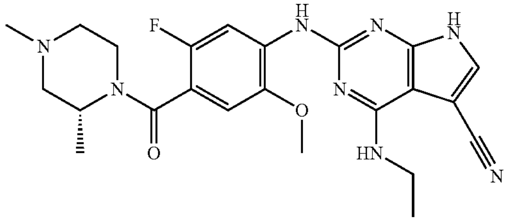 [SMILES: CCNc1nc(Nc2cc(F)c(C(=O)N3CCN(C)C[C@H]3C)cc2OC)nc2[nH]cc(C#N)c12] |
| 80 | 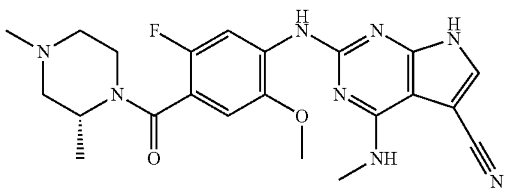 [SMILES: CNc1nc(Nc2cc(F)c(C(=O)N3CCN(C)C[C@H]3C)cc2OC)nc2[nH]cc(C#N)c12] |

TABLE 3

| Example | Chemical Structure |
|---|---|
| 81 | 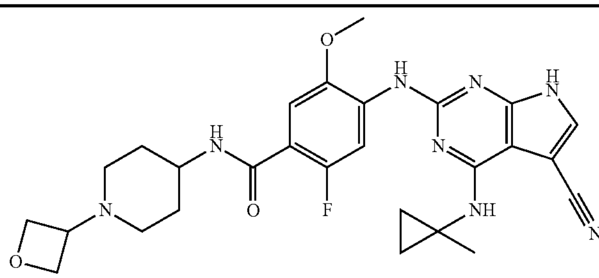 |
| 82 | 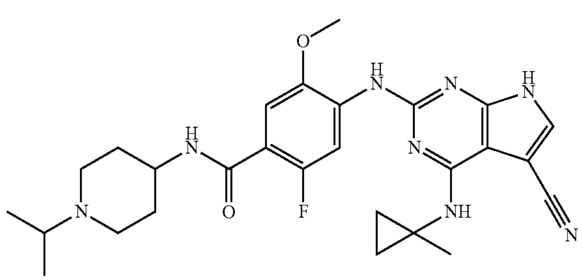 [SMILES: COc1cc(C(=O)NC2CCN(C(C)C)CC2)c(F)cc1Nc1nc(NC2(C)CC2)c2c(C#N)c[nH]c2n1] |

TABLE 3-continued

| Example | Chemical Structure |
|---|---|
| 83 | 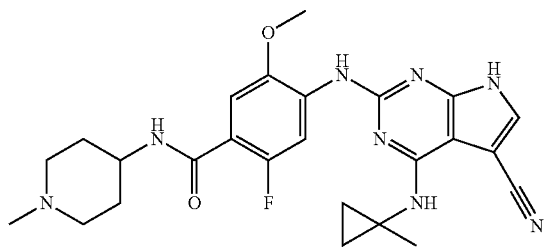 [SMILES: COc1cc(C(=O)NC2CCN(C)CC2)c(F)cc1Nc1nc(NC2(C)CC2)c2c(C#N)c[nH]c2n1] |
| 84 | 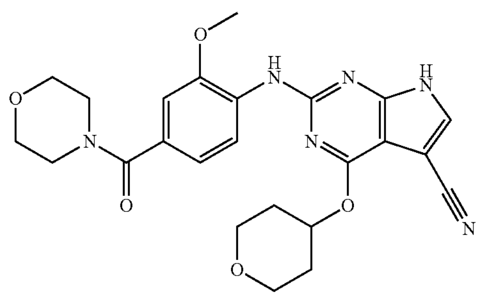 [SMILES: COc1cc(C(=O)N2CCOCC2)ccc1Nc1nc(OC2CCOCC2)c2c(C#N)c[nH]c2n1] |
| 85 | 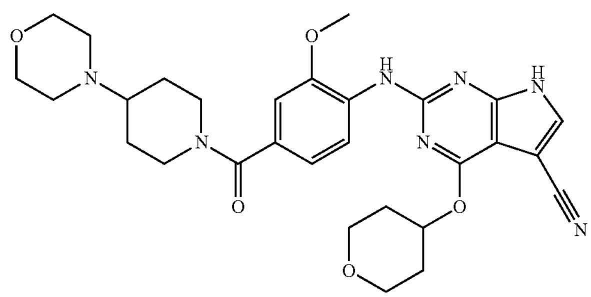 [SMILES: COc1cc(C(=O)N2CCC(N3CCOCC3)CC2)ccc1Nc1nc(OC2CCOCC2)c2c(C#N)c[nH]c2n1] |
| 86 | 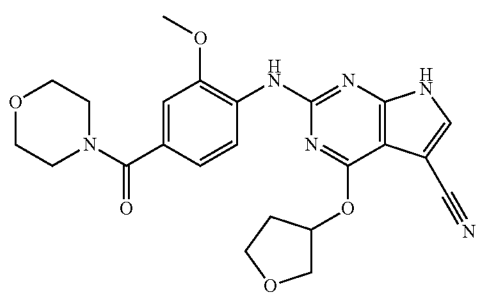 [SMILES: COc1cc(C(=O)N2CCOCC2)ccc1Nc1nc(OC2CCOC2)c2c(C#N)c[nH]c2n1] |
| 87 | 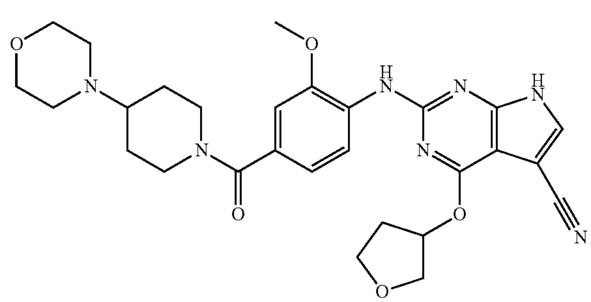 [SMILES: COc1cc(C(=O)N2CCC(N3CCOCC3)CC2)ccc1Nc1nc(OC2CCOC2)c2c(C#N)c[nH]c2n1] |

TABLE 3-continued
| Example | Chemical Structure |
|---------|--------------------|
| 88 | 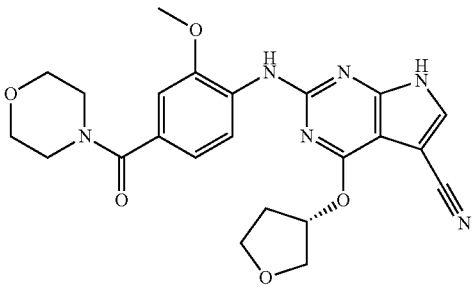 |
| 89 | 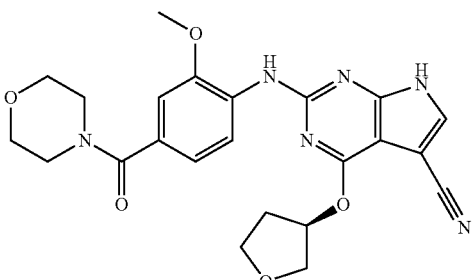 |
| 90 | 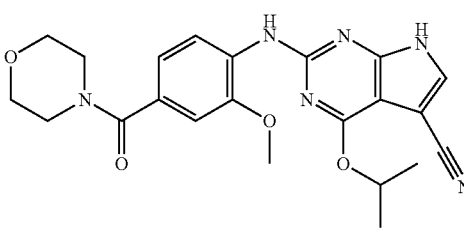 |
| 91 | 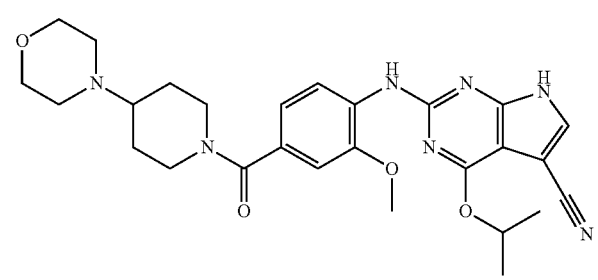 [SMILES: COc1cc(C(=O)N2CCC(N3CCOCC3)CC2)ccc1Nc1nc(OC(C)C)c2c(C#N)c[nH]c2n1] |
| 92 | 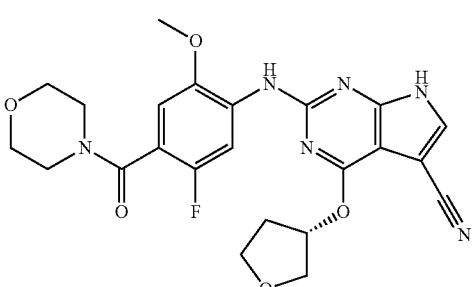 |

TABLE 3-continued
| Example | Chemical Structure |
|---------|---------------------|
| 93 | 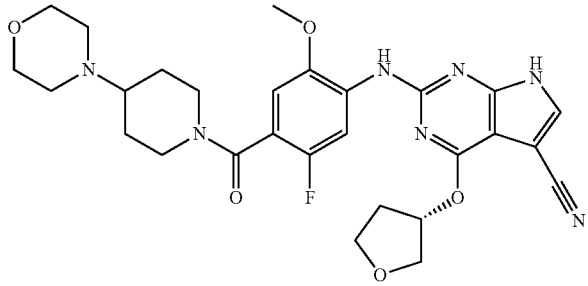 [SMILES: COc1cc(C(=O)N2CCC(N3CCOCC3)CC2)c(F)cc1Nc1nc(O[C@H]2CCOC2)c2c(C#N)c[nH]c2n1] |
| 94 | 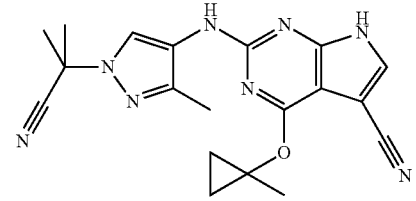 |
| 95 | 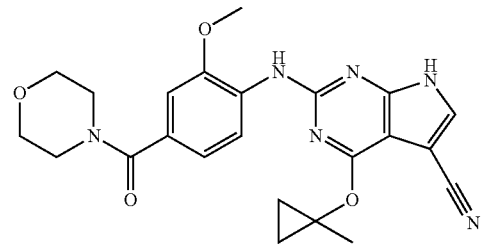 [SMILES: COc1cc(C(=O)N2CCOCC2)ccc1Nc1nc(OC2(C)CC2)c2c(C#N)c[nH]c2n1] |
| 96 | 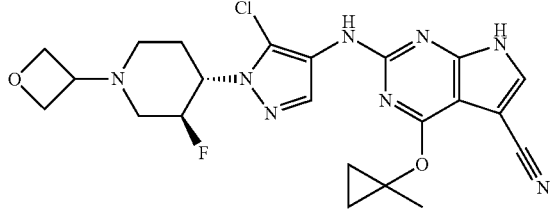 [SMILES: CC1(Oc2nc(Nc3cnn([C@H]4CCN(C5COC5)C[C@@H]4F)c3Cl)nc3[nH]cc(C#N)c23)CC1] |
| 97 | 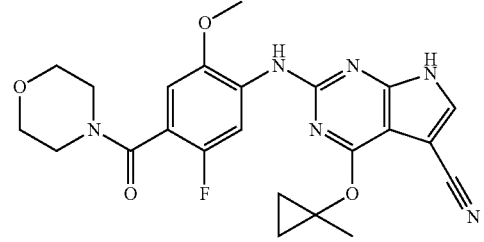 [SMILES: COc1cc(C(=O)N2CCOCC2)c(F)cc1Nc1nc(OC2(C)CC2)c2c(C#N)c[nH]c2n1] |
| 98 | 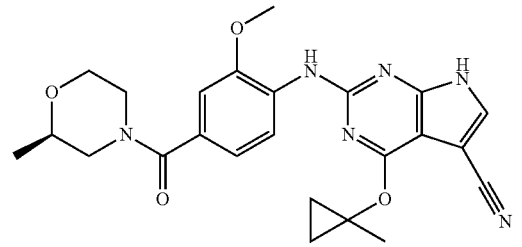 [SMILES: COc1cc(C(=O)N2CCO[C@H](C)C2)ccc1Nc1nc(OC2(C)CC2)c2c(C#N)c[nH]c2n1] |

TABLE 3-continued
| Example | Chemical Structure |
|---|---|
| 99 | 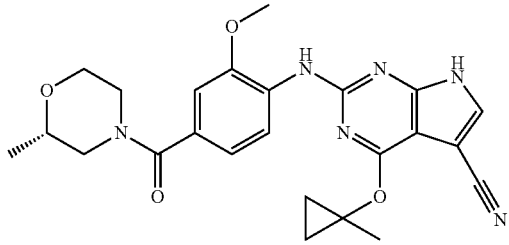 [SMILES: COc1cc(C(=O)N2CCO[C@@H](C)C2)ccc1Nc1nc(OC2(C)CC2)c2c(C#N)c[nH]c2n1] |
| 100 | 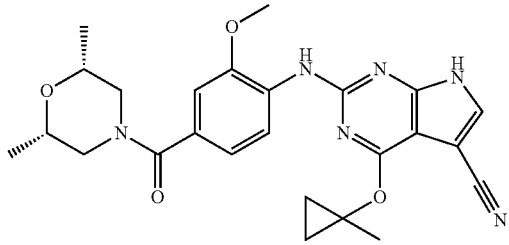 [SMILES: COc1cc(C(=O)N2C[C@@H](C)O[C@@H](C)C2)ccc1Nc1nc(OC2(C)CC2)c2c(C#N)c[nH]c2n1] |
| 101 | 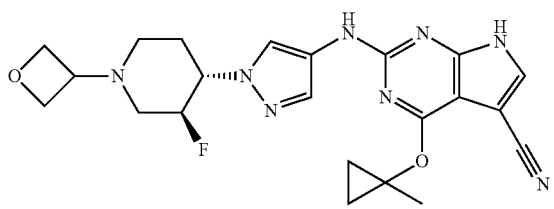 [SMILES: CC1(Oc2nc(Nc3cnn([C@H]4CCN(C5COC5)C[C@@H]4F)c3)nc3[nH]cc(C#N)c23)CC1] |
| 102 | 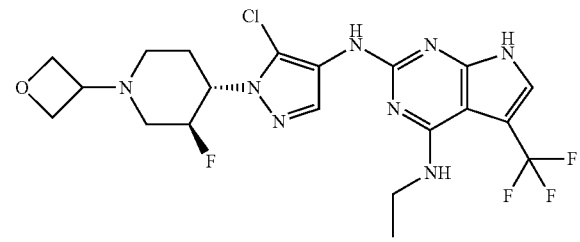 [SMILES: CCNc1nc(Nc2cnn([C@H]3CCN(C4COC4)C[C@@H]3F)c2Cl)nc2[nH]cc(C(F)(F)F)c12] |
| 103 | 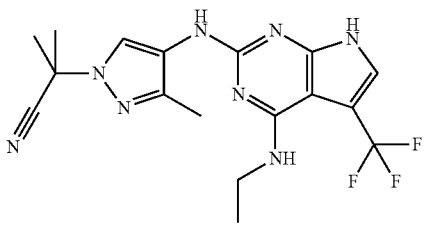 [SMILES: CCNc1nc(Nc2cn(C(C)(C)C#N)nc2C)nc2[nH]cc(C(F)(F)F)c12] |
| 104 | 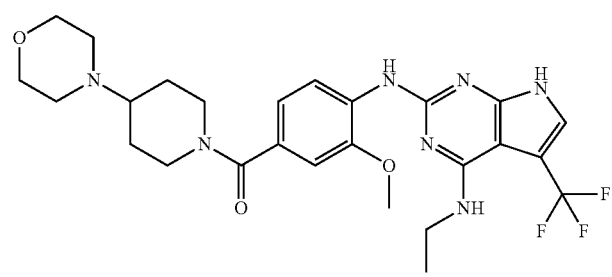 [SMILES: CCNc1nc(Nc2ccc(C(=O)N3CCC(N4CCOCC4)CC3)cc2OC)nc2[nH]cc(C(F)(F)F)c12] |

TABLE 3-continued

| Example | Chemical Structure |
|---|---|
| 105 | 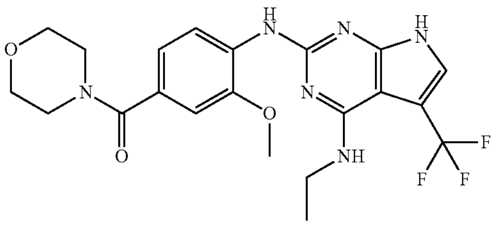 [SMILES: CCNc1nc(Nc2ccc(C(=O)N3CCOCC3)cc2OC)nc2[nH]cc(C(F)(F)F)c12] |
| 106 | 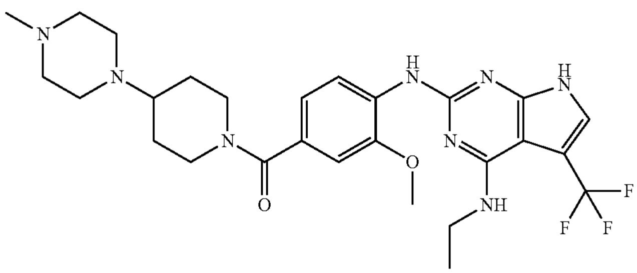 [SMILES: CCNc1nc(Nc2ccc(C(=O)N3CCC(N4CCN(C)CC4)CC3)cc2OC)nc2[nH]cc(C(F)(F)F)c12] |
| 107 | 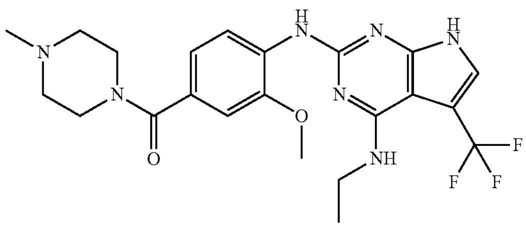 [SMILES: CCNc1nc(Nc2ccc(C(=O)N3CCN(C)CC3)cc2OC)nc2[nH]cc(C(F)(F)F)c12] |
| 108 | 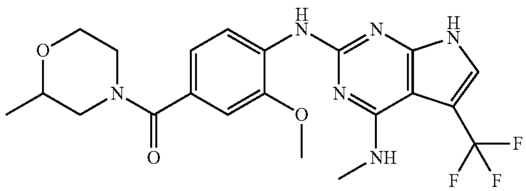 [SMILES: CNc1nc(Nc2ccc(C(=O)N3CCOC(C)C3)cc2OC)nc2[nH]cc(C(F)(F)F)c12] |
| 109 | 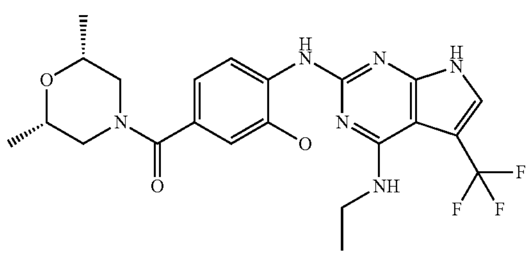 [SMILES: CCNc1nc(Nc2ccc(C(=O)N3C[C@@H](C)O[C@@H](C)C3)cc2O)nc2[nH]cc(C(F)(F)F)c12] |
| 110 | 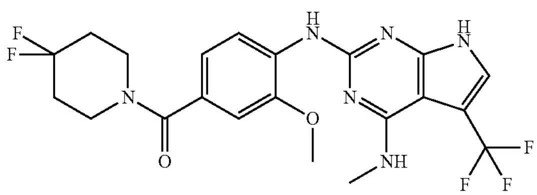 [SMILES: CNc1nc(Nc2ccc(C(=O)N3CCC(F)(F)CC3)cc2OC)nc2[nH]cc(C(F)(F)F)c12] |

TABLE 3-continued
| Example | Chemical Structure |
|---|---|
| 111 | 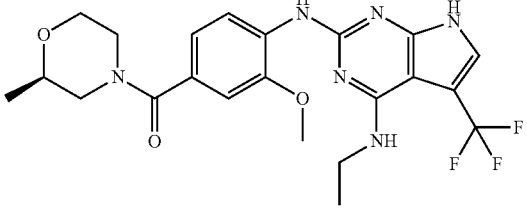 |
| 112 | 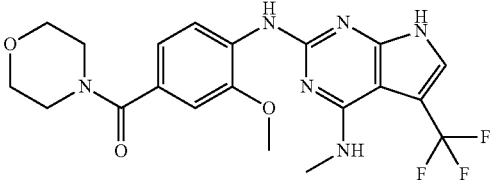 [SMILES: CNc1nc(Nc2ccc(C(=O)N3CCOCC3)cc2OC)nc2[nH]cc(C(F)(F)F)c12] |
| 113 | 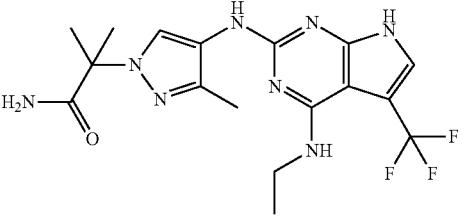 [SMILES: CCNc1nc(Nc2cn(C(C)(C)C(N)=O)nc2C)nc2[nH]cc(C(F)(F)F)c12] |
| 114 | 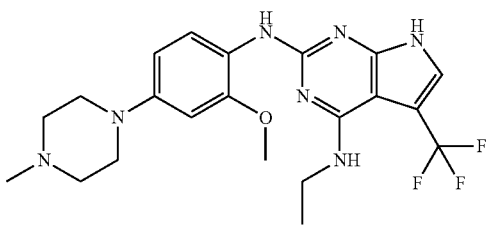 [SMILES: CCNc1nc(Nc2ccc(N3CCN(C)CC3)cc2OC)nc2[nH]cc(C(F)(F)F)c12] |
| 115 | 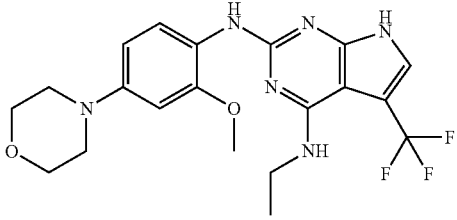 [SMILES: CCNc1nc(Nc2ccc(N3CCOCC3)cc2OC)nc2[nH]cc(C(F)(F)F)c12] |
| 116 | 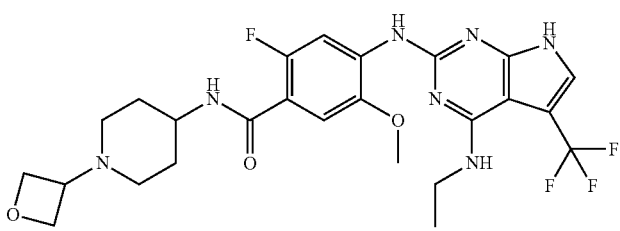 [SMILES: CCNc1nc(Nc2cc(F)c(C(=O)NC3CCN(C4COC4)CC3)cc2OC)nc2[nH]cc(C(F)(F)F)c12] |
| 117 | 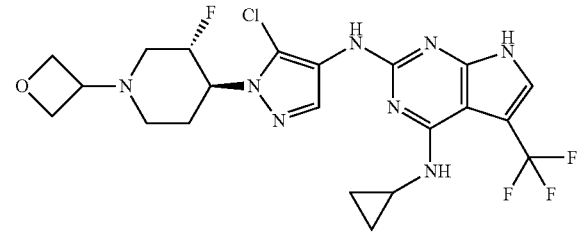 [SMILES: F[C@H]1CN(C2COC2)CC[C@@H]1n1ncc(Nc2nc(NC3CC3)c3c(C(F)(F)F)c[nH]c3n2)c1Cl] |

TABLE 3-continued
| Example | Chemical Structure |
|---------|-------------------|
| 118 | 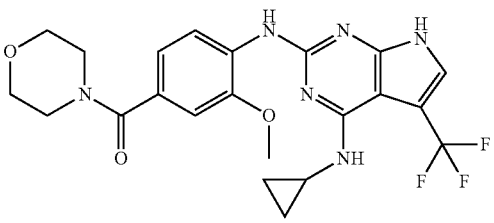 [SMILES: COc1cc(C(=O)N2CCOCC2)ccc1Nc1nc(NC2CC2)c2c(C(F)(F)F)c[nH]c2n1] |
| 119 | 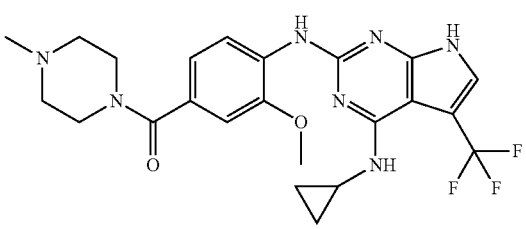 [SMILES: COc1cc(C(=O)N2CCN(C)CC2)ccc1Nc1nc(NC2CC2)c2c(C(F)(F)F)c[nH]c2n1] |
| 120 | 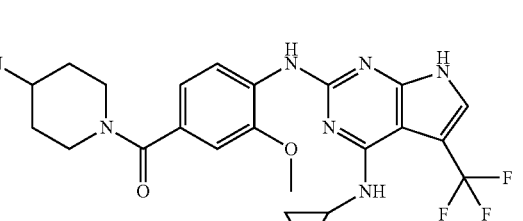 |
TABLE 4
| Example | Chemical Structure |
|---------|-------------------|
| 121 | 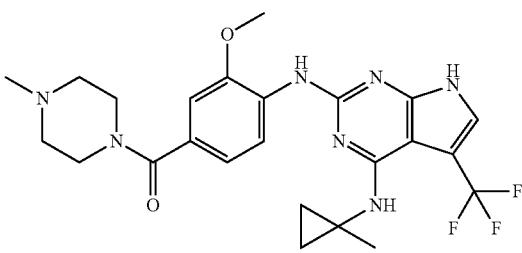 [SMILES: COc1cc(C(=O)N2CCN(C)CC2)ccc1Nc1nc(NC2(C)CC2)c2c(C(F)(F)F)c[nH]c2n1] |
| 122 | 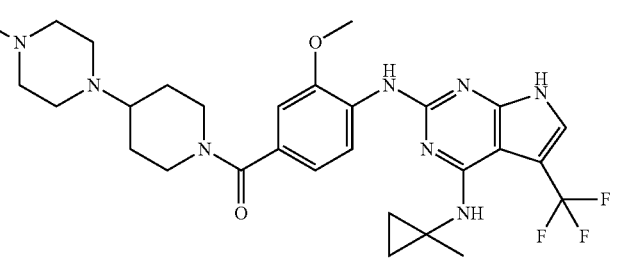 |

TABLE 4-continued

| Example | Chemical Structure |
|---------|--------------------|
| 123 | 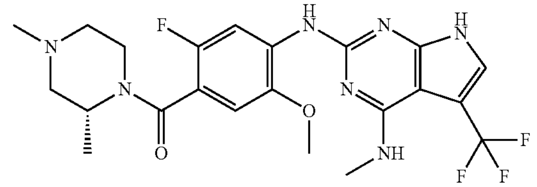 [SMILES: CNc1nc(Nc2cc(F)c(C(=O)N3CCN(C)C[C@H]3C)cc2OC)nc2[nH]cc(C(F)(F)F)c12] |
| 124 | 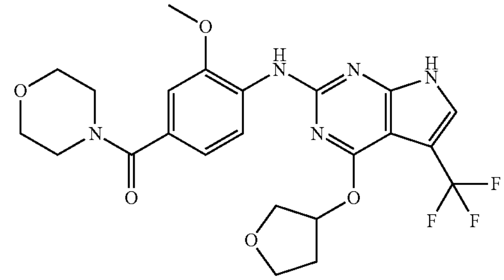 [SMILES: COc1cc(C(=O)N2CCOCC2)ccc1Nc1nc(OC2CCOC2)c2c(C(F)(F)F)c[nH]c2n1] |
| 125 | 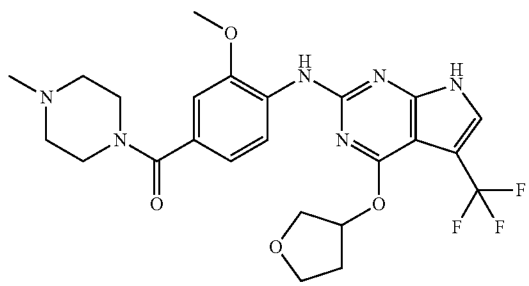 [SMILES: COc1cc(C(=O)N2CCN(C)CC2)ccc1Nc1nc(OC2CCOC2)c2c(C(F)(F)F)c[nH]c2n1] |
| 126 | 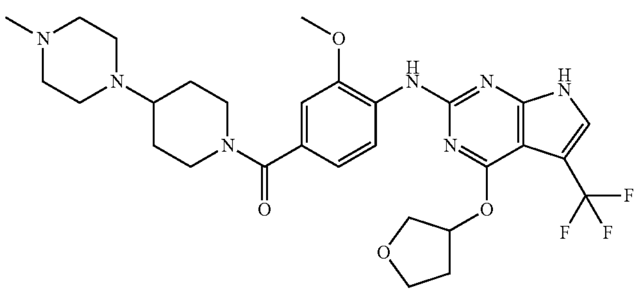 [SMILES: COc1cc(C(=O)N2CCC(N3CCN(C)CC3)CC2)ccc1Nc1nc(OC2CCOC2)c2c(C(F)(F)F)c[nH]c2n1] |
| 127 | 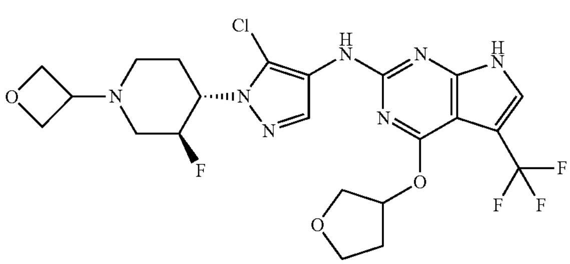 [SMILES: F[C@H]1CN(C2COC2)CC[C@@H]1n1ncc(Nc2nc(OC3CCOC3)c3c(C(F)(F)F)c[nH]c3n2)c1Cl] |
| 128 | 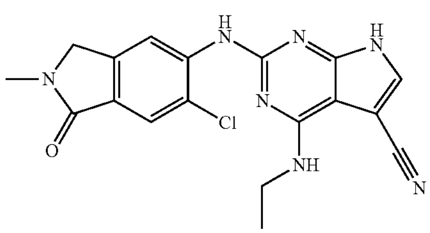 [SMILES: CCNc1nc(Nc2cc3c(cc2Cl)C(=O)N(C)C3)nc2[nH]cc(C#N)c12] |

TABLE 4-continued

| Example | Chemical Structure |
|---------|-------------------|
| 129 | 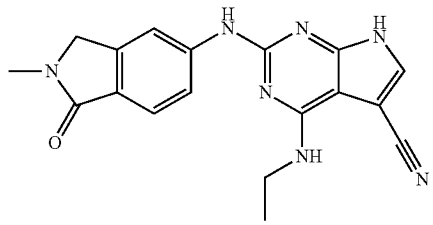 [SMILES: CCNc1nc(Nc2ccc3c(c2)CN(C)C3=O)nc2[nH]cc(C#N)c12] |
| 130 | 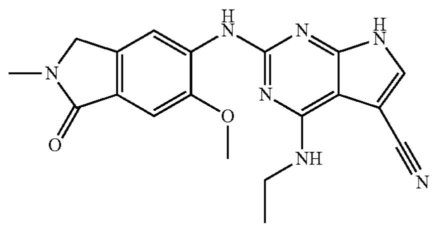 [SMILES: CCNc1nc(Nc2cc3c(cc2OC)C(=O)N(C)C3)nc2[nH]cc(C#N)c12] |
| 131 | 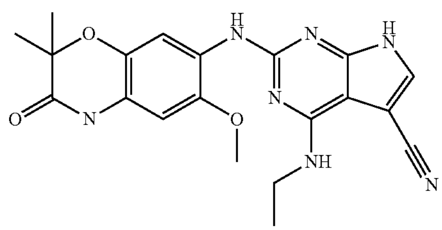 [SMILES: CCNc1nc(Nc2cc3c(cc2OC)NC(=O)C(C)(C)O3)nc2[nH]cc(C#N)c12] |
| 132 | 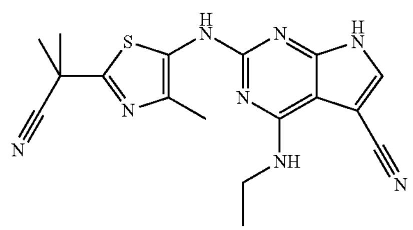 [SMILES: CCNc1nc(Nc2sc(C(C)(C)C#N)nc2C)nc2[nH]cc(C#N)c12] |
| 133 | 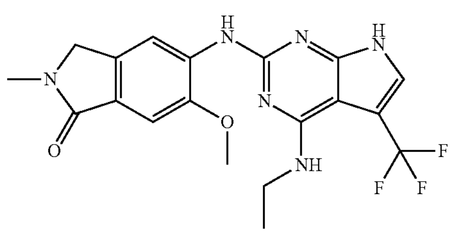 [SMILES: CCNc1nc(Nc2cc3c(cc2OC)C(=O)N(C)C3)nc2[nH]cc(C(F)(F)F)c12] |
| 134 | 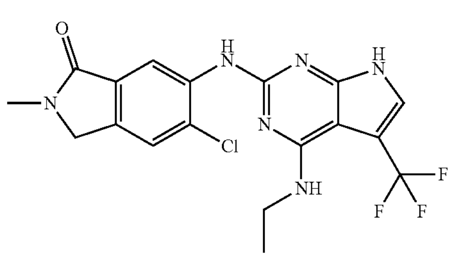 [SMILES: CCNc1nc(Nc2cc3c(cc2Cl)CN(C)C3=O)nc2[nH]cc(C(F)(F)F)c12] |

TABLE 4-continued

| Example | Chemical Structure |
|---|---|
| 135 | 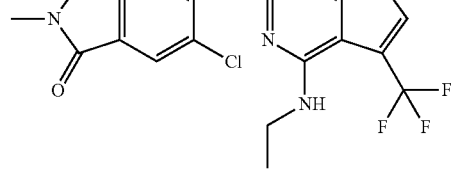 |
| 136 | 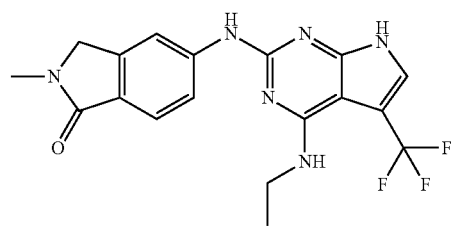 [SMILES: CCNc1nc(Nc2ccc3c(c2)CN(C)C3=O)nc2[nH]cc(C(F)(F)F)c12] |
| 137 | 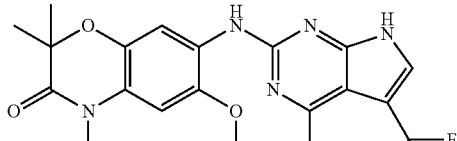 |

TABLE 5

| Example | Chemical Name | ¹H NMR; MS(ESI) m/z | yield (%) | HPEC r.t. (min) (method) |
|---|---|---|---|---|
| 1 | 2-((2-methoxy-4-(morpholine-4-carbonyl)phenyl)amino)-4-(methylamino)-7H-pyrrolo[2,3-d]pyrimidine-5-carbonitrile | ¹H NMR (400 MHz, TFA salt, Methanol-$d_4$)δ 8.50 (d, J = 8.28 Hz, 1H), 7.65 (s, 1H), 7.04 (d, J = 1.76 Hz, 1H), 6.98 (dd, J = 8.32, 1.8 Hz, 1H), 3.90 (s, 3H), 3.60 (br, 8H), 3.11 (s, 3H); 408 [M + H]⁺ | 73 | 4.848 |
| 2 | 4-(ethylamino)-2-((2-methoxy-4-(morpholine-4-carbonyl)phenyl)amino)-7H-pyrrolo[2,3-d]pyrimidine-5-carbonitrile | ¹H NMR (400 MHz, TFA salt, DMSO-$d_6$)δ 12.42 (s, 1H), 8.55 (d, J = 8.3 Hz, 1H), 7.93 (s, 1H), 7.80 (s, 1H), 7.07 (s, 1H), 7.03 (d, J = 8.3 Hz, 1H), 6.70 (br s, 1H), 4.20-4.45 (m, 2H), 3.93 (s, 3H), 3.61 (m, 4H), 3.55 (m, 4H), 1.24 (t, J = 7.1 Hz, 3H); 422 [M + H]⁺ | 32 | 5.245 |
| 3 | 4-(ethylamino)-2-((3,4,5-trimethoxyphenyl)amino)-7H-pyrrolo[2,3-d]pyrimidine-5-carbonitrile | ¹H NMR (400 MHz, TFA salt, DMSO-$d_6$)δ 12.16 (s, 1H), 8.92 (s, 1H), 7.87 (s, 1H), 7.24 (s, 2H), 6.41 (br s, 1H), 4.28-4.75 (m, 2H), 3.76 (s, 6H), 3.60 (s, 5H), 1.24 (t, J = 7.1 Hz, 3H); 369 [M + H]⁺ | 33 | 5.540 |
| 4 | 4-(ethylamino)-2-((1-methyl-1H-pyrazole-4-yl)amino)-7H-pyrrolo[2,3-d]pyrimidine-5-carbonitrile | ¹H NMR (400 MHz, TFA salt, DMSO-$d_6$)δ 12.09 (s, 1H), 8.95 (s, 1H), 7.83 (d, J =12.1 Hz, 2H), 7.52 (s, 1H), 6.42 (br s, 1H), 3.79 (s, 3H), 3.56 (m, 2H), 1.24 (t, J = 7.0 Hz, 3H); 283 [M + H]⁺ | 34 | 4.557 |
| 5 | 4-(ethylamino)-2-((1-methyl-1H-pyrazole-3-yl)amino)-7H-pyrrolo[2,3-d]pyrimidine-5-carbonitrile | ¹H NMR (400 MHz, TFA salt, DMSO-$d_6$)δ 12.40 (s, 1H), 9.76 (s, 1H), 7.91 (s, 1H), 7.61 (s, 1H), 6.97 (br s, 1H), 6.45 (s, 1H), 3.77 (s, 3H), 3.58 (m, 2H), 1.26 (t, J = 7.1 Hz, 3H); 283 [M + H]⁺ | 34 | 4.593 |
| 6 | 4-(ethylamino)-2-((5-fluoro-2-methoxy-4-(morpholine-4- | ¹H NMR (400 MHz, TFA salt, DMSO-$d_6$)δ 12.37 (s, 1H), 8.57 (d, J = 12.6 Hz, 1H), 7.92 (s, 1H), 7.61 (s, | 14 | 5.598 |

TABLE 5-continued

| Example | Chemical Name | ¹H NMR; MS(ESI) m/z | yield (%) | HPEC r.t. (min) (method) |
|---|---|---|---|---|
| | carbonyl)phenyl)amino)-7H-pyrrolo[2,3-d]pyrimidine-5-carbonitrile | 1H), 6.99 (d, J = 6.2 Hz, 1H), 6.55 (t, J = 5.6 Hz, 1H), 3.91 (s, 3H), 3.64 (br s, 5H), 3.56 (m, 5H), 3.30 (br s, 2H), 1.25 (t, J = 7.1 Hz, 3H); 440 [M + H]⁺ | | |
| 7 | 4-(ethylamino)-2-((5-fluoro-2-methoxy-4-(4-morpholinopiperidine-1-carbonyl)phenyl)amino)-7H-pyrrolo[2,3-d]pyrimidine-5-carbonitrile | 523 [M + H]⁺ | 29 | 4.602 |
| 8 | 4-(ethylamino)-2-((2-methoxy-4-(4-morpholinopiperidine-1-carbonyl)phenyl)amino)-7H-pyrrolo[2,3-d]pyrimidine-5-carbonitrile | 505 [M + H]⁺ | 24 | 4.396 |
| 9 | 2-((2-methoxy-4-(4-morpholinylpiperidine-1-carbonyl)phenyl)amino)-4-(methylamino)-7H-pyrrolo[2,3-d]pyrimidine-5-carbonitrile | ¹H NMR (400 MHz, TFA salt, Methanol-d₄) δ 8.57 (d, J = 8.28 Hz, 1H), 7.59 (s, 1H), 7.01 (d, J = 1.68 Hz, 1H), 6.98 (dd, J = 8.28, 1.76 Hz, 1H), 3.98 (m, 2H), 3.89 (s, 3H), 3.68 (m, 2H), 3.42 (m, 3H), 3.12 (m, 3H), 2.94 (m, 1H), 2.10 (m, 2H), 1.62 (m, 2H); 491 [M + H]⁺ | 15 | 4.211 |
| 10 | 2-((5-fluoro-2-methoxy-4-(morpholine-4-carbonyl)phenyl)amino)-4-(methylamino)-7H-pyrrolo[2,3-d]pyrimidine-5-carbonitrile | ¹H NMR (400 MHz, TFA salt, Methanol-d₄) δ 8.61 (d, J = 12.88 Hz, 1H), 7.53 (s, 1H), 6.86 (d, J = 6.08 Hz, 1H), 3.87 (s, 3H), 3.66 (br, 4H), 3.56 (m, 2H), 3.37 (m, 2H), 3.04 (s, 3H); 426 [M + H]⁺ | 28 | 5.237 |
| 11 | 2-((5-fluoro-2-methoxy-4-(4-morpholinopiperidine-1-carbonyl)phenyl)amino)-4-(methyl amino)-7H-pyrrolo [2,3-d]pyrimidine-5-carbonitrile | ¹H NMR (400 MHz, TFA salt, Methanol-d₄) δ 8.58 (d, J = 12.8 Hz, 1H), 7.57 (s, 1H), 6.87 (d, J = 6.12 Hz, 1H), 3.98 (m, 2H), 3.87(s, 3H), 3.80 (m, 1H), 3.65 (m, 2H), 3.42 (m, 4H), 3.12 (m, 3H), 3.05(s, 3H), 2.79 (m, 1H), 2.16 (m, 2H), 1.60 (m, 2H); 509 [M + H]⁺ | 5 | 4.445 |
| 12 | 2-((2-methoxy-4-(morpholine-4-carbonyl)phenyl)amino)-4-(propylamino)-7H-pyrrolo[2,3-d]pyrimidine-5-carbonitrile | ¹H NMR (400 MHz, TFA salt, Methanol-d₄) δ 8.44 (d, J = 8.28 Hz, 1H), 7.61 (s, 1H), 7.02 (d, J = 1.72 Hz, 1H), 6.97 (dd, J = 8.28, 1.76 Hz, 1H), 3.89 (s, 3H), 3.60 (br, 8H), 3.49 (t, J = 7.44, 7.28, 2H), 1.67 (m, 2H), 0.95 (t, J = 7.48, 7.36, 3H); 436 [M + H]⁺ | 56 | 5.718 |
| 13 | 2-((2-methoxy-4-(4-morpholinopiperidine-1-carbonyl)phenyl)amino)-4-(propylamino)-7H-pyrrolo[2,3-d]pyrimidine-5-carbonitrile | ¹H NMR (400 MHz, TFA salt, Methanol-d₄) δ 8.44 (d, J = 8.28 Hz, 1H), 7.61 (s, 1H), 7.02 (d, J = 1.64 Hz, 1H), 6.97 (dd, J = 8.32, 1.72 Hz, 1H), 3.99 (m, 2H), 3.88 (s, 3H), 3.66 (m, 2H), 3.49 (t, J = 7.44, 7.28, 2H), 3.42 (m, 3H), 3.12 (m, 4H), 2.10 (m, 2H), 1.67 (m, 2H), 1.63 (m, 3H), 0.94 (t, J = 7.44, 7.40, 3H); 519 [M + H]⁺ | 14 | 4.536 |
| 14 | 2-((5-fluoro-2-methoxy-4-(morpholine-4-carbonyl)phenyl)amino)-4-(propylamino)-7H-pyrrolo[2,3-d]pyrimidine-5-carbonitrile | ¹H NMR (400 MHz, TFA salt, Methanol-d₄) δ 8.57 (d, J = 12.8 Hz, 1H), 7.52 (s, 1H), 6.86 (d, J = 6.12 Hz, 1H), 3.87 (s, 3H), 3.66 (m, 4H), 3.56 (m, 2H), 3.46 (m, 2H), 3.38 (m, 2H), 1.64 (m, 2H), 0.95 (m, 3H); 454 [M + H]⁺ | 43 | 6.162 |
| 15 | 2-((5-fluoro-2-methoxy-4-(4-morpholinopiperidine-1-carbonyl) phenyl)amino)-4-(propylamino)-7H-pyrrolo[2,3-d]pyrimidine-5-carbonitrile | ¹H NMR (400 MHz, TFA salt, Methanol-d₄) δ 8.49 (d, J = 12.6 Hz, 1H), 7.56 (s, 1H), 6.87 (d, J = 6.08 Hz, 1H), 3.97 (m, 2H), 3.85 (s, 3H), 3.77 (m, 1H), 3.46 (m, 2H), 3.40 (m, 3H), 3.11 (m, 4H), 2.78 (m, 1H), 2.15 (m, 2H), 1.64 (m, 2H), 1.59 (m, 2H), 0.94 (t, J = 7.48, 7.36, 3H); 537 [M + H]⁺ | 15 | 4.916 |

TABLE 5-continued

| Example | Chemical Name | ¹H NMR; MS(ESI) m/z | yield (%) | HPEC r.t. (min) (method) |
|---|---|---|---|---|
| 16 | 4-(cyclopropylamino)-2-((2-methoxy-4-(morpholine-4-carbonyl)phenyl)amino)-7H-pyrrolo[2,3-d]pyrimidine-5-carbonitrile | ¹H NMR (400 MHz, TFA salt, Methanol-d₄)δ 8.73 (d, J = 8.04 Hz, 1H), 7.62 (s, 1H), 7.01 (d, J = 1.72 Hz, 1H), 6.97 (dd, J = 8.32, 1.8 Hz, 1H), 3.9 (s, 3H), 3.60 (br, 8H), 2.86 (m, 1H), 0.92 (d, J = 6.04, 2H), 0.70 (m, 2H); 434 [M + H]⁺ | 19 | 5.018 |
| 17 | 4-(cyclopropylamino)-2-((2-methoxy-4-(4-morpholinopiperidine-1-carbonyl)phenyl)amino)-7H-pyrrolo[2,3-d]pyrimidine-5-carbonitrile | ¹H NMR (400 MHz, TFA salt, Methanol-d₄)δ 8.70 (d, J = 8.36 Hz, 1H), 7.64 (s, 1H), 7.01 (d, J = 1.64 Hz, 1H), 6.97 (dd, J = 8.32, 1.76 Hz, 1H), 3.98 (m, 2H), 3.90(s, 3H), 3.67 (m, 2H), 3.41 (m, 3H), 3.12 (m, 5H), 2.84 (m, 1H), 2.11 (m, 2H), 1.61 (m, 2H), 0.93 (m, 2H), 0.72 (m, 2H); 517 [M + H]⁺ | 14 | 4.034 |
| 18 | 4-(cyclopropylamino)-2-((5-fluoro-2-methoxy-4-(morpholine-4-carbonyl)phenyl)amino)-7H-pyrrolo[2,3-d]pyrimidine-5-carbonitrile | ¹H NMR (400 MHz, TFA salt, Methanol-d₄)δ 8.69 (d, J = 12.56 Hz, 1H), 7.65 (s, 1H), 6.91 (d, J = 6.04 Hz, 1H), 3.89 (s, 3H), 3.66 (br, 4H), 3.55 (m, 2H), 3.34 (m, 2H), 2.83 (m, 1H), 0.94 (m, 2H), 0.72 (m, 2H); 452 [M + H]⁺ | 57 | 5.484 |
| 19 | 4-(cyclopropylamino)-2-((5-fluoro-2-methoxy-4-(4-morpholinopiperidine-1-carbonyl)phenyl)amino)-7H-pyrrolo[2,3-d]pyrimidine-5-carbonitrile | ¹H NMR (400 MHz, TFA salt, Methanol-d₄)δ 8.76 (d, J = 12.8 Hz, 1H), 7.60 (s, 1H), 6.88 (d, J = 6.12 Hz, 1H), 3.98 (m, 2H), 3.87(s, 3H), 3.79 (m, 2H), 3.65 (m, 2H), 3.41 (m, 3H), 3.12 (m, 4H), 2.82 (m, 1H), 2.78 (m, 1H), 2.16 (m, 2H), 1.58 (m, 2H), 0.89 (m, 2H), 0.67 (m, 2H); 535 [M + H]⁺ | 44 | 4.635 |
| 20 | (R)-2-((2-methoxy-4-(2-methylmorpholine-4-carbonyl)phenyl)amino)-4-(methylamino)-7H-pyrrolo[2,3-d]pyrimidine-5-carbonitrile | ¹H NMR (400 MHz, TFA salt, DMSO-d₆)δ12.40(s, 1H), 8.57(d, J = 8.28 Hz, 1H), 7.92(s, 1H), 7.79(brs, 1H), 7.06(s, 1H), 7.02(d, J = 8.24 Hz, 1H), 6.76(brs, 1H), 3.93(s, 3H), 3.80(brs, 2H), 3.52-3.44(m, 2H), 3.17(s, 3H), 3.03(s, 3H), 1.08(brs, 3H); 422[M + H]⁺ | 37 | 5.087 |
| 21 | (S)-2-((2-methoxy-4-(2-methylmorpholine-4-carbonyl)phenyl)amino)-4-(methylamino)-7H-pyrrolo[2,3-d]pyrimidine-5-carbonitrile | ¹H NMR (400 MHz, TFA salt, DMSO-d₆)δ 12.35 (s, 1H), 8.58 (d, J = 8.28 Hz, 1H), 7.89 (s, 1H), 7.71 (brs, 1H), 7.06 (s, 1H), 7.00 (d, J = 8.32 Hz, 1H), 6.68 (brs, 1H), 4.02-3.99 (m, 2H), 3.91 (s, 3H), 3.48-3.43 (m, 4H), 3.08-3.01 (m, 1H), 3.00 (s, 3H), 1.07 (brs, 3H); 422 [M + H]⁺ | 36 | 5.126 |
| 22 | 2-((4-((2R,6S)-2,6-dimethylmorpholine-4-carbonyl)-2-methoxyphenyl)amino)-4-(methylamino)-7H-pyrrolo[2,3-d]pyrimidine-5-carbonitrile | ¹H NMR (400 MHz, TFA salt, DMSO-d₆)δ 12.38 (s, 1H), 8.56 (d, J = 8.36 Hz, 1H), 7.90 (s, 1H), 7.77 (brs, 1H), 7.05 (s, 1H), 7.00 (d, J = 8.28 Hz, 1H), 6.73 (br, 1H), 4.09-3.99 (m, 4H), 3.82 (s, 3H), 3.56-3.51 (m, 2H), 3.01 (s, 3H), 1.27 (brs, 6H); 436 [M + H]⁺ | 51 | 5.363 |
| 23 | 2-((4-(4,4-difluoropiperidine-1-carbonyl)-2-methoxyphenyl amino)-4-(methylamino)-7H-pyrrolo[2,3-d]pyrimidine-5-carbonitrile | ¹H NMR (400 MHz, TFA salt, DMSO-d₆)δ 12.40 (s, 1H), 8.56 (d, J = 8.28 Hz, 1H), 7.91 (s, 1H), 7.80 (brs, 1H), 7.10 (s, 1H), 7.04 (d, J = 6.52 Hz, 1H), 6.77 (brs, 1H), 3.93 (s, 3H), 3.47 (brs, 4H), 3.01 (s, 3H), 2.12-2.05 (4H); 442 [M + H]⁺ | 46 | 5.641 |
| 24 | 2-((4-((2R,6S)-2,6-dimethylmorpholine-4-carbonyl)-2-methoxyphenyl)amino)-4-(ethylamino)-7H-pyrrolo[2,3-d]pyrimidine-5-carbonitrile | ¹H NMR (400 MHz, TFA salt, Methanol-d₄)δ 8.49 (d, J = 8.3 Hz, 1H), 7.66 (s, 1H), 7.04 (s, 1H), 6.99 (d, J = 8.3 Hz, 1H), 4.49 (m, 1H), 3.91 (s, 3H), 3.60 (m, 5H), 2.80 (m, 1H), 1.31 (t, J = 7.2 Hz, 4H), 1.08 (m, 6H); 450 [M + H]⁺ | 36 | 5.694 |
| 25 | (R)-4-(ethylamino)-2-((2-methoxy-4-(2-methylmorpholine-4-carbonyl)phenyl)amino)-7H-pyrrolo[2,3- | ¹H NMR (400 MHz, TFA salt, Methanol-d₄)δ 8.55 (d, J = 8.3 Hz, 1H), 7.74 (s, 1H), 7.15 (s, 1H), 7.09 (d, J = 8.3 Hz, 1H), 4.51 (br s, 1H), 4.01 (s, 3H), 3.92 (br s, 2H), 3.72 (q, | 46 | 5.445 |

TABLE 5-continued

| Example | Chemical Name | $^1$H NMR; MS(ESI) m/z | yield (%) | HPEC r.t. (min) (method) |
|---|---|---|---|---|
| | d]pyrimidine-5-carbonitrile | J = 7.2 Hz, 3H), 3.61 (br s, 2H), 2.75 (m, 1H), 1.40 (t, J = 7.2 Hz, 3H), 1.18 (br s, 3H); 436 [M + H]$^+$ | | |
| 26 | (S)-4-(ethylamino)-2-((2-methoxy-4-(2-methylmorpholine-4-carbonyl)phenyl)amino)-7H-pyrrolo[2,3-d]pyrimidine-5-carbonitrile | $^1$H NMR (400 MHz, TFA salt, Methanol-d$_4$) δ 8.58 (d, J = 8.3 Hz, 1H), 7.74 (s, 1H), 7.15 (s, 1H), 7.10 (d, J = 8.3 Hz, 1H), 4.48 (m, 1H), 4.01 (s, 3H), 3.91 (br s, 2H), 3.72 (q, J = 7.2 Hz, 2H), 3.61 (br s, 3H), 2.80 (m, 1H), 1.40 (t, J = 7.2 Hz, 3H), 1.18 (br s, 3H); 436 [M + H]$^+$ | 28 | 5.449 |
| 27 | 2-((4-(4,4-difluoropiperidine-1-carbonyl)-2-methoxyphenyl)amino)-4-(ethylamino)-7H-pyrrolo[2,3-d]pyrimidine-5-carbonitrile | $^1$H NMR (400 MHz, TFA salt, Methanol-d$_4$) δ 8.58 (d, J = 8.3 Hz, 1H), 7.74 (s, 1H), 7.18 (s, 1H), 7.13 (d, J = 8.3 Hz, 1H), 4.02 (s, 3H), 3.78 (br s, 3H), 3.75 (q, J = 7.2 Hz, 3H), 2.09 (br s, 4H), 1.40 (t, J = 7.2 Hz, 3H); 456 [M + 1]$^+$ | 32 | 5.934 |
| 28 | 6-((1,3-dimethyl-1H-pyrazol-4-yl)amino)-4-(methylamino)-1H-pyrrolo[2,3-b]pyrimidine-3-carbonitrile | $^1$H NMR (400 MHz, TFA salt, Methanol-d$_4$) δ 7.53 (s, 1H), 7.50 (s, 1H), 3.75 (s, 3H), 3.07 (s, 3H), 2.17 (s, 3H); 283 [M + H]$^+$ | 39 | 4.180 |
| 29 | 6-((1,5-dimethyl-1H-pyrazol-4-yl)amino)-4-(methyl amino)-1H-pyrrolo[2,3-b]pyrimidine-3-carbonitrile | $^1$H NMR (400 MHz, TFA salt, Methanol-d$_4$) δ 7.75 (s, 1H), 7.56 (s, 1H), 3.77 (s, 3H), 3.09 (s, 3H), 2.12 (s, 3H); 283 [M + H]$^+$ | 39 | 4.214 |
| 30 | 6-((1-isopropyl-3-methyl-1H-pyrazol-4-yl)amino)-4-(methylamino)-1H-pyrrolo[2,3-b]pyrimidine-3-carbonitrile | $^1$H NMR (400 MHz, TFA salt, Methanol-d$_4$) δ 7.83 (s, 1H), 7.58 (s, 1H), 4.41-4.34 (m, 1H), 3.09 (s, 3H), 2.13 (s, 3H), 1.42 (d, J = 6.7 Hz, 6H); 311 [M + H]$^+$ | 50 | 4.612 |
| 31 | 6-((1-isopropyl-5-methyl-1H-pyrazol-4-yl)amino)-4-(methylamino)-1H-pyrrolo[2,3-b]pyrimidine-3-carbonitrile | $^1$H NMR (400 MHz, TFA salt, Methanol-d$_4$) δ 7.55 (s, 1H), 7.54 (s, 1H), 4.54-4.47 (m, 1H), 3.07 (s, 3H), 2.18 (s, 3H), 1.41 (d, J = 6.6 Hz, 6H); 311 [M + H]$^+$ | 49 | 4.572 |
| 32 | 2-((1,3-dimethyl-1H-pyrazol-4-yl)amino)-4-(ethylamino)-7H-pyrrolo[2,3-d]pyrimidine-5-carbonitrile | $^1$H NMR (400 MHz, TFA salt, Methanol-d$_4$) δ 7.64 (s, 1H), 7.58 (s, 1H), 3.84 (s, 3H), 3.70 (q, J = 7.2 Hz, 2H), 2.27 (s, 3H), 1.34 (t, J = 7.2 Hz, 3H); 297 [M + H]$^+$ | 29 | 4.498 |
| 33 | 2-((1,5-dimethyl-1H-pyrazol-4-yl)amino)-4-(ethylamino)-7H-pyrrolo[2,3-d]pyrimidine-5-carbonitrile | $^1$H NMR (400 MHz, TFA salt, Methanol-d$_4$) δ 7.82 (s, 1H), 7.66 (s, 1H), 3.87 (s, 3H), 3.72 (q, J = 7.2 Hz, 2H), 2.22 (s, 3H), 1.36 (t, J = 7.2 Hz, 3H); 297 [M + H]$^+$ | 31 | 4.527 |
| 34 | 4-(ethylamino)-2-((1-isopropyl-3-methyl-1H-pyrazol-4-yl)amino)-7H-pyrrolo[2,3-d]pyrimidine-5-carbonitrile | $^1$H NMR (400 MHz, TFA salt, DMSO-d$_6$) δ 12.05 (brs, 1H), 8.13 (brs, 1H), 7.74 (s, 1H), 7.54 (s, 1H), 6.30 (brs, 1H), 4.51-4.40 (m, 1H), 3.54-3.45 (m, 2H), 2.16 (s, 3H), 1.35 (d, J = 6.6 Hz, 6H), 1.18 (t, J = 7.1 Hz, 3H); 325 [M + H]$^+$ | 28 | 4.829 |
| 35 | 4-(ethylamino)-2-((1-isopropyl-5-methyl-1H-pyrazol-4-yl)amino)-7H-pyrrolo[2,3-d]pyrimidine-5-carbonitrile | $^1$H NMR (400 MHz, TFA salt, DMSO-d$_6$) δ 12.16 (brs, 1H), 8.36 (brs, 1H), 7.87 (s, 1H), 7.79 (s, 1H), 6.59 (brs, 1H), 4.41-4.30 (m, 1H), 3.59-3.49 (m, 2H), 2.11 (s, 3H), 1.38 (d, J = 6.5 Hz, 6H), 1.21 (t, J = 6.9 Hz, 3H); 325 [M + H]$^+$ | 14 | 4.883 |
| 36 | 2-((2-methoxy-4-(morpholine-4-carbonyl)phenyl)amino)-4-((1-methylcyclopropyl)amino)-7H-pyrrolo[2,3-d]pyrimidine-5-carbonitrile | $^1$H NMR (400 MHz, TFA salt, DMSO-d$_6$) δ 12.30 (s, 1H), 8.80 (d, J = 8.2 Hz, 1H), 7.91 (d, J = 2.4 Hz, 1H), 7.61 (br, 1H), 7.06 (s, 1H), 7.05 (d, J = 8.4 Hz, 1H), 6.64 (br, 1H), 3.93 (s, 3H), 3.70-3.52 (m, 8H), 1.23 (s, 3H), 0.89-0.82 (m, 2H), 0.82-0.76 (m, 2H); 448 [M + H]$^+$ | 13 | 5.339 |
| 37 | 2-((5-fluoro-2-methoxy-4-(morpholine-4-carbonyl)phenyl)amino)-4-((1-methylcyclopropyl)amino)- | $^1$H NMR (400 MHz, TFA salt, Methanol-d$_4$) δ 8.91 (d, J = 12.5 Hz, 1H), 7.71 (s, 1H), 7.01 (d, J = 1H) 3.99 (s, 3H), 3.77-3.76 (m, 4H), 3.67-3.65 (m, 2H), 3.49-3.45 (m, 2H), | 4 | 6.032 |

TABLE 5-continued

| Example | Chemical Name | $^1$H NMR; MS(ESI) m/z | yield (%) | HPEC r.t. (min) (method) |
|---|---|---|---|---|
| | 7H-pyrrolo[2,3-d]pyrimidine-5-carbonitrile | 1.59 (s, 3H), 1.04-1.01 (m, 2H), 0.99-0.96 (m, 2H); 466 [M + H]$^+$ | | |
| 38 | 2-((1-isopropyl-5-methyl-1H-pyrazole-4-yl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 7.75 (s, 1H), 7.69 (s, 1H), 4.63-4.56 (m, 1H), 2.29 (s, 3H), 1.52 (s, 3H), 1.48 (d, J = 6.6 Hz, 6H), 1.09-0.95 (m, 2H), 0.95-0.77 (m, 2H); 351 [M + H]$^+$ | 7 | 4.994 |
| 39 | 2-((1-isopropyl-3-methyl-1H-pyrazole-4-yl)amino)-4-((1-methylcyclopropyl)amino)-7H-pyrrolo [2,3-d]pyrimidine-5-carbonitrile | $^1$H NMR (400 MHz, TFA salt, Methanol-d$_4$)δ 8.04 (s, 1H), 7.73 (s, 1H), 4.49-4.42 (m, 1H), 2.26 (s, 3H), 1.55 (s, 3H), 1.50 (d, J = 6.7 Hz, 6 H), 1.12-1.00 (m, 2H), 0.99-0.83 (m, 2H); 351 [M + H]$^+$ | 11 | 5.042 |
| 40 | 2-((1,3-dimethyl-1H-pyrazole-4-yl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 7.70 (s, 1H), 7.66 (s, 1H), 3.83 (s, 3H), 2.28 (s, 3H), 1.54 (s, 3H), 1.00 (br, 2H), 0.87 (br, 2H); 323 [M + H]$^+$ | 7 | 4.576 |
| 41 | 2-((1,5-dimethyl-1H-pyrazole-4-yl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 8.00 (s, 1H), 7.70 (2, 1H), 3.86 (s, 3H), 2.26 (s, 3H), 1.58 (s, 3H), 1.04 (br, 2H), 0.92 (br, 2H); 323 [M + H]$^+$ | 4 | 4.623 |
| 42 | (R)-2-((2-methoxy-4-(2-methylmorpholine-4-carbonyl)phenyl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 8.64 (d, J = 8.3 Hz, 1H), 7.64 (s, 1H), 7.00 (s, 1H), 6.95 (d, J = 8.3 Hz, 1H), 4.41-4.20 (m, 1H), 3.88 (s, 3H), 3.85-3.66 (m, 1H), 3.65-3.52 (m, 1H), 3.51-3.39 (m, 2H), 1.45 (s, 3H), 3.01-2.76 (m, 1H), 2.75-2.48 (m, 1H), 1.14-0.97 (m, 2H), 0.94 (s, 3H), 0.86-0.83 (m, 2H); 462 [M + H]$^+$ | 23 | 5.564 |
| 43 | (S)-2-((2-methoxy-4-(2-methylmorpholine-4-carbonyl)phenyl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 8.64 (d, J = 8.3 Hz, 1H), 7.64 (s, 1H), 7.00 (s, 1H), 6.95 (d, J = 8.3 Hz, 1H), 4.43-4.18 (m, 1H), 3.88 (s, 3H), 3.83-3.36 (m, 4H), 1.45 (s, 3H), 2.99-2.49 (m, 2H), 1.12-0.98 (m, 2H), 0.94 (s, 3H), 0.88-0.81 (m, 2H); 462 [M + H]$^+$ | 25 | 5.564 |
| 44 | 2-((4-((2R,6S)-2,6-dimethylmorpholine-4-carbonyl)-2-methoxyphenyl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 8.62 (d, J = 8.3 Hz, 1H), 7.64 (s, 1H), 7.00 (s, 1H), 6.94 (d, J = 8.3 Hz, 1H), 4.45-4.25 (m, 1H), 3.88 (s, 3H), 3.58-3.43 (m, 2H), 2.87-2.69 (m, 1H), 2.56-2.39 (m, 1H), 1.45 (s, 3H), 1.26-0.69 (m, 11H); 476 [M + H]$^+$ | 17 | 5.891 |
| 45 | 2-((4-(4,4-difluoropiperidine-1-carbonyl)-2-methoxyphenyl)amino)-4-((1-methylcyclopropyl)amino)-7H-pyrrolo[2,3-d]pyrimidine-5-carbonitrile | $^1$H NMR (400 MHz, TFA salt, Methanol-d$_4$)δ 8.68 (d, J = 8.3 Hz, 1H), 7.61 (s, 1H), 7.02 (s, 1H), 6.98 (d, J = 8.3 Hz, 1H), 3.88 (s, 3H), 3.78-3.50 (m, 4H), 2.59-2.47 (m, 2H), 2.01-1.83 (m, 4H), 1.45 (s, 3H), 1.18-1.11 (m, 2H); 482 [M + H]$^+$ | 27 | 6.036 |
| 46 | 2-(4-((5-cyano-4-(methylamino)-7H-pyrrolo[2,3-d]pyrimidine-2-yl)amino)-3-methyl-1H-pyrazol-1-yl)-2-methylpropaneamide | $^1$H NMR (400 MHz, TFA salt, Methanol-d$_4$)δ 8.10 (s, 1H), 7.67 (s, 1H), 3.19 (s, 3H), 2.25 (s, 3H), 1.85 (s, 6H); 354 [M + H]$^+$ | 34 | 4.226 |
| 47 | 2-((1-(2-cyanopropane-2-yl)-3-methyl-1H-pyrazole-4-yl)amino)-4-(methylamino)-7H-pyrrolo[2,3-d]pyrimidine-5-carbonitrile | $^1$H NMR (400 MHz, TFA salt, Methanol-d$_4$)δ 8.24 (s, 1H), 7.69 (s, 1H), 3.19 (s, 3H), 2.28 (s, 3H), 2.02 (s, 6H); 336 [M + H]$^+$ | 61 | 4.799 |

TABLE 5-continued

| Example | Chemical Name | ¹H NMR; MS(ESI) m/z | yield (%) | HPEC r.t. (min) (method) |
|---|---|---|---|---|
| 48 | 4-(ethylamino)-2-((3-methoxy-5-(morpholine-4-carbonyl)pyridine-2-yl)amino)-7H-pyrrolo[2,3-d]pyrimidine-5-carbonitrile | ¹H NMR (400 MHz, TFA salt, Methanol-d₄)δ 7.94 (s, 1H), 7.75 (s, 1H), 7.58 (s, 1H), 3.98 (s, 3H), 3.71-3.38 (m, 10H), 1.28 (t, J = 7.2 Hz, 3H); 423 [M + H]⁺ | 13 | 4.544 |
| 49 | 2-((1-(2-cyanopropane-2-yl)-3-methyl-1H-pyrazole-4-yl)amino)-4-((1-methylcyclopropyl)amino)-7H-pyrrolo[2,3-d]pyrimidine-5-carbonitrile | ¹H NMR (400 MHz, TFA salt, Methanol-d₄)δ 8.30 (s, 1H), 7.72 (s, 1H), 2.30 (s, 3H), 2.00 (s, 6H), 1.56 (s, 3H), 1.11-1.00 (m, 2H), 1.00-0.84 (m, 2H); 376 [M + H]⁺ | 31 | 5.246 |
| 50 | 2-((5-chloro-1-((3S,4S)-3-fluoro-1-(oxetane-3-yl)piperidine-4-yl)-1H-pyrazole-4-yl)amino)-4-(methylamino)-7H-pyrrolo[2,3-d]pyrimidine-5-carbonitrile | ¹H NMR (400 MHz, TFA salt, Methanol-d₄)δ 8.05 (s, 1H), 7.67 (s, 1H), 5.19-5.06 (m, 1H), 4.84-4.81 (m, 2H), 4.78-4.71 (m, 2H), 4.17-4.14 (m, 1H), 3.69-3.56 (m, 1H), 3.40-3.33 (m, 2H), 3.14 (s, 3H), 2.95-2.71 (m, 2H), 2.42-2.19 (m, 2H); 446 [M + H]⁺ | 8 | 4.213 |
| 51 | 2-((5-chloro-1-((3S,4S)-3-fluoro-1-(oxetane-3-yl)piperidine-4-yl)-1H-pyrazole-4-yl)amino)-4-(ethylamino)-7H-pyrrolo[2,3-d]pyrimidine-5-carbonitrile | ¹H NMR (400 MHz, TFA salt, Methanol-d₄)δ 7.83 (s, 1H), 7.52 (s, 1H), 5.09-4.93 (m, 1H), 4.71-4.60 (m, 5H), 4.16-4.11 (m, 1H), 3.61-3.54 (m, 1H), 3.50-3.45 (m, 2H), 3.30-3.25 (m, 1H), 2.90-2.70 (m, 2H), 2.34-2.26 (m, 2H), 1.14 (t, J = 7.2 Hz, 3H); 460 [M + H]⁺ | 39 | 4.473 |
| 52 | 2-((5-chloro-1-((3S,4S)-3-fluoro-1-(oxetane-3-yl)piperidine-4-yl)-1H-pyrazole-4-yl)amino)((1-methylcyclopropyl)amino)-7H-pyrrolo[2,3-d]pyrimidine-5-carbonitrile | ¹H NMR (400 MHz, TFA salt, Methanol-d₄)δ 8.23 (s, 1H), 7.75 (s, 1H), 5.11-5.24 (m, 1H), 4.77-4.88 (m, 5H), 4.26 (m, 1H), 3.73 (m, 1H), 2.95 (m, 1H), 2.86 (m, 1H), 2.45 (m, 2H), 2.35 (m, 1H), 1.55 (s, 3H), 1.30 (br s, 1H), 1.04 (br s, 2H), 0.91 (br s, 2H); 486 [M + H]⁺ | 36 | 4.583 |
| 53 | 4-(ethylamino)-2-((1-(3S,4S)-3-fluoro-1-(oxetane-3-yl)piperidine-4-yl)-1H-pyrazole-4-yl)amino)-7H-pyrrolo[2,3-d]pyrimidine-5-carbonitrile | ¹H NMR (400 MHz, TFA salt, Methanol-d₄)δ 7.89 (s, 1H), 7.62 (s, 1H), 7.51 (s, 1H), 5.07-4.91 (m, 1H), 4.72-4.61 (m, 4H), 4.56-4.48 (m, 1H), 4.26-4.20 (m, 1H), 3.66-3.59 (m, 1H), 3.57-3.52 (m, 2H), 3.40-3.34 (m, 1H), 3.04-2.85 (m, 2H), 2.31-2.26 (m, 2H), 1.19 (t, J = 7.2 Hz, 3H); 426 [M + H]⁺ | 29 | 4.232 |
| 54 | 2-((1-((3S,4S)-3-fluoro-1-(oxetane-3-yl)piperidine-4-yl)-1H-pyrazole-4-yl)amino)-4-((methylcyclopropyl)amino)-7H-pyrrolo[2,3-d]pyrimidine-5-carbonitrile | ¹H NMR (400 MHz, TFA salt, Methanol-d₄)δ 8.21 (s, 1H), 7.89 (s, 1H), 7.74 (s, 1H), 5.06-5.22 (m, 1H), 4.81-4.90 (m, 4H), 4.69 (m, 1H), 4.35 (m, 1H), 3.79 (m, 1H), 3.50 (m, 1H), 3.09 (m, 1H), 2.97 (m, 1H), 2.48 (m, 2H), 1.60 (s, 3H), 1.07 (br s, 2H), 0.98 (br s, 2H); 452 [M + H]⁺ | 65 | 4.367 |
| 55 | 4-((5-cyano-4-(methylamino)-7H-pyrrolo[2,3-d]pyrimidine-2-yl)amino)-3-methoxy-N-(1-methylpiperidine-4-yl)benzamide | ¹H NMR (400 MHz, TFA salt, Methanol-d₄)δ8.73 (d, J = 9 Hz, 1H), 7.69 (s, 1H), 7.53-7.51 (m, 2H), 4.19-4.13 (m, 1H), 4.02 (s, 3H), 3.64-3.55 (m, 2H), 3.51-3.34 (m, 2H), 3.18 (s, 3H), 2.90 (s, 3H), 2.28-1.89 (m, 4H); 435 [M + H]⁺ | 18 | 4.379 |
| 56 | 4-((5-cyano-4-(ethylamino)-7H-pyrrolo[2,3-d]pyrimidine-2-yl)amino)-3-methoxy-N-(1-methylpiperidine-4-yl)benzamide | ¹H NMR (400 MHz, TFA salt, Methanol-d₄)δ 8.68 (d, J = 8 Hz, 1H), 7.70 (s, 1H), 7.53-7.51 (m, 2H), 4.22-4.10 (m, 1H), 4.03 (s, 3H), 3.71-3.66 (m, 2H), 3.64-3.55 (m, 2H), 3.25-3.11 (m, 2H), 2.30-2.22 (m, 2H), 1.98-1.83 (m, 2H), 1.38 (t, J = 7.2 Hz, 3H); 449 [M + H]⁺ | 22 | 4.536 |
| 57 | 2-((2-methoxy-4-(oxetane-3-yl)piperazine-1-carbonyl)phenyl)amino)-4-(methylamino)-7H- | ¹H NMR (400 MHz, TFA salt, Methanol-d₄)δ 8.66 (d, J = 8.3 Hz, 1H), 7.73 (s, 1H), 7.17 (s, 1H), 7.14 (d, J = 8.32, 1H), 4.88-4.81 (m, | 19 | 4.137 |

TABLE 5-continued

| Example | Chemical Name | $^1$H NMR; MS(ESI) m/z | yield (%) | HPEC r.t. (min) (method) |
|---|---|---|---|---|
|  | pyrrolo[2,3-d]pyrimidine-5-carbonitrile | 4H), 4.43-4.33(m, 1H), 4.00 (s, 3 H), 4.00-3.84 (m, 4H), 3.28-3.19 (m, 4H), 3.19 (s, 3H); 463 [M + H]$^+$ | | |
| 58 | 44-(ethylamino)-2-((2-methoxy-4-(4-(oxetane-3-yl)piperazine-1-carbonyl)phenyl)amino)-7H-pyrrolo[2,3-d]pyrimidine-5-carbonitrile | $^1$H NMR (400 MHz, TFA salt, Methanol-d$_4$)δ 8.56 (d, J = 8.3 Hz, 1H), 7.73 (s, 1H), 7.18 (s, 1H), 7.14 (d, J = 8.3 Hz, 1H), 4.88-4.85 (m, 4H), 4.43-4.40 (m, 1H), 4.05 (s, 3H), 4.05-3.86 (m, 4H), 3.69-3.64 (m, 2H), 3.31-3.28 (m, 4H), 1.37 (t, J = 7.2 Hz, 3H); 477 [M + H]$^+$ | 36 | 4.389 |
| 59 | 2-((5-chloro-1-(2-methoxyethyl)-1H-pyrazole-4-yl)amino)-4-(methylamino)-7H-pyrrolo[2,3-d]pyrimidine-5-carbonitrile | $^1$H NMR (400 MHz, TFA salt, Methanol-d$_4$)δ 7.93 (s, 1H), 7.67 (s, 1H), 4.37 (t, J = 5.2 Hz, 2H), 3.81 (t, J = 5.2 Hz, 2H), 3.33 (s, 3H), 3.16 (s, 3H); 347 [M + H]$^+$ | 15 | 4.625 |
| 60 | 4-((5-cyano-4-(ethylamino)-7H-pyrrolo[2,3-d]pyrimidine-2-yl)amino)-3-methoxy-N-(1-(oxetane-3-yl)piperidine-4-yl)benzylamide | $^1$H NMR (400 MHz, TFA salt, Methanol-d$_4$)δ 8.48 (d, J = 8.9 Hz, 1H), 7.57 (s, 1H), 7.40 (s, 1H), 7.38 (s, 1H), 4.76-4.68 (m, 4H), 4.36-4.25 (m, 1H), 4.13-4.02 (m, 1H), 3.88 (s, 3H), 3.59-3.38 (m, 4H), 3.01-2.84 (m, 2H), 2.21-2.08 (m, 2H), 1.97-1.79 (m, 2H), 1.25 (t, J = 7.2 Hz, 3H); 491 [M + H]$^+$ | 33 | 4.503 |
| 61 | 4-((5-cyano-4-(methylamino)-7H-pyrrolo[2,3-d]pyrimidine-2-yl)amino)-3-methoxy-N-(1-(oxetane-3-yl)piperidine-4-yl)benzylamide | $^1$H NMR (400 MHz, TFA salt, Methanol-d$_4$)δ 8.53 (d, J = 9.0 Hz, 1H), 7.59 (s, 1H), 7.41 (s, 1H), 7.39 (s, 1H), 4.76-4.68 (m, 4H), 4.36-4.27 (m, 1H), 4.15-4.03 (m, 1H), 3.89 (s, 3H), 3.51-3.39 (m, 2H), 3.06 (s, 3H), 3.00-2.86 (m, 2H), 2.22-2.11 (m, 2H), 1.95-1.82 (m, 2H); 477 [M + H]$^+$ | 33 | 4.270 |
| 62 | 2-((5-chloro-1-(2-methoxy ethyl)-1H-pyrazole-4-yl)amino)-4-(ethylamino)-7H-pyrrolo[2,3-d]pyrimidine-5-carbonitrile | $^1$H NMR (400 MHz, TFA salt, Methanol-d$_4$)δ 7.79 (s, 1H), 7.52 (s, 1H), 4.24 (t, J = 5.3 Hz, 2H), 3.69 (t, J = 5.2 Hz, 2H), 3.54-3.50 (m, 2H), 3.21 (s, 3H), 1.20 (t, J = 7.2 Hz, 3H); 361 [M + H]$^+$ | 32 | 4.953 |
| 63 | 4-((5-cyano-4-(methylamino)-7H-pyrrolo[2,3-d]pyrimidine-2-yl)amino)-2-fluoro-5-methoxy-N-(1-(oxetane-3-yl)pyrrolidine-1-yl)piperidine-4-yl)benzamide | $^1$H NMR (400 MHz, TFA salt, Methanol-d$_4$)δ 8.60 (d, J = 14.1 Hz, 1H), 7.70 (s, 1H), 7.30 (d, J = 6.6 Hz, 1H), 4.86 (m, 6H), 4.46 (br s, 1H), 4.25 (br s, 1H), 3.99 (s, 3H), 3.60 (br s, 1H), 3.17 (s, 3H), 3.08 (br s, 1H), 2.31 (m, 2H), 2.01 (br s, 2H); 495 [M + H]$^+$ | 59 | 4.560 |
| 64 | 4-((5-cyano-4-(ethylamino)-7H-pyrrolo[2,3-d]pyrimidine-2-yl)amino)-2-fluoro-5-methoxy-N-(1-(oxetane-3-yl)pyrrolidine-1-yl)piperidine-4-yl)benzamide | $^1$H NMR (400 MHz, TFA salt, Methanol-d$_4$)δ8.60 (d, J = 14.1 Hz, 1H), 7.69 (s, 1H), 7.28 (d, J = 6.6 Hz, 1H), 4.88 (m, 5H), 4.45 (br s, 1H), 4.23 (br s, 1H), 3.98 (s, 3H), 3.67 (q, J = 7.2 Hz, 2H), 3.62 (br s, 1H), 3.08 (br s, 2H), 2.33 (br s, 2H), 2.01 (br s, 2H), 1.39 (t, J = 7.2 Hz, 3H); 509 [M + H]$^+$ | 92 | 4.811 |
| 65 | 4-((5-cyano-4-(methylamino)-7H-pyrrolo[2,3-d]pyrimidine-2-yl)amino)-2-fluoro-5-methoxy-N-(1-methylpiperidine-4-yl)benzamide | $^1$H NMR (400 MHz, TFA salt, Methanol-d$_4$)δ8.66(dd, J = 14.3, 6.6 Hz, 1H), 7.69 (s, 1H), 7.31 (d, J = 6.6 Hz, 1H), 4.22 4.11 (m, 2H), 3.99 (s, 3H), 3.65 3.70 (m, 2H), 3.52 3.45 (m, 1H), 3.17 (s, 3H), 2.92 (d, J = 13.6 Hz, 3H), 2.32 2.25 (m, 2H), 1.95 1.84 (m, 2H); 453 [M + H]$^+$ | 62 | 4.574 |
| 66 | 4-((5-cyano-4-(ethylamino)-7H-pyrrolo[2,3-d]pyrimidine-2-yl)amino)-2-fluoro-5-methoxy-N-(1-methylpiperidine-4-yl)benzamide | $^1$H NMR (400 MHz, TFA salt, Methanol-d$_4$)δ8.708.60(m, 1H), 7.69 (s, 1H), 7.32(d, J = 6.6 Hz, 1H), 4.25 4.12 (m, 1H), 4.05 3.94 (m, 3H), 3.68 (dd, J = 14.3, 7.1 Hz, 2H), 3.63 3.56 (m, 2H), 3.25 3.12 (m, 2H), 2.92 (d, J = 13.9 Hz, 3H), 2.33 2.22 (m, | 50 | 4.844 |

TABLE 5-continued

| Example | Chemical Name | $^1$H NMR; MS(ESI) m/z | yield (%) | HPEC r.t. (min) (method) |
|---|---|---|---|---|
| | | 2H), 1.95 1.85 (m, 2H), 1.36 (t, J = 7.2 Hz, 3H); 467 [M + H]$^+$ | | |
| 67 | 4-((5-cyano-4-(methylamino)-7H-pyrrolo[2,3-d]pyrimidine-2-yl)amino)-2-fluoro-N-(1-isopropylpiperidine-4-yl)-5-methoxybenzamide | $^1$H NMR (400 MHz, TFA salt, Methanol-d$_4$) δ 8.53 (d, J = 14.28 Hz, 1H), 7.56 (s, 1H), 7.18 (d, J = 6.68 Hz, 1H), 4.08 (m, 2H), 3.87(s, 3H), 3.43 (m, 3H), 3.12 (m, 2H), 3.04 (s, 3H), 2.20 (m, 2H), 1.80 (m, 2H), 1.28 (s, 3H), 1.26 (s, 3H); 481 [M + H]$^+$ | 42 | 4.696 |
| 68 | 4-((5-cyano-4-(ethylamino)-7H-pyrrolo[2,3-d]pyrimidine-2-yl)amino)-2-fluoro-N-(1-isopropylpiperidine-4-yl)-5-methoxybenzamide | $^1$H NMR (400 MHz, DMSO-d$_4$) 12.37 (br, 1H), 8.54 (d, J = 13.7, 1H), 7.92 (s, 1H), 7.78 (m, 1H), 7.62 (s, 1H), 7.18 (d, J = 6.76, 1H), 6.54 (t, J = 5.72, 5.56, 1H), 3.93 (s, 3H), 3.70 (m, 1H), 3.56 (m, 2H), 2.74(m, 2H), 2.67(m, 1H), 2.18(m, 2H), 1.80(m, 2H), 1.50(m, 2H), 1.23 (t, J = 7.08, 7.08, 3H), 0.97(s, 3H), 0.95 (s, 3H); 495 [M + H]$^+$ | 42 | 4.943 |
| 69 | 2-((1-(2-hydroxyethyl)-1H-pyrazole-4-yl)amino)-4-(methylamino)-7H-pyrrolo[2,3-d]pyrimidine-5-carbonitrile | $^1$H NMR (400 MHz, TFA salt, DMSO-d$_6$)δ12.05(brs, 1H), 8.88(brs, 1H), 7.92(s, 1H), 7.77(d, J = 2.5 Hz, 1H), 7.54 (s, 1H), 6.40 (br s, 1H), 4.06 (t, J = 5.6 Hz, 2H), 3.70 (t, J = 5.6 Hz, 2H), 3.00 (s, 3H); 299 [M + H]$^+$ | 68 | 4.083 |
| 70 | 4-(ethylamino)-2-((1-(2-hydroxyethyl)-1H-pyrazole-4-yl)amino)-7H-pyrrolo[2,3-d]pyrimidine-5-carbonitrile | $^1$H NMR (400 MHz, TFA salt, DMSO-d$_6$)δ12.10(brs, 1H), 8.96(brs, 1H), 7.90(s, 1H), 7.79(s, 1H), 7.54(s, 1H), 6.44(brs, 1H), 4.07(t, J = 5.6 Hz, 2H), 3.71 (t, J = 5.5 Hz, 2H), 1.22 (t, J = 7.1 Hz, 3H); 313 [M + H]$^+$ | 56 | 4.238 |
| 71 | 2-((3-chloro-1-(2-cyanopropane-2-yl)-1H-pyrazole-4-yl)amino)-4-(methylamino)-7H-pyrrolo[2,3-d]pyrimidine-5-carbonitrile | $^1$H NMR (400 MHz, TFA salt, Methanol-d$_4$) δ 8.46 (s, 1H), 7.70 (s, 1H), 3.19 (s, 3H), 2.03 (s, 6H); 356 [M + H]$^+$ | 61 | 5.506 |
| 72 | 2-((3-chloro-1-(2-cyanopropane-2-yl)-1H-pyrazole-4-yl)amino)-4-(ethylamino)-7H-pyrrolo[2,3-d]pyrimidine-5-carbonitrile | $^1$H NMR (400 MHz, TFA salt, Methanol-d$_4$) δ 8.42 (s, 1H), 7.66 (s, 1H), 3.68 (q, J = 7.2 Hz, 2H), 2.03 (s, 6H), 1.37 (t, J = 7.2 Hz, 3H); 370 [M + H]$^+$ | 55 | 5.882 |
| 73 | 2-((5-chloro-1-(2-cyanopropane-2-yl)-1H-pyrazole-4-yl)amino)-4-(methylamino)-7H-pyrrolo[2,3-d]pyrimidine-5-carbonitrile | $^1$H NMR (400 MHz, TFA salt, Methanol-d$_4$) δ 8.01 (s, 1H), 7.40 (s, 1H), 2.97 (s, 3H), 1.93 (s, 6H); 356 [M + H]$^+$ | 42 | 5.269 |
| 74 | 2-((5-chloro-1-(2-cyanopropane-2-yl)-1H-pyrazole-4-yl)amino)-4-(ethylamino)-7H-pyrrolo[2,3-d]pyrimidine-5-carbonitrile | $^1$H NMR (400 MHz, TFA salt, Methanol-d$_4$) δ 7.89 (s, 1H), 7.52 (s, 1H), 3.54-3.49 (m, 2H), 1.96 (s, 6H), 1.20 (t, J = 7.5 Hz, 3H); 370 [M + H]$^+$ | 20 | 5.596 |
| 75 | (R)-2-((4-(2,4-dimethylpiperazine-1-carbonyl)-2-methoxyphenyl)amino)-4-(methylamino)-7H-pyrrolo[2,3-d]pyrimidine-5-carbonitrile | $^1$H NMR (400 MHz, TFA salt, Methanol-d$_4$) δ 8.70 (d, J = 8.3 Hz, 1H), 7.72 (s, 1H), 7.15 (s, 1H), 7.13 (d, J = 8.4 Hz, 1H), 4.01 (s, 3H), 3.51-3.48 (m, 3H), 3.24-3.12 (m, 7H), 2.95 (s, 3H), 1.47 (d, J = 7.2 Hz, 3H); 435 [M + H]$^+$ | 19 | 4.182 |
| 76 | (R)-2-((4-(2,4-dimethylpiperazine-1-carbonyl)-2-methoxyphenyl)amino)-4-(ethylamino)-7H-pyrrolo[2,3-d]pyrimidine-5-carbonitrile | $^1$H NMR (400 MHz, TFA salt, Methanol-d$_4$) δ 8.59 (d, J = 8.3 Hz, 1H), 7.73 (s, 1H), 7.15 (s, 1H), 7.12 (d, J = 8.3 Hz, 1H), 4.00 (s, 3H), 3.70-3.65 (m, 2H), 3.60-3.45 (m, 3H), 3.33-3.26 (m, 3H), 3.20-3.14 (m, 1H), 2.95 (s, 3H), 1.47 (d, J = 7.2 Hz, 3H), 1.37 (t, J = 7.2 Hz, 3H); 449 [M + H]$^+$ | 25 | 4.429 |

TABLE 5-continued

| Example | Chemical Name | $^1$H NMR; MS(ESI) m/z | yield (%) | HPEC r.t. (min) (method) |
|---|---|---|---|---|
| 77 | 2-((1-(2-cyanopropane-2-yl)-3,5-dimethyl-1H-pyrazole-4-yl)amino)-4-(methylamino)-7H-pyrrolo[2,3-d]pyrimidine-5-carbonitrile | $^1$H NMR (400 MHz, TFA salt, Methanol-d$_4$)δ 7.62 (s, 1H), 3.14 (s, 3H), 2.45 (s, 3H), 2.13 (s, 3H), 2.01(s, 6H); 350 [M + H]$^+$ | 6 | 4.753 |
| 78 | 2-((1-(2-cyanopropane-2-yl)-3,5-dimethyl-1H-pyrazole-4-yl)amino)-4-(ethylamino)-7H-pyrrolo[2,3-d]pyrimidine-5-carbonitrile | $^1$H NMR (400 MHz, TFA salt, Methanol-d$_4$)δ 7.65 (s, 1H), 3.71-3.60 (m, 2H), 2.45 (s, 3H), 2.13 (s, 3H), 2.01(s, 6H), 1.33-1.23 (m, 3H); 364 [M + H]$^+$ | 8 | 5.040 |
| 79 | (R)-2-((4-(2,4-dimethylpiperazine-1-carbonyl)-5-fluoro-2-methoxyphenyl)amino)-4-(ethylamino)-7H-pyrrolo[2,3-d]pyrimidine-5-carbonitrile | $^1$H NMR (400 MHz, TFA salt, Methanol-d$_4$)δ 8.57 (d, J = 12.84 Hz, 1H), 7.56 (s, 1H), 6.90 (d, J = 6.0 Hz, 1H), 3.88 (s, 3H), 3.71(m, 1H), 3.55 (m, 2H), 3.46 (m, 1H), 3.37 (m, 1H), 3.02 (m, 2H), 2.86 (s, 3H), 1.33 (s, 3H), 1.24 (t, J = 7.2, 7.16, 3H), 1.17(s, 2H); 467 [M + H]$^+$ | 51 | 4.742 |
| 80 | (R)-2-((4-(2,4-dimethylpiperazine-1-carbonyl)-5-fluoro-2-methoxyphenyl)amino)-4-(methylamino)-7H-pyrrolo[2,3-d]pyrimidine-5-carbonitrile | $^1$H NMR (400 MHz, TFA salt, Methanol-d$_4$)δ8.69(d, J = 12.9 Hz, 1H), 7.67 (s, 1H), 7.01 (d, J = 6.0 Hz, 1H), 3.99 (s, 3H), 3.92 3.77 (m, 1H), 3.72 3.40 (m, 4H), 3.40 3.31 (m, 2H), 3.21 3.09 (m, 4H), 2.96 (s, 3H), 1.44 (s, 3H); 453 [M + H]$^+$ | 24 | 1.66(B) |
| 81 | 4-((5-cyano-4-((1-methylcyclopropyl)amino)-7H-pyrrolo[2,3-]pyrimidine-2-yl)amino)-2-fluoro-5-methoxy-N-(1-(oxetane-3-yl)piperidine-4-yl)benzamide | $^1$H NMR (400 MHz, TFA salt, Methanol-d$_4$)δ 8.99 (d, J = 14.4 Hz, 1H), 7.72 (s, 1H), 7.36 (d, J = 6.7 Hz, 1H), 4.81 (m, 3H), 4.45 (br s, 1H), 4.24 (br s, 1H), 4.02 (s, 3H), 3.59 (br s, 2H), 3.08 (br s, 2H), 2.31 (br s, 2H), 2.02 (m, 2H), 1.61 (s, 3H), 1.30 (m, 1H), 1.05 (m, 2H), 0.97 (m, 2H); 535 [M + H]$^+$ | 29 | 4.913 |
| 82 | 4-((5-cyano-4-((1-methylcyclopropyl)amino)-7H-pyrrolo[2,3-d]pyrimidine-2-yl)amino)-2-fluoro-N-(1-isopropylpiperidine-4-yl)-5-methoxybenzamide | $^1$H NMR (400 MHz, TFA salt, Methanol-d$_4$)δ 8.92 (d, J = 14.2 Hz, 1H), 7.74 (s, 1H), 7.36 (d, J = 6.6 Hz, 1H), 4.20 (m, 1H), 4.03 (s, 3H), 3.58 (m, 3H), 3.26 (t, J = 12.3 Hz, 2H), 2.35 (m, 2H), 1.96 (m, 2H), 1.62 (s, 3H), 1.41 (d, J = 6.6 Hz, 6H), 1.07 (m, 2H), 0.99 (m, 2H); 521 [M + H]$^+$ | 64 | 5.069 |
| 83 | 4-((5-cyano-4-((1-methylcyclopropyl)amino)-7H-pyrrolo[2,3-d]pyrimidine-2-yl)amino)-2-fluoro-5-methoxy-N-(1-methylpiperidine-4-yl)benzamide | $^1$H NMR (400 MHz, TFA salt, Methanol-d$_4$)δ 8.91 (d, J = 14.2 Hz, 1H), 7.74 (s, 1H), 7.35 (d, J = 6.6 Hz, 1H), 4.20 (m, 1H), 4.02 (s, 3H), 3.63 (m, 2H), 3.26 (t, J = 11.5 Hz, 2H), 2.92(s, 3H), 2.31 (m, 2H), 1.98 (m, 2H), 1.62 (s, 3H), 1.06 (br s, 2H), 0.99 (br s, 2H); 493 [M + H]$^+$ | 62 | 4.951 |
| 84 | 2-((2-methoxy-4-(morpholine-4-carbonyl)phenyl)amino)-4-((tetrahydro-2H-pyran-4-yl)oxy)-7H-pyrrolo[2,3-d]pyrimidine-5-carbonitrile | $^1$H NMR (400 MHz, TFA salt, Methanol-d$_4$)δ 8.64 (d, J = 8.3 Hz, 1H), 7.72 (s, 1H), 7.11 (s, 1H), 7.08 (d, J = 8.3 Hz, 1H), 5.60 (m, 1H), 4.07 (m, 2H), 4.00 (s, 3H), 3.76 (m, 10), 2.19 (m, 2H), 1.96 (m, 2H); 479 [M + H]$^+$ | 32 | 6.179 |
| 85 | 2-((2-methoxy-4-(morpholine-4-carbonyl)phenyl)amino)-4-((tetrahydro-2H-pyran-4-yl)oxy)-7H-pyrrolo[2,3-d]pyrimidine-5-carbonitrile | 562 [M + H]$^+$ | 55 | 4.853 |
| 86 | 2-((2-methoxy-4-(morpholine-4-carbonyl)phenyl)amino)-4-((tetrahydrofuran-3-yl)oxy)-7H-pyrrolo[2,3-d]pyrimidine-5-carbonitrile | $^1$H NMR (400 MHz, TFA salt, Methanol-d$_4$)δ 8.62 (d, J = 8.3 Hz, 1H), 7.68 (s, 1H), 7.09 (s, 1H), 7.07 (d, J = 8.3 Hz, 1H), 5.78 (m, 1H), 4.14 (m, 1H), 4.05 (m, 2H), 3.99 (s, 3H), 3.96 (m, 1H), 3.7 (br s, 8H), 2.38 (m, 1H), 2.29 (m, 1H); 465 [M + H]$^+$ | 47 | 6.022 |

TABLE 5-continued

| Example | Chemical Name | ¹H NMR; MS(ESI) m/z | yield (%) | HPEC r.t. (min) (method) |
|---|---|---|---|---|
| 87 | 2-((2-methoxy-4-(4-morpholinopiperidine-1-carbonyl)phenyl)amino)-4-((tetrahydrofuran-3-yl)oxy)-7H-pyrrolo[2,3-d]pyrimidine-5-carbonitrile | 548 [M + H]⁺ | 16 | 4.779 |
| 88 | (S)-2-((2-methoxy-4-(morpholine-4-carbonyl)phenyl)amino)-4-((tetrahydrofuran-3-yl)oxy)-7H-pyrrolo[2,3-d]pyrimidine-5-carbonitrile | ¹H NMR (400 MHz, TFA salt, Methanol-d₄)δ 8.61 (d, J = 8.3 Hz, 1H), 7.69 (s, 1H), 7.09 (s, 1H), 7.07 (d, J = 8.3 Hz, 1H), 5.78 (m, 1H), 4.14 (m, 1H), 4.05 (m, 2H), 3.99 (s, 3H), 3.96 (m, 1H), 3.7 (br s, 8H), 2.29-2.38 (m, 2H); 465 [M + H]⁺ | 58 | 6.022 |
| 89 | (R)-2-((2-methoxy-4-(morpholine-4-carbonyl)phenyl)amino)-4-((tetrahydrofuran-3-yl)oxy)-7H-pyrrolo[2,3-d]pyrimidine-5-carbonitrile | ¹H NMR (400 MHz, TFA salt, Methanol-d₄)δ 8.60 (d, J = 8.3 Hz, 1H), 7.68 (s, 1H), 7.09 (s, 1H), 7.07 (d, J = 8.3 Hz, 1H), 5.78 (m, 1H), 4.14 (m, 1H), 4.06 (m, 2H), 3.99 (s, 3H), 3.97 (m, 1H), 3.7 (br s, 8H), 2.29-2.38 (m, 2H); 465 [M + H]⁺ | 75 | 6.020 |
| 90 | 4-isoprofoxy-2-((2-methoxy-4-(morpholine-4-carbonyl)phenyl)amino)-7H-pyrrolo[2,3-d]pyrimidine-5-carbonitrile | ¹H NMR (400 MHz, TFA salt, Methanol-d₄)δ 8.64 (d, J = 8.3 Hz, 1H), 7.67 (s, 1H), 7.09 (s, 1H), 7.07 (d, J = 8.4 Hz, 1H), 5.58 (m, 1H), 3.99 (s, 3H), 3.71 (br s, 8H), 1.48 (d, J = 6.2 Hz, 6H); 437 [M + H]⁺ | 37 | 6.392 |
| 91 | 4-isoprofoxy-2-((2-methoxy-4-(4-morpholinopiperidine-1-carbonyl)phenyl)amino)-7H-pyrrolo[2,3-d]pyrimidine-5-carbonitrile | 520 [M + H]⁺ | 44 | 4.774 |
| 92 | (S)-2-((5-fluoro-2-methoxy-4-(morpholine-4-carbonyl)phenyl)amino)-4-((tetrahydrofuran-3-yl)oxy)-7H-pyrrolo[2,3-d]pyrimidine-5-carbonitrile | ¹H NMR (400 MHz, TFA salt, DMSO-d₆)δ 12.69 (s, 1H), 8.43 (d, J = 12.1 Hz, 1H), 8.07 (d, J = 13.0 Hz, 2H), 7.05 (d, J = 6.2 Hz, 1H), 5.76 (m, 1H), 4.03 (m, 1H), 3.94 (m, 5H), 3.85 (m, 2H), 3.65 (br s, 5H), 3.56 (m, 2H), 2.35 (m, 1H), 2.15 (m, 1H); 483 [M + H]⁺ | 6 | 6.286 |
| 93 | (S)-2-((5-fluoro-2-methoxy-4-(4-morpholinopiperidine-1-carbonyl)phenyl)amino)-4-((tetrahydrofuran-3-yl)oxy)-7H-pyrrolo[2,3-d]pyrimidine-5-carbonitrile | 566 [M + H]⁺ | 42 | 4.677 |
| 94 | 2-((1-(2-cyanopropane-2-yl)-3-methyl-1H-pyrazole-4-yl)amino)-4-(1-methylcyclopropoxy)-7H-pyrrolo[2,3-d]pyrimidine-5-carbonitrile | ¹H NMR (400 MHz, TFA salt, Methanol-d₄)δ 8.13 (s, 1H), 7.48 (s, 1H), 2.15 (s, 3H), 1.86 (s, 6H), 1.64 (s, 3H), 0.94-0.92 (m, 2H), 0.73-0.71 (m, 2H); 377[M + H]⁺ | 33 | 6.680 |
| 95 | 2-((2-methoxy-4-(morpholine-4-carbonyl)phenyl)amino)-4-(1-methylcyclopropoxy)-7H-pyrrolo[2,3-d]pyrimidine-5-carbonitrile | ¹H NMR (400 MHz, TFA salt, DMSO-d₆)δ 12.53 (br, 1H), 8.54 (d, J = 8.3 Hz, 1H), 8.02 (d, J = 2.7 Hz, 1H), 7.90 (s, 1H), 7.08-7.04 (m, 2H), 3.92 (s, 3H), 3.70-3.46 (m, 8H), 1.71 (s, 3H), 1.02-0.84 (m, 4H); 449 [M + H]⁺ | 20 | 6.614 |
| 96 | 2-((5-chloro-1-((3S,4S)-3-fluoro-1-(oxetane-3-yl)piperidine-4-yl)-1H-pyrazole-4-yl)amino)(1-methylcyclopropoxy)-7H-pyrrolo[2,3-d]pyrimidine-5-carbonitrile | ¹H NMR (400 MHz, TFA salt, Methanol-d₄)δ 8.07 (s, 1H), 7.55 (s, 1H), 5.08-5.20 (m, 1H), 4.74-4.83 (m, 5H), 4.37 (m, 1H), 3.80 (m, 1H), 3.49 (m, 1H), 3.06 (m, 1H), 2.35 (m, 2H), 1.64 (s, 3H), 1.21 (br s, 1H), 0.97 (m, 2H), 0.71 (m, 2H); 487 [M + H]⁺ | 71 | 5.341 |
| 97 | 2-((5-fluoro-2-methoxy-4-(morpholine-4-carbonyl)phenyl)amino)-4- | ¹H NMR (400 MHz, TFA salt, DMSO-d₆)δ 12.62 (br, 1H), 8.58 (d, J = 12.4 Hz, 1H), 8.07 (s, 1H), 7.96 | 25 | 6.824 |

TABLE 5-continued

| Example | Chemical Name | $^1$H NMR; MS(ESI) m/z | yield (%) | HPEC r.t. (min) (method) |
|---|---|---|---|---|
| | (1-methyl cyclopropoxy)-7H-pyrrolo[2,3-d]pyrimidine-5-carbonitrile | (s, 1H), 7.04 (d, J = 6.2 Hz, 1H), 3.92 (s, 3H), 3.68-3.52 (m, 7H), 3.18-3.15 (m, 1H), 1.72 (s, 3H), 1.05-1.02 (m, 2H), 0.88-0.85 (m, 2H); 467 [M + H]$^+$ | | |
| 98 | (R)-2-((2-methoxy-4-(2-methylmorpholine-4-carbonyl)phenyl)amino)-4-(1-methylcyclopropoxy)-7H-pyrrolo[2,3d]carbonitrile | $^1$H NMR (400 MHz, TFA salt, Methanol-d$_4$)δ 8.83 (d, J = 8.3 Hz, 1H), 7.73 (s, 1H), 7.11 (s, 1H), 7.09 (d, J = 8.3 Hz, 1H), 4.02 (s, 3H), 3.92 (br s, 1H), 3.61 (br s, 2H), 1.81 (s, 3H), 1.24 (s, 4H), 1.10-1.21 (m, 5H), 0.92 (m, 2H); 463 [M + H]$^+$ | 32 | 6.842 |
| 99 | (S)-2-((2-methoxy-4-(2-methylmorpholine-4-carbonyl)phenyl)amino)-4-(1-methyl cyclopropoxy)-7H-pyrrolo[2,3-d]pyrimidine-5-carbonitrile | $^1$H NMR (400 MHz, TFA salt, Methanol-d$_4$)δ 8.66 (d, J = 8.3 Hz, 1H), 7.56 (s, 1H), 6.94 (s, 1H), 6.93 (d, J = 8.3 Hz, 1H), 4.47-4.07 (m, 1H), 4.28 (s, 3H), 3.81-3.55 (m, 2H), 3.51-3.35 (m, 2H), 3.08-2.44 (m, 2H), 1.64 (s, 3H), 1.01-0.90 (m, 5H), 0.76-0.73 (m, 2H); 463 [M + H]$^+$ | 21 | 6.847 |
| 100 | 2-((4-((2R,6S)-2,6-dimethylmorpholine-4-carbonyl)-2-methoxyphenyl)amino)-4-(1-methylcyclopropoxy)-7H-pyrrolo[2,3-d]pyrimidine-5-carbonitrile | $^1$H NMR (400 MHz, TFA salt, Methanol-d$_4$)δ 8.69 (d, J = 8.3 Hz, 1H), 7.58 (s, 1H), 6.96(s, 1H), 6.95 (d, J = 8.3 Hz, 1H), 4.49-4.21 (m, 1H), 3.78-3.40 (m, 3H), 3.07 (s, 3H), 2.93-2.34 (m, 2H), 1.67 (s, 3H), 1.04-0.97 (m, 8H), 0.79-0.76 (m, 2H); 477 [M + H]$^+$ | 20 | 7.083 |
| 101 | 2-((1-((3S,4S)-3-fluoro-1-(oxetane-3-yl)piperidine-4-yl)-1H-pyrazole-4-yl)amino)-4-(1-methylcyclopropoxy)-7H-pyrrolo[2,3-d]pyrimidine-5-carbonitrile | $^1$H NMR (400 MHz, TFA salt, Methanol-d$_4$)δ 8.10 (s, 1H), 7.70 (s, 1H), 7.54 (s, 1H), 4.99-5.12 (m, 1H), 4.71-4.89 (m, 4H), 4.56 (m, 1H), 4.30 (m, 1H), 3.70 (m, 1H), 3.45 (m, 1H), 3.09 (m, 1H), 2.95 (m, 1H), 2.36 (m, 2H), 1.71 (s, 3H), 1.00 (br s, 2H), 0.77 (br s, 2H); 453 [M + H]$^+$ | 53 | 5.089 |
| 102 | N$^2$-(5-chloro-1-((3S,4S)-3-fluoro-1-(oxetane-3-yl)piperidine-4-yl)-1H-pyrazole-4-yl)-N$^4$-ethyl-5-(trifluoromethyl)-7H-pyrrolo[2,3-d]pyrimidine-2,4-diamine | $^1$H NMR (400 MHz, TFA salt, Methanol-d$_4$)δ 8.00 (s, 1H), 7.49 (s, 1H), 5.08-5.24 (m, 1H), 4.86 (m, 3H), 4.79 (m, 3H), 4.18 (m, 3H), 3.67 (m, 3H), 2.85 (m, 1H), 2.79 (m, 1H), 2.46 (m, 1H), 2.33 (m, 1H), 1.29 (m, 3H); 503 [M + H]$^+$ | 22 | 4.897 |
| 103 | 2-(4-((4-(ethylamino)-5-(trifluoromethyl)-7H-pyrrolo[2,3-d]pyrimidine-2-yl)amino)-3-methyl-1H-pyrazole-1-yl)-2-methylpropanenitrile | $^1$H NMR (400 MHz, TFA salt, Methanol-d$_4$)δ 8.20 (s, 1H), 7.47 (s, 1H), 3.73 (q, J = 7.2 Hz, 2H), 2.28 (s, 3H), 2.03 (s, 6H), 1.33 (t, J = 7.2 Hz, 3H); 393 [M + H]$^+$ | 48 | 5.585 |
| 104 | (4-((4-(ethylamino)-5-(trifluoromethyl)-7H-pyrrolo[2,3-d]pyrimidine-2-yl)amino)-3-methoxyphenyl)(4-morpholinopiperidine-1-yl)methanone | 548 [M + H]$^+$ | 85 | 4.791 |
| 105 | (4-((4-(ethylamino)-5-(trifluoromethyl)-7H-pyrrolo[2,3-d]pyrimidine-2-yl)amino)-3-methoxyphenyl)(morpholino)methanone | $^1$H NMR (400 MHz, TFA salt, Methanol-d$_4$)δ 8.48 (d, J = 8.3 Hz, 1H), 7.54 (s, 1H), 7.16 (s, 1H), 7.11 (d, J = 8.3 Hz, 1H), 4.00 (s, 3H), 3.51-3.86 (m, 10H), 1.36 (t, J = 7.2 Hz, 3H); 465 [M + H]$^+$ | 56 | 5.595 |
| 106 | (4-(ethylamino)-5-(trifluoromethyl)-7H-pyrrolo[2,3-d]pyrimidine-2-yl)amino)-3-methoxyphenyl)(4-(4-methylpiperazine-1-yl)piperidine-1-yl)methanone | $^1$H NMR (400 MHz, TFA salt, Methanol-d$_4$)δ8.47 (d, J = 8.3 Hz, 1H), 7.57 (s, 1H), 7.18 (s, 1H), 7.13 (d, J = 8.3 Hz, 1H), 4.78 (m, 1H), 4.01 (s, 3H), 4.00 (s, 2H), 3.75 (q, J = 7.2 Hz, 2H), 3.50-3.68 (m, 8H), 3.45 (m, 1H), 2.98 (s, 4H), 2.18 (br s, 2H), 1.78 (m, 2H), 1.37 (t, J = 7.2 Hz, 3H); 561 [M + H]$^+$ | 60 | 4.587 |
| 107 | (4-((4-(ethylamino)-5-(trifluoromethyl)-7H-pyrrolo[2,3-d]pyrimidine- | $^1$H NMR (400 MHz, TFA salt, Methanol-d$_4$)δ 8.60 (d, J = 8.3 Hz, 1H), 7.53 (s, 1H), 7.21 (s, 1H), 7.18 | 32 | 4.768 |

TABLE 5-continued

| Example | Chemical Name | ¹H NMR; MS(ESI) m/z | yield (%) | HPEC r.t. (min) (method) |
|---|---|---|---|---|
| | 2-yl)amino)-3-methoxyphenyl)(4-methylpiperazine-1-yl)methanone | (d, J = 8.3 Hz, 1H), 4.51 (br s, 1H), 4.02 (s, 3H), 3.74 (q, J = 7.2 Hz, 2H), 3.54 (m, 4H), 3.23 (m, 2H), 2.98 (s, 3H), 1.37 (t, J = 7.2 Hz, 3H); 478 [M + H]⁺ | | |
| 108 | (R)-(4-((4-(ethylamino)-5-(trifluoromethyl)-7H-pyrrolo[2,3-d]pyrimidine-2-yl)amino)-3-methoxyphenyl)(2-methylmorpholino)methanone | ¹H NMR (400 MHz, TFA salt, Methanol-d₄) δ 8.39 (d, J = 8.3 Hz, 1H), 7.47 (s, 1H), 7.07 (s, 1H), 7.02 (d, J = 8.3 Hz, 1H), 4.37 (br s, 1H), 3.91 (s, 3H), 3.81 (m, 1H), 3.65 (q, J = 7.2 Hz, 3H), 3.51 (br s, 2H), 3.01 (br s, 1H), 1.27 (t, J = 7.2 Hz, 3H), 1.12 (br s, 4H); 479 [M + H]⁺ | 49 | 5.877 |
| 109 | ((2R,6S)-2,6-dimethylmorpholino)((4-((4-(ethylamino)-5-(trifluoromethyl)-7H-pyrrolo[2,3-d]pyrimidine-2-yl)amino)-3-methoxyphenyl)methanone | ¹H NMR (400 MHz, TFA salt, Methanol-d₄) δ 8.49 (d, J = 8.3 Hz, 1H), 7.56 (s, 1H), 7.16 (s, 1H), 7.11 (d, J = 8.3 Hz, 1H), 4.50 (br s, 1H), 4.01 (s, 3H), 3.75 (q, J = 7.2 Hz, 2H), 3.65 (br s, 3H), 2.94 (br s, 1H), 2.68 (br s, 1H), 1.37 (t, J = 7.2 Hz, 3H), 1.10 (m, 6H); 493 [M + H]⁺ | 46 | 6.110 |
| 110 | (4,4-difluoropiperidine-1-yl)(4-((4-(ethylamino)-5-(trifluoromethyl)-7H-pyrrolo[2,3-d]pyrimidine-2-yl)amino)-3-methoxyphenyl)methanone | ¹H NMR (400 MHz, TFA salt, Methanol-d₄) δ 8.51 (d, J = 8.3 Hz, 1H), 7.56 (s, 1H), 7.20 (s, 1H), 7.15 (d, J = 8.3 Hz, 1H), 4.01 (s, 3H), 3.83 (br s, 4H), 3.75 (q, J = 7.2 Hz, 2H), 2.09 (br s, 4H), 1.37 (t, J = 7.2 Hz, 3H); 499 [M + H]⁺ | 44 | 6.287 |
| 111 | (S)-(4-((4-(ethylamino)-5-(trifluoromethyl)-7H-pyrrolo[2,3-d]pyrimidine-2-yl)amino)-3-methoxyphenyl)(2-methylmorpholino)methanone | ¹H NMR (400 MHz, TFA salt, Methanol-d₄) δ 8.51 (d, J = 8.3 Hz, 1H), 7.55 (s, 1H), 7.16 (s, 1H), 7.11 (d, J = 8.3 Hz, 1H), 4.47 (br s, 1H), 4.01 (s, 3H), 3.91 (br s, 1H), 3.74 (q, J = 7.2 Hz, 2H), 3.61 (br s, 3H), 3.01 (br s, 1H), 1.37 (t, J = 7.2 Hz, 3H), 1.19 (br s, 4H); 479 [M + H]⁺ | 43 | 5.881 |
| 112 | (3-methoxy-4-((4-(methylamino)-5-(trifluoromethyl)-7H-pyrrolo[2,3-d]pyrimidine-2-yl)amino)phenyl)(morpholino)methanone | ¹H NMR (400 MHz, TFA salt, Methanol-d₄) δ 8.60 (br s, 1H), 7.69 (s, 1H), 7.26 (s, 1H), 7.20 (d, J = 8.3 Hz, 1H), 4.09 (s, 3H), 3.79 (br s, 6H), 3.70 (m, 2H), 3.34 (s, 3H); 451 [M + H]⁺ | 89 | 5.267 |
| 113 | 2-(4-((4-(ethylamino)-5-(trifluoromethyl)-7H-pyrrolo[2,3-d]pyrimidine-2-yl)amino)-3-methyl-1H-pyrazole-1-yl)-2-methylpropaneamide | ¹H NMR (400 MHz, TFA salt, Methanol-d₄) δ 8.07 (s, 1H), 7.47 (s, 1H), 3.74 (q, J = 7.0 Hz, 2H), 2.25 (s, 3H), 1.86 (s, 6H), 1.34 (t, J = 7.2 Hz, 3H); 411 [M + H]⁺ | 40 | 4.951 |
| 114 | N⁴-ethyl-N²-(2-methoxy-4-(4-methylpiperazine-1-yl)phenyl)-5-(trifluoromethyl)-7H-pyrrolo[2,3-d]pyrimidine-2,4-diamine | ¹H NMR (400 MHz, TFA salt, Methanol-d₄) δ 7.86 (d, J = 7.8 Hz, 1H), 7.50 (s, 1H), 6.81 (s, 1H), 6.70 (d, J = 7.8 Hz, 1H), 3.94 (s, 3H), 3.90 (m, 2H), 3.72 (q, J = 7.2 Hz, 2H), 3.64 (m, 2H), 3.48 (m, 2H), 3.11 (m, 2H), 3.00 (s, 3H), 1.34 (t, J = 7.1 Hz, 3H); 450 [M + H]⁺ | 34 | 4.592 |
| 115 | N⁴-ethyl-N²-(2-methoxy-4-morpholinophenyl)-5-(trifluoromethyl)-7H-pyrrolo[2,3-d]pyrimidine-2,4-diamine | ¹H NMR (400 MHz, TFA salt, Methanol-d₄) δ 7.84 (d, J = 6.6 Hz, 1H), 7.47 (s, 1H), 6.82 (s, 1H), 6.73 (d, J = 8.0 Hz, 1H), 3.93 (s, 3H), 3.91 (m, 4H), 3.74 (q, J = 7.2 Hz, 2H), 3.29 (br s, 4H), 1.34 (t, J = 7.2 Hz, 3H); 436 [M + H]⁺ | 52 | 5.395 |
| 116 | 4-((4-(ethylamino)-5-(trifluoromethyl)-7H-pyrrolo[2,3-d]pyrimidine-2-yl)amino)-2-fluoro-5-methoxy-N-(1-(oxetanepiperidine-4-yl)benzamide | ¹H NMR (400 MHz, TFA salt, Methanol-d₄) δ 8.67 (d, J = 14.1 Hz, 1H), 7.50 (s, 1H), 7.35 (d, J = 6.6 Hz, 1H), 4.84 (m, 2H), 4.45 (br s, 1H), 4.23 (br s, 1H), 4.01 (s, 3H), 3.74 (q, J = 7.2 Hz, 2H), 3.59 (br s, 2H), 3.07 (br s, 2H), 2.31 (m, 2H), 2.01 (br s, 2H), 1.37 (t, J = 7.2 Hz, 3H); 552 [M + H]⁺ | 37 | 5.252 |
| 117 | N²-(5-chloro-1-((3S,4S)-3-fluoro-1-(oxetane-3-yl)piperidine-4-yl)-1H- | ¹H NMR (400 MHz, TFA salt, Methanol-d₄) δ 8.23 (s, 1H), 7.58 (s, 1H), 5.11-5.27 (m, 1H), 4.81-4.89 (m, | 31 | 4.880 |

TABLE 5-continued

| Example | Chemical Name | ¹H NMR; MS(ESI) m/z | yield (%) | HPEC r.t. (min) (method) |
|---|---|---|---|---|
| | pyrazole-4-yl)-N⁴-cyclopropyl-5-(trifluoromethyl)-7H-pyrrolo[2,3-d]pyrimidine-2,4-diamine | 5H), 4.34 (m, 1H), 3.80 (m, 1H), 3.48 (m, 1H), 3.10 (m, 1H), 2.98 (m, 2H), 2.34-2.51 (m, 2H), 1.07 (br s, 2H), 0.84 (br s, 2H); 515 [M + H]⁺ | | |
| 118 | (4-((4-(cyclopropylamino)-5-(trifluoromethyl)-7H-pyrrolo[2,3-d]pyrimidine-2-yl)amino)-3-methoxyphenyl)(morpholino)methanone | ¹H NMR (400 MHz, TFA salt, Methanol-d₄)δ 8.74 (d, J = 8.3 Hz, 1H), 7.63 (s, 1H), 7.17 (s, 1H), 7.12 (d, J = 8.3 Hz, 1H), 4.04 (s, 3H), 3.73 (br s, 8H), 2.97 (m, 1H), 1.14 (m, 2H), 0.89 (m, 2H); 477 [M + H]⁺ | 62 | 5.586 |
| 119 | (4-((4-(cyclopropylamino)-5-(trifluoromethyl)-7H-pyrrolo[2,3-d]pyrimidine-2-yl)amino)-3-methoxyphenyl)(4-methylpiperazine-1-yl)methanone | ¹H NMR (400 MHz, TFA salt, Methanol-d₄)δ 8.81 (d, J = 8.4 Hz, 1H), 7.63 (s, 1H), 7.22 (s, 1H), 7.18 (d, J = 8.4 Hz, 1H), 4.05 (s, 3H), 3.15-3.56 (m, 8H), 2.98 (s, 4H), 1.14 (m, 2H), 0.89 (m, 2H); 490 [M + H]⁺ | 33 | 4.746 |
| 120 | (4-((4-(cyclopropylamino)-5-(trifluoromethyl)-7H-pyrrolo[2,3-d]pyrimidine-2-yl)amino)-3-methoxyphenyl)(4-(4-methylpiperazine-1-yl)piperidine-1-yl)methanone | ¹H NMR (400 MHz, TFA salt, Methanol-d₄)δ 7.72 (d, J = 8.3 Hz, 1H), 7.65 (s, 1H), 7.18 (s, 1H), 7.12 (d, J = 8.3 Hz, 1H), 4.80 (m, 1H), 4.03 (s, 3H), 3.61 (m, 10H), 3.15 (m, 1H), 2.98 (s, 5H), 2.22 (br s, 2H), 1.77 (m, 2H), 1.16 (m, 2H), 0.92 (m, 2H); 573 [M + H]⁺ | 78 | 4.542 |
| 121 | (3-methoxy-4-((4-((1-methylcyclopropyl)amino)-5-(trifluoromethyl)-7H-pyrrolo[2,3-d]pyrimidine-2-yl)amino)phenyl)(4-methylpiperazine-1-yl)methanone | 1H NMR (400 MHz,, TFA salt, Methanol-d₄) δ 8.84 (d, J = 8.32 Hz, 1H), 7.60 (d, J = 1.28 Hz, 1H), 7.24 (d, J = 1.48 Hz, 1H), 7.19 (dd, J = 8.36, 1.68 Hz, 1H), 4.45 (br s, 2H), 4.06 (s, 3H), 3.57 (br s, 4H), 3.24 (br s, 2H), 2.99 (s, 3H), 1.61 (s, 3H), 1.09-1.00 (m, 4H); 504 [M + H]⁺ | 46 | 4.882 |
| 122 | (3-methoxy-4-((4-((1-methylcyclopropyl)amino)-5-(trifluoromethyl)-7H-pyrrolo[2,3-d]pyrimidine-2-yl)amino)phenyl)(4-(4-methylpiperazine-1-yl)piperidine-1-yl)methanol | 587 [M + H]⁺ | 58 | 4.668 |
| 123 | (R)-(2,4-dimethylpiperazine-1-yl)(2-fluoro-5-methoxy-4-((4-(methylamino)-5-(trifluoromethyl)-7H-pyrrolo[2,3-d]pyrimidine-2-yl)amino)phenyl)methanone | ¹H NMR (400 MHz, TFA salt, DMSO-d₆) δ 12.12 (d, J = 2.3 Hz, 1H), 9.59 (s, 1H), 8.70 8.60 (m, 1H), 7.65 (d, J = 19.3 Hz, 2H), 6.98 (s, 1H), 6.12 6.05 (m, 1H), 5.05 4.90 (m, 1H), 4.61 4.50 (m, 1H), 4.15 4.05 (m, 1H), 3.93 (s, 3H), 3.72 3.60 (m, 2H), 3.25 3.10 (m, 2H), 3.04 (d, J = 4.5 Hz, 3H), 2.84 (s, 3H), 1.38 1.27 (m, 3H); 496 [M + H] | 46 | 1.82(B) |
| 124 | (3-methoxy-4-((4-((tetrahydrofuran-3-yl)oxy)-5-(trifluoromethyl)-7H-pyrrolo[2,3-d]pyrimidine-2-yl)amino)phenyl)(morpholino)methanone | ¹H NMR (400 MHz, TFA salt, DMSO-d₆) δ 12.27 (d, J = 1.8 Hz, 1H), 8.44 (d, J = 8.2 Hz, 1H), 7.95 (s, 1H), 7.71 (s, 1H), 7.08 (s, 1H), 7.04 (d, J = 8.2 Hz, 1H) 4.05 4.00 (m, 1H), 3.92 (s, 3H), 3.85 3.81 (m, 4H), 3.65 3.58 (m, 4H), 3.58 3.47 (m, 4H), 2.32 2.22 (m, 1H), 2.10 2.03 (m, 1H); 508 [M + H]⁺ | 38 | 2.04(B) |
| 125 | (3-methoxy-4-((4-((tetrahydrofuran-3-yl)oxy)-5-(trifluoromethyl)-7H-pyrrolo[2,3-d]pyrimidine-2-yl)amino)phenyl)-methylpiperazine-1-yl)methanone | ¹H NMR (400 MHz, TFA salt, DMSO-d₆) δ 12.28 (s, 1H), 8.48 (d, J = 8.1 Hz, 1H), 7.95 (s, 1H), 7.70 (s, 1H), 7.11 7.09 (m, 2H), 4.40 4.11 (m, 1H), 4.05 3.98 (m, 2H), 3.93 (s, 3H), 3.85 3.81 (m, 4H), 3.40 3.21 (m, 3H), 3.20 3.02 (m, 3H), 2.84 (s, 3H), 2.30 2.23 (m, 1H), 2.10 2.05 (m, 1H); 521 [M + H]⁺ | 40 | 2.37(B) |
| 126 | (3-methoxy-4-((4-((tetrahydrofuran-3-yl)oxy)-5- | 604 [M + H]⁺ | 47 | 1.92(B) |

TABLE 5-continued

| Example | Chemical Name | ¹H NMR; MS(ESI) m/z | yield (%) | HPEC r.t. (min) (method) |
|---|---|---|---|---|
| | (trifluoromethyl)-7H-pyrrolo[2,3-d]pyrimidine-2-yl)amino)phenyl)-(4-methylpiperazine-1-yl)piperidine-1-yl)methanone | | | |
| 127 | N-(5-chloro-1-((3S,4S)-3-fluoro-1-(oxetane-3-yl)piperidine-4-yl)-1H-pyrazole-4-yl)-4-((tetrahydrofuranoxy)-5-(trifluoromethyl)-7H-pyrrolo[2,3-d]pyrimidine-2-amine | ¹H NMR (400 MHz, TFA salt, DMSO-d₆) δ 12.05 (d, J = 2.0 Hz, 1H), 8.60 (s, 1H), 7.89 (s, 1H), 7.57 (s, 1H), 5.57 (s, 1H), 5.10 4.90 (m, 2H), 4.68 4.51 (m, 5H), 3.97 3.84 (m, 2H), 3.82 3.72 (m, 4H), 3.15 2.90 (m, 2H), 2.27 2.12 (m, 2H), 2.12 1.95 (m, 2H); 546 [M + H]⁺ | 14 | 4.883 |
| 128 | 2-((6-chloro-2-methyl-1-oxoisoindol-5-yl)amino)-4-(ethylamino)-7H-pyrrolo[2,3-d]pyrimidine-5-carbonitrile | ¹H NMR (400 MHz, TFA salt, DMSO-d₆) δ 12.34(s, 1H), 8.64 (s, 1H), 7.96 (s, 1H), 7.91 (s, 1H), 7.70 (s, 1H), 6.52 (m, 1H), 4.45 (s, 2H), 3.55 (m, 2H), 3.06 (s, 3H), 1.24 (t, J = 7.1 Hz, 3H); 382[M + H]⁺ | 27 | 5.83(A) |
| 129 | 4-(ethylamino)-2-((2-methyl-1-oxoisoindol-5-yl)amino)-7H-pyrrolo[2,3-d]pyrimidine-5-carbonitrile | ¹H NMR (400 MHz, TFA salt, DMSO-d₆) δ 12.25(s, 1H), 9.40 (s, 1H), 8.19 (s, 1H), 7.87 (s, 1H), 7.80 (d, J = 8.4 Hz, 1H), 7.51 (d, J = 8.4 Hz, 1H), 6.38 (m, 1H), 4.39 (s, 2H), 3.55 (m, 2H), 3.03 (s, 3H), 1.26 (t, J = 7.1 Hz, 3H); 348[M + H]⁺ | 23 | 5.12(A) |
| 130 | 4-(ethylamino)-2-((6-methoxy-2-methyl-1-oxoisoindol-5-yl)amino)-7H-pyrrolo[2,3-d]pyrimidine-5-carbonitrile | ¹H NMR (400 MHz, TFA salt, DMSO-d₆) δ 12.34(s, 1H), 8.77 (s, 1H), 7.91 (s, 1H), 7.69 (s, 1H), 7.22 (s, 1H), 6.50 (m, 1H), 4.38 (s, 2H), 3.98 (s, 3H), 3.59 (m, 2H), 3.06 (s, 3H), 1.26 (t, J = 7.1 Hz, 3H); 378[M + H]⁺ | 44 | 5.37(A) |
| 131 | 4-(ethylamino)-2-((6-methoxy-2,2,4-trimethyl-3-oxo-3,4-dihydro-2H-benzo[b][1,4]oxazine-7-yl)amino)-7H-pyrrolo[2,3-d]pyrimidine-5-carbonitrile | ¹H NMR (400 MHz, TFA salt, DMSO-d₆) δ 8.20 (s, 1H), 7.88 (s, 1H), 7.64 (brs, 1H), 6.83(s, 1H), 6.63 (brs, 1H), 3.93 (s, 3H), 3.56 (m, 2H), 3.31 (s, 3H), 1.38 (s, 6H), 1.24 (t, J = 7.1 Hz, 3H); 422[M + H]⁺ | 62 | 5.79(A) |
| 132 | 2-((2-(2-cyanopropane-2-yl)-4-methylthiazole-5-yl)amino)-4-(ethyl amino)-7H-pyrrolo[2,3-d]pyrimidine-5-carbonitrile | NMR (400 MHz, TFA salt, DMSO-d₆) δ 7.43 (s, 1H), 7.29 (s, 1H), 6.58(brs, 1H), 3.82 (q, J = 7.1 Hz, 2H), 2.47 (s, 3H), 1.84 (s, 6H), 1.40 (t, J = 7.1 Hz, 3H); 367[M + H]⁺ | 43 | 6.23(A) |
| 133 | 5-((4-(ethylamino)-5-(trifluoromethyl)-7H-pyrrolo[2,3-d]pyrimidine-2-yl)amino)-6-methoxy-2-methylisoindolin-1-one | ¹H NMR (400 MHz, TFA salt, MeOD-d₄) δ 8.62 (s 1H), 7.46 (s, 1H), 7.28 (s, 1H), 4.33 (s, 2H), 3.95 (s, 3H), 3.65 (q, J = 7.2 Hz, 2H), 3.10 (s, 3H), 1.30 (t, J = 7.2 Hz, 3H); 421[M + H]⁺ | 32 | 5.95(A) |
| 134 | 6-((4-(ethylamino)-5-(trifluoromethyl)-7H-pyrrolo[2,3-d]pyrimidine-2-yl)amino)-5-methoxy-2-methylisoindolin-1-one | ¹H NMR (400 MHz, TFA salt, MeOD-d₄) δ 8.64 (s 1H), 7.47 (s, 1H), 7.20 (s, 1H), 4.38 (s, 2H), 3.97 (s, 3H), 3.67 (q, J = 7.2 Hz, 2H), 3.11 (s, 3H), 1.29 (t, J = 7.2 Hz, 3H); 421[M + H]⁺ | 30 | 5.50(A) |
| 135 | 6-chloro-5-((4-(ethylamino)-5-(trifluoromethyl)-7H-pyrrolo[2,3-d]pyrimidine-2-yl)amino)-2-methyl isoindolin-1-one | ¹H NMR (400 MHz, TFA salt, MeOD-d₄) δ 8.73 (s 1H), 7.70 (s, 1H), 7.40 (s, 1H), 4.39 (s, 2H), 3.60 (q, J = 7.2 Hz, 2H), 3.10 (s, 3H), 1.26 (t, J = 7.2 Hz, 3H); 425[M + H]⁺ | 49 | 6.71(A) |
| 136 | 5-((4-(ethylamino)-5-(trifluoromethyl)-7H-pyrrolo[2,3-d]pyrimidine-2-yl)amino)-2-methylisoindolin-1-one | ¹H NMR (400 MHz, TFA salt, MeOD-d₄) δ 8.01 (s 1H), 7.64-7.59 (m, 2H), 7.36 (s, 1H), 4.40 (s, 2H), 3.62 (q, J = 7.2 Hz, 2H), 3.10 (s, 3H), 1.27 (t, J = 7.2 Hz, 3H); 391[M + H]⁺ | 49 | 5.70(A) |
| 137 | 7-((4-(ethylamino)-5-(trifluoromethyl)-7H-pyrrolo[2,3-d]pyrimidine- | ¹H NMR (400 MHz, TFA salt, MeOD-d₄) δ 7.97 (s, 1H), 7.40 (s, 1H), 6.73 (s, 1H), 3.88 (s, 3H), 3.64 (q, J = 7.2 | 45 | 6.23(A) |

TABLE 5-continued

| Example | Chemical Name | $^1$H NMR; MS(ESI) m/z | yield (%) | HPEC r.t. (min) (method) |
|---|---|---|---|---|
| | 2-yl)amino)-6-methoxy-2,2,4-trimethyl-2H-benzo[1,4]oxazine-3(4H)-one | Hz, 2H), 3.30 (s, 3H), 1.36 (s, 6H), 1.27 (t, J = 7.2 Hz, 3H); 465 [M + H]$^+$ | | |

<Experimental Example 1> Evaluation of Enzyme Activity of the Compound of the Invention The following experiment was performed to evaluate the inhibitory activity of the compounds of Examples 1~137 against LRRK2 kinase.

First, a recombinant LRRK2 kinase (Signal Chem, Richmond, BC, Canada), 0.2 ug/ul LRRKtide (Signal Chem, Richmond, BC, Canada) and 25 μmol/L ATP (Invitrogen, Carlsbad, Calif.) were added to kinase reaction buffer (40 mmol/L Tris-HCl, 10 mmol/L MgCl$_2$ and 0.1 μg/μL BSA (bovine serum albumin)), which was loaded in a 384-well plate.

Next, the compounds of Examples 1~137 were added thereto at the final concentrations of 50 uM, 5 uM, 500 nM, 50 nM, 5 nM, 500 pM, 50 pM, 5 pM, and 0.5 pM respectively, followed by reaction in a 30° C. incubator for 2 hours. Upon completion of the reaction, an equal amount of Kinase-Glo (Promega, Madison, Wis.) solution was added thereto, followed by reaction for 40 minutes. A detection solution was added thereto, followed by further reaction at room temperature for 30 minutes. Then, IC$_{50}$ of kinase was calculated by measuring the amount of luciferase using a microplate ELISA reader (Bio-Tek).

The calculated IC$_{50}$ values of kinase were sorted as follows and presented in Table 6 below:
Grade A: less than 10 nM,
Grade B: 10~100 nM, and
Grade C: more than 100 nM.

TABLE 6

| Example | Enzyme activity LRRK2(nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | B |
| 15 | A |
| 16 | A |
| 17 | — |
| 18 | B |
| 19 | B |
| 20 | A |
| 21 | A |
| 22 | B |
| 23 | A |
| 24 | A |
| 25 | A |
| 26 | A |
| 27 | A |
| 28 | B |
| 29 | B |
| 30 | B |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | B |
| 45 | B |
| 46 | A |
| 47 | A |
| 48 | C |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | B |
| 61 | B |
| 62 | A |
| 63 | A |
| 64 | A |
| 65 | A |
| 66 | B |
| 67 | A |
| 68 | A |
| 69 | A |
| 70 | A |
| 71 | A |
| 72 | A |
| 73 | A |
| 74 | A |
| 75 | A |
| 76 | A |
| 77 | C |
| 78 | C |
| 79 | A |
| 80 | B |
| 81 | B |
| 82 | B |
| 83 | A |
| 84 | A |
| 85 | A |
| 86 | A |
| 87 | A |

TABLE 6-continued

| Example | Enzyme activity LRRK2(nM) |
|---|---|
| 88 | A |
| 89 | A |
| 90 | A |
| 91 | A |
| 92 | A |
| 93 | A |
| 94 | A |
| 95 | A |
| 96 | A |
| 97 | A |
| 98 | B |
| 99 | A |
| 100 | B |
| 101 | A |
| 102 | B |
| 103 | A |
| 104 | A |
| 105 | B |
| 106 | A |
| 107 | A |
| 108 | B |
| 109 | C |
| 110 | C |
| 111 | B |
| 112 | B |
| 113 | NA |
| 114 | NA |
| 115 | NA |
| 116 | NA |
| 117 | B |
| 118 | A |
| 119 | NA |
| 120 | NA |
| 121 | NA |
| 122 | NA |
| 123 | NA |
| 124 | B |
| 125 | NA |
| 126 | NA |
| 127 | B |
| 128 | C |
| 129 | NA |
| 130 | A |
| 131 | B |
| 132 | B |
| 133 | A |
| 134 | C |
| 135 | C |
| 136 | B |
| 137 | C |

<Experimental Example 2> Investigation of Inhibition of Phosphorylation in LRRK2 Expressing Cell Line by the Compounds of the Invention To evaluate the activity of the pyrrolo-pyrimidine derivative compound compounds of the present invention to inhibit phosphorylation in LRRK2 expressing cell line, the following experiment was performed. Particularly, the inhibition of phosphorylation by the compounds of Examples 32, 33, 34, 35, 36, 47, 49, 50, 52, 94, 95 and 96 in NIH-3T3 cell line known as a cell line expressing LRRK2 was investigated.

First, NIH-3T3 cell line was seeded in a 12-well plate at the density of $1 \times 10^5$/cells/1 ml/well, and the cells were allowed to attach the plate for one day. Each compound of Example 32, 33, 34, 35, 36, 47, 49, 50, 52, 94, 95 or 96 was added thereto at the final concentration of 100 nM and DMSO was added thereto at the concentration of 0.1%, followed by culture in a 37° C. $CO_2$ incubator for 24 hours. The culture medium was discarded and the plate was washed with PBS twice. 2× sample buffer (62.5 mM Tris-HCl pH 6.8, 5% SDS, 10% Glycerol, 5% beta-mercaptoethanol, 0.02% Bromophenol blue) was added to the plate (100 μl/well) and then cells were recovered. The cells were left at 75° C. for 5 minutes, followed by Western blotting.

Western blotting was performed as follows. The cells were loaded in Mini-PROTEAN® TGX™ Precast Gels (15 μl/well), followed by electrophoresis (10 minutes at 85 V, 50 minutes at 110 V). Then, protein was transferred onto PVDF membrane (18 hours at 35 V). The membrane was blocked with 5% skim milk (1 hour at room temperature), to which the primary antibody (p-LRRK2, LRRK2 or GAPDH) was added, followed by reaction at 4° C. for 18 hours. The primary antibody was washed with TBST buffer and then the secondary antibody (goat anti-rabbit IgG-HRP) was added thereto, followed by reaction at room temperature for 2 hours. Upon completion of the reaction, the membrane was washed with TBST buffer. The membrane was reacted with SuperSignal™ West Pico Chemiluminescent Substrate, followed by detection with LAS4000.

FIG. 1 is a photograph illustrating the inhibition of LRRK2 phosphorylation in NIH-3T3 cell line by the compounds of the present invention.

As shown in FIG. 1, when the compounds of the present were treated, the amount of detectable P-LRRK2 was significantly low, compared with when the compounds were not treated. The result indicates that the compounds of the present invention can inhibit the LRRK2 phosphorylation effectively.

Therefore, the pyrrolo-pyrimidine derivative compound of the present invention can inhibit phosphorylation of intracellular LRRK2 efficiently, so that it can be effectively used as a pharmaceutical composition for the prevention or treatment of Parkinson's disease and brain cancer.

<Experimental Example 3> Investigation of Inhibition of Phosphorylation in Brain Tumor Cell Line by the Compounds of the Invention To investigate the therapeutic effect of the pyrrolo-pyrimidine derivative compound compounds of the present invention on brain cancer, the inhibition of phosphorylation by the compounds of Examples 10, 34, 35, 37, 44, 46, 51, 52, 53, 89, 96 and 97 in NCC01, a brain tumor patient derived cell line, was first examined. The inhibition of phosphorylation by the compounds of Examples 32, 33, 36, 47, 49, 94 and 95 in 448T, another brain tumor patient derived cell line, was also examined. The results in NCC01 cell line are shown in FIG. 2 and the results in 448T cell line are shown in FIG. 3.

Particularly, NCC01 cells line and 448T cell line (Samsung Medical Center, Seoul, Korea) were seeded in 60 mm dishes at the density of $0.75 \sim 1 \times 10^6$, and the cells were allowed to attach the dish for one day. Each compound of the present invention was added thereto at the final concentration of 100 nM, followed by culture in a 37° C. $CO_2$ incubator for 24 hours. The culture medium was collected to recover the cells. 30~50 μL of RIPA buffer (50 mM Tris-HCl pH 7.5, 150 mM NaCl, 1% sodium deoxycholate, 0.1% SDS, 1% Triton X-100) containing protease inhibitor (Roche, 11836153001) and phosphatase inhibitor (GenDEPOT, P3200-001) was added to the cells. The mixture was placed on ice, followed by vortexing three times every 10 minutes. Centrifugation was performed (13000 rpm, 4° C., 20 minutes) and the supernatant was transferred. Protein concentration was measured by BCA assay, and 5× sample buffer (1M Tris-HCl pH 6.8, 10% SDS, 50% Glycerol, 5% beta-mercaptoethanol, 1% Bromophenol blue) was added thereto (final concentration of sample buffer: 1×), which stood at 75° C. for 5 minutes, followed by Western blotting.

Western blotting was performed as follows. The cells were loaded in Gel (20 μg/well), followed by electrophoresis (1 hour at 100 V). Then, protein was transferred onto PVDF membrane (100 minutes at 250 mA). The membrane was blocked with 5% skim milk (1 hour at room temperature), to which the primary antibody (p-LRRK2, LRRK2 or beta-actin) was added, followed by reaction at 4° C. for 18 hours. The primary antibody was washed with TBST buffer (10 minutes, 6 times) and then the secondary antibody (goat anti-rabbit IgG-HRP) was added thereto, followed by reaction at room temperature for 1 hour. Upon completion of the reaction, the membrane was washed with TBST buffer (10 minutes, 6 times). The membrane was reacted in GE ECL plus solution, followed by detection with X-ray film.

FIG. 2 is a photograph illustrating the inhibition of LRRK2 phosphorylation in NCC01 cell line by the compounds of the present invention.

FIG. 3 is a photograph illustrating the inhibition of LRRK2 phosphorylation in 448T cell line by the compounds of the present invention.

As shown in FIG. 2 and FIG. 3, when the compounds of the present invention were treated, LRRK2 phosphorylation in NCC01 and 448T cell lines derived from brain tumor patients was inhibited. When the compounds of the present were treated, the amount of detectable P-LRRK2 was significantly low, compared with when the compounds were not treated. The result indicates that the compounds of the present invention can inhibit the LRRK2 phosphorylation effectively.

Therefore, the pyrrolo-pyrimidine derivative compound of the present invention can inhibit phosphorylation of LRRK2 in cancer inducing cells efficiently, so that it can be effectively used as a pharmaceutical composition for the prevention or treatment of LRRK2 related disease.

<Experimental Example 4> Evaluation of Kinase Inhibitory Activity of the Compound of the Invention The following experiment was performed to evaluate the activity of the compounds of the present invention to inhibit many enzymes.

Particularly, the compounds of Examples 8, 64 and 104 were selected among all of those compounds of the invention. DiscoverX Co. was asked to measure the enzyme (kinase) selectivity, and the experiment was performed using scanMAX™ Kinase assay panel.

Wherein, the concentration of the drug treated to each enzyme was 1 uM in DMSO and the control percentage (% control) was determined by the following Equation 1. The results are shown in Table 7 below.

(example compound−positive control)/(negative control−positive control)×100  [Equation 1]

Herein, the positive control indicates the compound showing the % control of 0%, and the negative control indicates DMSO showing the % control of 100%. The enzyme selectivity in the present invention is defined as follows: When the % control for each enzyme is less than 35% (<35%), it is judged that the compound has the activity to the corresponding enzyme.

TABLE 7

| | Example 1 | Example 52 | Example 64 | Example 104 |
|---|---|---|---|---|
| AAK1 | 78.0 | 9.6 | 59 | 90 |
| ABL1(E255K)-phosphorylated | 91.0 | 0.6 | 100 | 100 |
| ABL1(F317I)-nonphosphorylated | 99.0 | 25 | 96 | 56 |
| ABL1(F317I)-phosphorylated | 54.0 | 7.6 | 78 | 29 |
| ABL1(F317L)-nonphosphorylated | 91.0 | 16 | 95 | 74 |
| ABL1(F317L)-phosphorylated | 48.0 | 0 | 55 | 35 |
| ABL1(H396P)-nonphosphorylated | 81.0 | 0.55 | 76 | 96 |
| ABL1(H396P)-phosphorylated | 94.0 | 0.9 | 73 | 74 |
| ABL1(M351T)-phosphorylated | 62.0 | 2.6 | 100 | 100 |
| ABL1(Q252H)-nonphosphorylated | 57.0 | 1.1 | 100 | 99 |
| ABL1(Q252H)-phosphorylated | 100.0 | 0.25 | 88 | 82 |
| ABL1(T315I)-nonphosphorylated | 83.0 | 0 | 100 | 100 |
| ABL1(T315I)-phosphorylated | 59.0 | 0.05 | 94 | 98 |
| ABL1(Y253F)-phosphorylated | 97.0 | 1 | 86 | 86 |
| ABL1-nonphosphorylated | 92.0 | 6.4 | 62 | 91 |
| ABL1-phosphorylated | 88.0 | 1.8 | 68 | 63 |
| ABL2 | 99.0 | 34 | 100 | 100 |
| ACVR1 | 97.0 | 73 | 100 | 100 |
| ACVR1B | 86.0 | 92 | 97 | 100 |
| ACVR2A | 100.0 | 98 | 100 | 100 |
| ACVR2B | 100.0 | 85 | 100 | 100 |
| ACVRL1 | 88.0 | 100 | 88 | 97 |
| ADCK3 | 94.0 | 98 | 93 | 100 |
| ADCK4 | 100.0 | 76 | 100 | 100 |
| AKT1 | 83.0 | 100 | 100 | 100 |
| AKT2 | 86.0 | 100 | 100 | 94 |
| AKT3 | 70.0 | 4.5 | 100 | 100 |
| ALK | 13.0 | 3 | 10 | 0.35 |
| ALK(C1156Y) | 9.3 | 0.8 | 18 | 16 |
| ALK(L1196M) | 33.0 | 9.9 | 20 | 0.75 |
| AMPK-alpha1 | 87.0 | 4.3 | 100 | 100 |
| AMPK-alpha2 | 85.0 | 9.9 | 100 | 100 |
| ANKK1 | 82.0 | 15 | 64 | 95 |
| ARK5 | 88.0 | 2.5 | 45 | 99 |
| ASK1 | 57.0 | 1.8 | 41 | 82 |
| ASK2 | 56.0 | 11 | 79 | 92 |
| AURKA | 99.0 | 0.85 | 90 | 87 |
| AURKB | 73.0 | 14 | 100 | 90 |
| AURKC | 100.0 | 7.1 | 100 | 100 |
| AXL | 90.0 | 0 | 70 | 69 |
| BIKE | 62.0 | 0 | 87 | 100 |
| BLK | 100.0 | 2.2 | 86 | 100 |
| BMPR1A | 94.0 | 100 | 100 | 100 |
| BMPR1B | 98.0 | 22 | 95 | 83 |
| BMPR2 | 79.0 | 0.65 | 100 | 100 |
| BMX | 93.0 | 39 | 92 | 94 |
| BRAF | 69.0 | 99 | 100 | 100 |
| BRAF(V600E) | 95.0 | 100 | 100 | 100 |
| BRK | 93.0 | 24 | 74 | 64 |
| BRSK1 | 97.0 | 96 | 95 | 100 |
| BRSK2 | 89.0 | 70 | 100 | 100 |
| BTK | 72.0 | 9.1 | 100 | 100 |
| BUB1 | 36.0 | 0.2 | 16 | 95 |
| CAMK1 | 59.0 | 6.8 | 68 | 72 |
| CAMK1B | 45.0 | 64 | 18 | 21 |
| CAMK1D | 50.0 | 14 | 65 | 66 |
| CAMK1G | 74.0 | 34 | 70 | 94 |
| CAMK2A | 60.0 | 28 | 64 | 39 |
| CAMK2B | 62.0 | 57 | 79 | 81 |
| CAMK2D | 82.0 | 65 | 72 | 66 |
| CAMK2G | 88.0 | 53 | 91 | 80 |
| CAMK4 | 99.0 | 55 | 24 | 27 |
| CAMKK1 | 81.0 | 21 | 21 | 14 |
| CAMKK2 | 65.0 | 5.7 | 30 | 20 |
| CASK | 69.0 | 91 | 100 | 100 |
| CDC2L1 | 100.0 | 84 | 98 | 99 |
| CDC2L2 | 91.0 | 100 | 100 | 98 |
| CDC2L5 | 82.0 | 97 | 100 | 100 |
| CDK11 | 87.0 | 100 | 97 | 96 |
| CDK2 | 94.0 | 96 | 97 | 98 |
| CDK3 | 100.0 | 76 | 100 | 93 |
| CDK4 | 61.0 | 100 | 100 | 100 |
| CDK4-cyclinD1 | 74.0 | 59 | 53 | 55 |
| CDK4-cyclinD3 | 96.0 | 100 | 70 | 53 |
| CDK5 | 96.0 | 63 | 100 | 100 |
| CDK7 | 67.0 | 19 | 91 | 48 |
| CDK8 | 100.0 | 76 | 84 | 86 |

TABLE 7-continued

| | Example 1 | Example 52 | Example 64 | Example 104 |
|---|---|---|---|---|
| CDK9 | 96.0 | 84 | 100 | 100 |
| CDKL1 | 89.0 | 46 | 83 | 88 |
| CDKL2 | 99.0 | 73 | 100 | 100 |
| CDKL3 | 93.0 | 100 | 85 | 100 |
| CDKL5 | 76.0 | 100 | 100 | 100 |
| CHEK1 | 85.0 | 26 | 100 | 100 |
| CHEK2 | 7.7 | 0 | 12 | 12 |
| CIT | 86.0 | 76 | 96 | 100 |
| CLK1 | 1.8 | 0.6 | 0.05 | 0.15 |
| CLK2 | 5.9 | 2.6 | 0.85 | 0.9 |
| CLK3 | 70.0 | 27 | 61 | 4 |
| CLK4 | 3.4 | 1.4 | 2.8 | 4.1 |
| CSF1R | 89.0 | 0 | 69 | 88 |
| CSF1R-autoinhibited | 46.0 | 0 | 52 | 100 |
| CSK | 99.0 | 33 | 85 | 85 |
| CSNK1A1 | 19.0 | 1.6 | 4 | 56 |
| CSNK1A1L | 34.0 | 0.85 | 1.8 | 15 |
| CSNK1D | 5.0 | 1 | 0.6 | 2.6 |
| CSNK1E | 12.0 | 0.15 | 0.1 | 4.2 |
| CSNK1G1 | 95.0 | 6.4 | 42 | 73 |
| CSNK1G2 | 58.0 | 0.1 | 7.5 | 100 |
| CSNK1G3 | 58.0 | 0.15 | 1.9 | 90 |
| CSNK2A1 | 59.0 | 24 | 27 | 73 |
| CSNK2A2 | 76.0 | 11 | 73 | 95 |
| CTK | 98.0 | 47 | 100 | 100 |
| DAPK1 | 8.5 | 12 | 14 | 49 |
| DAPK2 | 11.0 | 12 | 6.8 | 35 |
| DAPK3 | 12.0 | 8.4 | 11 | 56 |
| DCAMKL1 | 57.0 | 34 | 33 | 49 |
| DCAMKL2 | 91.0 | 76 | 82 | 93 |
| DCAMKL3 | 98.0 | 91 | 92 | 90 |
| DDR1 | 94.0 | 50 | 100 | 100 |
| DDR2 | 96.0 | 20 | 100 | 100 |
| DLK | 74.0 | 21 | 100 | 100 |
| DMPK | 100.0 | 3.4 | 100 | 100 |
| DMPK2 | 90.0 | 81 | 94 | 100 |
| DRAK1 | 37.0 | 0.3 | 29 | 49 |
| DRAK2 | 13.0 | 1.2 | 8.1 | 15 |
| DYRK1A | 4.1 | 0.15 | 0.5 | 0.05 |
| DYRK1B | 13.0 | 0.55 | 0 | 0 |
| DYRK2 | 22.0 | 0.8 | 9.9 | 25 |
| EGFR | 91.0 | 31 | 81 | 82 |
| EGFR(E746-A750del) | 97.0 | 59 | 100 | 100 |
| EGFR(G719C) | 82.0 | 71 | 97 | 96 |
| EGFR(G719S) | 82.0 | 57 | 100 | 100 |
| EGFR(L747-E749del, A750P) | 98.0 | 38 | 97 | 99 |
| EGFR(L747-S752del, P753S) | 100.0 | 49 | 100 | 98 |
| EGFR(L747-T751del, Sins) | 61.0 | 68 | 95 | 100 |
| EGFR(L858R) | 96.0 | 41 | 95 | 89 |
| EGFR(L858R, T790M) | 54.0 | 2.3 | 48 | 55 |
| EGFR(L861Q) | 100.0 | 53 | 94 | 99 |
| EGFR(S752-I759del) | 76.0 | 94 | 96 | 100 |
| EGFR(T790M) | 61.0 | 1.3 | 36 | 41 |
| EIF2AK1 | 64.0 | 86 | 86 | 90 |
| EPHA1 | 93.0 | 58 | 100 | 100 |
| EPHA2 | 97.0 | 79 | 99 | 100 |
| EPHA3 | 92.0 | 18 | 89 | 92 |
| EPHA4 | 93.0 | 75 | 100 | 100 |
| EPHA5 | 87.0 | 79 | 100 | 100 |
| EPHA6 | 93.0 | 43 | 100 | 100 |
| EPHA7 | 97.0 | 20 | 100 | 94 |
| EPHA8 | 97.0 | 86 | 100 | 93 |
| EPHB1 | 100.0 | 41 | 100 | 100 |
| EPHB2 | 99.0 | 70 | 71 | 91 |
| EPHB3 | 93.0 | 95 | 100 | 100 |
| EPHB4 | 95.0 | 48 | 100 | 100 |
| EPHB6 | 84.0 | 3.7 | 100 | 95 |
| ERBB2 | 79.0 | 100 | 99 | 100 |
| ERBB3 | 68.0 | 100 | 100 | 100 |
| ERBB4 | 99.0 | 45 | 100 | 100 |
| ERK1 | 88.0 | 42 | 68 | 100 |
| ERK2 | 86.0 | 54 | 82 | 100 |
| ERK3 | 89.0 | 54 | 91 | 95 |
| ERK4 | 95.0 | 100 | 93 | 92 |
| ERK5 | 72.0 | 13 | 41 | 18 |
| ERK8 | 100.0 | 62 | 98 | 100 |
| ERN1 | 57.0 | 28 | 89 | 83 |
| FAK | 55.0 | 0.3 | 1.1 | 3.8 |
| FER | 15.0 | 0.25 | 2.2 | 3 |
| FES | 61.0 | 1.3 | 22 | 36 |
| FGFR1 | 97.0 | 42 | 100 | 100 |
| FGFR2 | 95.0 | 26 | 95 | 96 |
| FGFR3 | 100.0 | 9.8 | 94 | 100 |
| FGFR3(G697C) | 97.0 | 11 | 100 | 100 |
| FGFR4 | 89.0 | 31 | 95 | 38 |
| FGR | 94.0 | 10 | 100 | 100 |
| FLT1 | 99.0 | 6.2 | 100 | 100 |
| FLT3 | 86.0 | 0.05 | 99 | 65 |
| FLT3(D835H) | 92.0 | 0.1 | 33 | 21 |
| FLT3(D835V) | 58.0 | 0 | 11 | 0 |
| FLT3(D835Y) | 82.0 | 0 | 18 | 14 |
| FLT3(ITD) | 83.0 | 0 | 42 | 21 |
| FLT3(ITD, D835V) | 51.0 | 0 | 14 | 15 |
| FLT3(ITD, F691L) | 47.0 | 0.7 | 42 | 79 |
| FLT3(K663Q) | 92.0 | 0.1 | 70 | 64 |
| FLT3(N841I) | 90.0 | 0 | 85 | 51 |
| FLT3(R834Q) | 65.0 | 7.8 | 100 | 100 |
| FLT3-autoinhibited | 45.0 | 0.3 | 81 | 76 |
| FLT4 | 100.0 | 0.6 | 96 | 97 |
| FRK | 97.0 | 49 | 100 | 77 |
| FYN | 100.0 | 19 | 100 | 100 |
| GAK | 11.0 | 5.8 | 0.85 | 1 |
| GCN2(Kin.Dom.2, S808G) | 93.0 | 33 | 79 | 64 |
| GRK1 | 72.0 | 36 | 85 | 67 |
| GRK2 | 97.0 | 45 | 81 | 96 |
| GRK3 | 99.0 | 53 | 93 | 97 |
| GRK4 | 92.0 | 1.6 | 100 | 100 |
| GRK7 | 71.0 | 65 | 60 | 78 |
| GSK3A | 100.0 | 12 | 100 | 100 |
| GSK3B | 79.0 | 50 | 92 | 83 |
| HASPIN | 63.0 | 100 | 97 | 100 |
| HCK | 95.0 | 11 | 100 | 100 |
| HIPK1 | 61.0 | 18 | 19 | 13 |
| HIPK2 | 47.0 | 13 | 27 | 14 |
| HIPK3 | 64.0 | 6.2 | 24 | 16 |
| HIPK4 | 95.0 | 39 | 81 | 45 |
| HPK1 | 79.0 | 4.3 | 100 | 100 |
| HUNK | 5.3 | 51 | 0 | 0.7 |
| ICK | 73.0 | 71 | 97 | 96 |
| IGF1R | 82.0 | 19 | 85 | 12 |
| IKK-alpha | 57.0 | 3.4 | 100 | 93 |
| IKK-beta | 75.0 | 9.7 | 100 | 92 |
| IKK-epsilon | 98.0 | 9.9 | 100 | 95 |
| INSR | 48.0 | 0.35 | 28 | 7.1 |
| INSRR | 61.0 | 6.5 | 42 | 3.2 |
| IRAK1 | 75.0 | 1.4 | 100 | 100 |
| IRAK3 | 90.0 | 3.9 | 49 | 26 |
| IRAK4 | 92.0 | 0.2 | 100 | 100 |
| ITK | 99.0 | 9.7 | 100 | 100 |
| JAK1(JH1domain-catalytic) | 92.0 | 44 | 100 | 100 |
| JAK1(JH2domain-pseudokinase) | 14.0 | 0 | 7.1 | 55 |
| JAK2(JH1domain-catalytic) | 83.0 | 0 | 100 | 100 |
| JAK3(JH1domain-catalytic) | 64.0 | 0 | 100 | 100 |
| JNK1 | 0.0 | 0 | 0.8 | 25 |
| JNK2 | 0.1 | 0 | 0.6 | 23 |
| JNK3 | 0.0 | 0 | 0.15 | 18 |
| KIT | 48.0 | 0.15 | 4.8 | 56 |
| KIT(A829P) | 60.0 | 11 | 93 | 100 |
| KIT(D816H) | 77.0 | 8.1 | 91 | 100 |
| KIT(D816V) | 89.0 | 0.15 | 50 | 99 |
| KIT(L576P) | 41.0 | 0 | 5.9 | 47 |
| KIT(V559D) | 38.0 | 0 | 2.1 | 46 |
| KIT(V559D, T670I) | 73.0 | 0.4 | 47 | 87 |
| KIT(V559D, V654A) | 76.0 | 0.9 | 44 | 94 |
| KIT-autoinhibited | 59.0 | 0.1 | 55 | 74 |
| LATS1 | 100.0 | 35 | 67 | 100 |
| LATS2 | 61.0 | 11 | 98 | 87 |
| LCK | 100.0 | 19 | 100 | 100 |
| LIMK1 | 100.0 | 98 | 100 | 100 |
| LIMK2 | 94.0 | 65 | 100 | 99 |
| LKB1 | 91.0 | 31 | 79 | 87 |
| LOK | 95.0 | 74 | 100 | 100 |
| LRRK2 | 0.0 | 0 | 1.8 | 1.2 |
| LRRK2(G2019S) | 0.0 | 2.6 | 1.9 | 2 |

TABLE 7-continued

| | Example 1 | Example 52 | Example 64 | Example 104 |
|---|---|---|---|---|
| LTK | 6.8 | 3.4 | 5.2 | 3.7 |
| LYN | 90.0 | 36 | 95 | 100 |
| LZK | 81.0 | 16 | 100 | 100 |
| MAK | 95.0 | 71 | 100 | 100 |
| MAP3K1 | 100.0 | 81 | 94 | 83 |
| MAP3K15 | 35.0 | 27 | 94 | 61 |
| MAP3K2 | 85.0 | 0.05 | 100 | 92 |
| MAP3K3 | 98.0 | 0.1 | 92 | 87 |
| MAP3K4 | 100.0 | 77 | 100 | 97 |
| MAP4K2 | 75.0 | 1.2 | 44 | 69 |
| MAP4K3 | 97.0 | 3.3 | 100 | 100 |
| MAP4K4 | 82.0 | 18 | 100 | 100 |
| MAP4K5 | 89.0 | 30 | 100 | 100 |
| MAPKAPK2 | 4.6 | 70 | 17 | 24 |
| MAPKAPK5 | 16.0 | 72 | 31 | 51 |
| MARK1 | 91.0 | 36 | 100 | 100 |
| MARK2 | 100.0 | 9.5 | 92 | 81 |
| MARK3 | 100.0 | 29 | 100 | 86 |
| MARK4 | 84.0 | 37 | 100 | 100 |
| MAST1 | 100.0 | 74 | 100 | 72 |
| MEK1 | 89.0 | 0.1 | 94 | 86 |
| MEK2 | 93.0 | 0.3 | 85 | 83 |
| MEK3 | 4.3 | 0.8 | 14 | 12 |
| MEK4 | 0.0 | 0 | 1.5 | 16 |
| MEK5 | 47.0 | 0.05 | 33 | 74 |
| MEK6 | 43.0 | 19 | 33 | 92 |
| MELK | 78.0 | 6.3 | 71 | 79 |
| MERTK | 96.0 | 0 | 100 | 93 |
| MET | 89.0 | 21 | 100 | 100 |
| MET(M1250T) | 100.0 | 28 | 100 | 100 |
| MET(Y1235D) | 82.0 | 31 | 100 | 100 |
| MINK | 50.0 | 6.4 | 80 | 91 |
| MKK7 | 48.0 | 6.1 | 92 | 100 |
| MKNK1 | 62.0 | 100 | 100 | 100 |
| MKNK2 | 31.0 | 5.5 | 36 | 39 |
| MLCK | 96.0 | 9 | 86 | 92 |
| MLK1 | 81.0 | 0.5 | 46 | 66 |
| MLK2 | 90.0 | 4.4 | 97 | 96 |
| MLK3 | 78.0 | 3.1 | 76 | 86 |
| MRCKA | 100.0 | 100 | 100 | 100 |
| MRCKB | 100.0 | 89 | 100 | 100 |
| MST1 | 93.0 | 17 | 100 | 100 |
| MST1R | 88.0 | 78 | 96 | 95 |
| MST2 | 92.0 | 15 | 95 | 71 |
| MST3 | 86.0 | 25 | 91 | 84 |
| MST4 | 69.0 | 28 | 100 | 100 |
| MTOR | 100.0 | 66 | 100 | 100 |
| MUSK | 97.0 | 100 | 94 | 94 |
| MYLK | 0.0 | 0.55 | 3.3 | 0.95 |
| MYLK2 | 88.0 | 100 | 100 | 100 |
| MYLK4 | 90.0 | 82 | 65 | 89 |
| MYO3A | 68.0 | 3.9 | 93 | 78 |
| MYO3B | 84.0 | 10 | 35 | 19 |
| NDR1 | 84.0 | 42 | 100 | 94 |
| NDR2 | 98.0 | 31 | 100 | 100 |
| NEK1 | 94.0 | 80 | 99 | 93 |
| NEK10 | 53.0 | 0.95 | 13 | 100 |
| NEK11 | 70.0 | 100 | 100 | 100 |
| NEK2 | 97.0 | 70 | 83 | 74 |
| NEK3 | 70.0 | 96 | 94 | 82 |
| NEK4 | 75.0 | 100 | 100 | 100 |
| NEK5 | 98.0 | 99 | 94 | 95 |
| NEK6 | 95.0 | 93 | 99 | 100 |
| NEK7 | 100.0 | 97 | 100 | 94 |
| NEK9 | 100.0 | 73 | 100 | 99 |
| NIK | 3.7 | 7.4 | 16 | 16 |
| NIM1 | 77.0 | 100 | 100 | 100 |
| NLK | 98.0 | 75 | 76 | 69 |
| OSR1 | 21.0 | 0.45 | 5.6 | 7.5 |
| p38-alpha | 94.0 | 91 | 95 | 96 |
| p38-beta | 98.0 | 92 | 100 | 100 |
| p38-delta | 100.0 | 76 | 92 | 95 |
| p38-gamma | 70.0 | 77 | 100 | 89 |
| PAK1 | 100.0 | 75 | 66 | 71 |
| PAK2 | 95.0 | 45 | 68 | 71 |
| PAK3 | 68.0 | 17 | 85 | 100 |
| PAK4 | 79.0 | 3.4 | 100 | 100 |
| PAK6 | 76.0 | 8.3 | 82 | 91 |
| PAK7 | 91.0 | 0.25 | 85 | 85 |
| PCTK1 | 77.0 | 100 | 100 | 100 |
| PCTK2 | 98.0 | 88 | 100 | 99 |
| PCTK3 | 96.0 | 81 | 99 | 94 |
| PDGFRA | 15.0 | 9.7 | 91 | 88 |
| PDGFRB | 84.0 | 0.35 | 51 | 60 |
| PDPK1 | 81.0 | 70 | 100 | 100 |
| PFCDPK1(*P. falciparum*) | 87.0 | 52 | 100 | 100 |
| PFPK5(*P. falciparum*) | 76.0 | 100 | 100 | 100 |
| PFTAIRE2 | 97.0 | 90 | 100 | 99 |
| PFTK1 | 97.0 | 100 | 100 | 96 |
| PHKG1 | 13.0 | 11 | 2.3 | 1 |
| PHKG2 | 14.0 | 5.2 | 3.6 | 9.3 |
| PIK3C2B | 89.0 | 91 | 75 | 75 |
| PIK3C2G | 99.0 | 72 | 96 | 86 |
| PIK3CA | 87.0 | 60 | 93 | 99 |
| PIK3CA(C420R) | 94.0 | 63 | 94 | 91 |
| PIK3CA(E542K) | 74.0 | 77 | 97 | 83 |
| PIK3CA(E545A) | 94.0 | 71 | 84 | 90 |
| PIK3CA(E545K) | 80.0 | 68 | 91 | 90 |
| PIK3CA(H1047L) | 100.0 | 70 | 95 | 88 |
| PIK3CA(H1047Y) | 100.0 | 62 | 85 | 96 |
| PIK3CA(I800L) | 100.0 | 0.1 | 90 | 72 |
| PIK3CA(M1043I) | 94.0 | 37 | 96 | 84 |
| PIK3CA(Q546K) | 75.0 | 85 | 88 | 87 |
| PIK3CB | 96.0 | 100 | 100 | 92 |
| PIK3CD | 99.0 | 9.4 | 86 | 78 |
| PIK3CG | 76.0 | 8.5 | 84 | 87 |
| PIK4CB | 61.0 | 60 | 71 | 99 |
| PIKFYVE | 73.0 | 65 | 100 | 100 |
| PIM1 | 85.0 | 57 | 84 | 80 |
| PIM2 | 78.0 | 63 | 100 | 100 |
| PIM3 | 98.0 | 49 | 78 | 73 |
| PIP5K1A | 99.0 | 2.5 | 100 | 100 |
| PIP5K1C | 1.0 | 0 | 4.5 | 100 |
| PIP5K2B | 100.0 | 0.45 | 58 | 100 |
| PIP5K2C | 4.5 | 0 | 9.1 | 77 |
| PKAC-alpha | 100.0 | 100 | 100 | 100 |
| PKAC-beta | 89.0 | 95 | 100 | 100 |
| PKMYT1 | 99.0 | 89 | 94 | 100 |
| PKN1 | 100.0 | 67 | 96 | 95 |
| PKN2 | 53.0 | 78 | 100 | 100 |
| PKNB(*M. tuberculosis*) | 90.0 | 1.1 | 82 | 83 |
| PLK1 | 14.0 | 100 | 1.6 | 65 |
| PLK2 | 81.0 | 93 | 36 | 100 |
| PLK3 | 57.0 | 99 | 6.8 | 89 |
| PLK4 | 17.0 | 0 | 1.1 | 1.7 |
| PRKCD | 100.0 | 81 | 100 | 100 |
| PRKCE | 100.0 | 100 | 100 | 100 |
| PRKCH | 93.0 | 100 | 100 | 100 |
| PRKCI | 96.0 | 89 | 67 | 53 |
| PRKCQ | 95.0 | 47 | 100 | 100 |
| PRKD1 | 5.7 | 12 | 0.45 | 11 |
| PRKD2 | 28.0 | 9.1 | 0 | 16 |
| PRKD3 | 39.0 | 0.7 | 0 | 17 |
| PRKG1 | 83.0 | 79 | 94 | 84 |
| PRKG2 | 100.0 | 94 | 96 | 91 |
| PRKR | 95.0 | 42 | 93 | 85 |
| PRKX | 82.0 | 89 | 68 | 81 |
| PRP4 | 100.0 | 19 | 83 | 89 |
| PYK2 | 25.0 | 1.2 | 9.8 | 2.8 |
| QSK | 79.0 | 87 | 98 | 97 |
| RAF1 | 95.0 | 100 | 100 | 100 |
| RET | 97.0 | 0 | 99 | 98 |
| RET(M918T) | 94.0 | 0 | 91 | 96 |
| RET(V804L) | 79.0 | 0 | 43 | 89 |
| RET(V804M) | 89.0 | 0 | 52 | 87 |
| RIOK1 | 100.0 | 0.7 | 90 | 100 |
| RIOK2 | 47.0 | 1.1 | 18 | 75 |
| RIOK3 | 97.0 | 0.4 | 94 | 100 |
| RIPK1 | 94.0 | 14 | 100 | 100 |
| RIPK2 | 100.0 | 61 | 100 | 100 |
| RIPK4 | 72.0 | 1.6 | 94 | 0.6 |
| RIPK5 | 10.0 | 3.7 | 13 | 18 |
| ROCK1 | 64.0 | 28 | 100 | 100 |
| ROCK2 | 56.0 | 23 | 100 | 100 |

TABLE 7-continued

| | Example 1 | Example 52 | Example 64 | Example 104 |
|---|---|---|---|---|
| ROS1 | 56.0 | 23 | 31 | 22 |
| RPS6KA4(Kin.Dom.1-N-terminal) | 92.0 | 68 | 86 | 100 |
| RPS6KA4(Kin.Dom.2-C-terminal) | 0.2 | 2.2 | 0.05 | 18 |
| RPS6KA5(Kin.Dom.1-N-terminal) | 94.0 | 100 | 100 | 100 |
| RPS6KA5(Kin.Dom.2-C-terminal) | 12.0 | 24 | 33 | 83 |
| RSK1(Kin.Dom.1-N-terminal) | 98.0 | 2.4 | 88 | 89 |
| RSK1(Kin.Dom.2-C-terminal) | 59.0 | 52 | 61 | 61 |
| RSK2(Kin.Dom.1-N-terminal) | 68.0 | 0.55 | 99 | 100 |
| RSK2(Kin.Dom.2-C-terminal) | 66.0 | 100 | 63 | 71 |
| RSK3(Kin.Dom.1-N-terminal) | 90.0 | 4.3 | 96 | 100 |
| RSK3(Kin.Dom.2-C-terminal) | 23.0 | 28 | 33 | 66 |
| RSK4(Kin.Dom.1-N-terminal) | 79.0 | 7.1 | 95 | 95 |
| RSK4(Kin.Dom.2-C-terminal) | 77.0 | 75 | 91 | 97 |
| S6K1 | 70.0 | 52 | 90 | 80 |
| SBK1 | 72.0 | 21 | 100 | 100 |
| SGK | 48.0 | 18 | 100 | 100 |
| SgK110 | 100.0 | 32 | 100 | 100 |
| SGK2 | 82.0 | 74 | 100 | 100 |
| SGK3 | 63.0 | 70 | 88 | 87 |
| SIK | 97.0 | 78 | 100 | 100 |
| SIK2 | 100.0 | 33 | 100 | 100 |
| SLK | 100.0 | 13 | 98 | 97 |
| SNARK | 77.0 | 0.95 | 77 | 91 |
| SNRK | 64.0 | 7.6 | 54 | 69 |
| SRC | 90.0 | 4.6 | 100 | 100 |
| SRMS | 69.0 | 41 | 88 | 66 |
| SRPK1 | 66.0 | 0.05 | 88 | 100 |
| SRPK2 | 100.0 | 58 | 80 | 74 |
| SRPK3 | 93.0 | 2.5 | 100 | 100 |
| STK16 | 74.0 | 0.35 | 60 | 69 |
| STK33 | 18.0 | 4 | 15 | 13 |
| STK35 | 100.0 | 14 | 100 | 100 |
| STK36 | 97.0 | 85 | 100 | 100 |
| STK39 | 14.0 | 0 | 48 | 30 |
| SYK | 62.0 | 0.4 | 25 | 70 |
| TAK1 | 52.0 | 0.05 | 19 | 100 |
| TAOK1 | 73.0 | 6.5 | 98 | 85 |
| TAOK2 | 78.0 | 40 | 100 | 87 |
| TAOK3 | 81.0 | 8.6 | 97 | 81 |
| TBK1 | 85.0 | 4.8 | 85 | 84 |
| TEC | 100.0 | 24 | 100 | 86 |
| TESK1 | 100.0 | 65 | 98 | 100 |
| TGFBR1 | 5.1 | 91 | 100 | 100 |
| TGFBR2 | 82.0 | 100 | 84 | 96 |
| TIE1 | 96.0 | 19 | 99 | 100 |
| TIE2 | 92.0 | 46 | 100 | 100 |
| TLK1 | 95.0 | 78 | 88 | 72 |
| TLK2 | 95.0 | 42 | 100 | 93 |
| TNIK | 95.0 | 3.5 | 95 | 83 |
| TNK1 | 85.0 | 18 | 47 | 16 |
| TNK2 | 82.0 | 0.9 | 55 | 31 |
| TNNI3K | 99.0 | 93 | 100 | 100 |
| TRKA | 67.0 | 0.5 | 100 | 98 |
| TRKB | 61.0 | 7.5 | 100 | 100 |
| TRKC | 60.0 | 30 | 100 | 100 |
| TRPM6 | 88.0 | 93 | 98 | 98 |
| TSSK1B | 22.0 | 0.6 | 0 | 0 |
| TSSK3 | 74.0 | 72 | 66 | 100 |
| TTK | 12.0 | 0.25 | 0.85 | 1.4 |
| TXK | 100.0 | 40 | 100 | 100 |
| TYK2(JH1domain-catalytic) | 80.0 | 0 | 100 | 100 |
| TYK2(JH2domain-pseudokinase) | 66.0 | 7.2 | 100 | 100 |
| TYRO3 | 100.0 | 45 | 91 | 100 |
| ULK1 | 75.0 | 20 | 100 | 100 |
| ULK2 | 75.0 | 15 | 100 | 100 |
| ULK3 | 62.0 | 0.2 | 100 | 100 |
| VEGFR2 | 63.0 | 3.7 | 78 | 73 |
| VPS34 | 84.0 | 100 | 75 | 78 |
| VRK2 | 71.0 | 100 | 100 | 100 |
| WEE1 | 78.0 | 100 | 100 | 100 |
| WEE2 | 100.0 | 100 | 100 | 100 |
| WNK1 | 70.0 | 99 | 100 | 100 |
| WNK2 | 52.0 | 56 | 85 | 100 |
| WNK3 | 68.0 | 55 | 100 | 100 |
| WNK4 | 81.0 | 100 | 100 | 100 |
| YANK1 | 76.0 | 88 | 89 | 82 |
| YANK2 | 85.0 | 100 | 100 | 100 |
| YANK3 | 100.0 | 100 | 73 | 65 |
| YES | 100.0 | 10 | 100 | 100 |
| YSK1 | 97.0 | 28 | 83 | 81 |
| YSK4 | 12.0 | 0 | 22 | 94 |
| ZAK | 100.0 | 88 | 100 | 100 |
| ZAP70 | 35.0 | 2.2 | 81 | 100 |

As shown in able 7, the compounds of the present invention demonstrated smaller % control than 35% for such kinases as ABL1(E255K)-phosphorylated, ABL1(F317I)-nonphosphorylated, ABL1(F317I)-phosphorylated, ABL1(F317L)-nonphosphorylated, ABL1(F317L)-phosphorylated, ABL1(H396P)-nonphosphorylated, ABL1 (H396P)-phosphorylated, ABL1(M351T)-phosphorylated, ABL1(Q252H)-nonphosphorylated, ABL1(Q252H)-phosphorylated, ABL1(T315I)-nonphosphorylated, ABL1(T315I)-phosphorylated, ABL1(Y253F)-phosphorylated, ABL1-nonphosphorylated, ABL1-phosphorylated, ABL2, AKT3, ALK, ALK(C1156Y), ALK(L1196M), AMPK-alpha1, AMPK-alpha2, ANKK1, ARK5, ASK1, ASK2, AURKA, AURKB, AURKC, AXL, BIKE, BLK, BMPR1B, BMPR2, BTK, BUB1, CAMK1, CAMK1B, CAMK1D, CAMK1G, CAMK2A, CAMK4, CAMKK1, CAMKK2, CDK7, CHEK1, CHEK2, CLK1, CLK2, CLK3, CLK4, CSF1R, CSF1R-autoinhibited, CSNK1A1, CSNK1A1L, CSNK1D, CSNK1E, CSNK1G1, CSNK1G2, CSNK1G3, CSNK2A1, CSNK2A2, DAPK1, DAPK2, DAPK3, DCAMKL1, DDR2, DLK, DMPK, DMPK2, DRAK1, DRAK2, DYRK1A, DYRK1B, DYRK2, EGFR, EGFR(L858R,T790M), EGFR(T790M), EPHA3, EPHA7, EPHB6, ERK5, ERN1, FAK, FER, FES, FGFR2, FGFR3, FGFR3(G697C), FGFR4, FGR, FLT1, FLT3, FLT3(D835H), FLT3(D835V), FLT3(D835Y), FLT3(ITD), FLT3(ITD,D835V), FLT3(ITD,F691L), FLT3(K663Q), FLT3(N841I), FLT3(R834Q), FLT3-autoinhibited, FLT4, FYN, GAK, GRK4, GSK3A, HCK, HIPK1, HIPK2, HIPK3, HPK1, HUNK, IGF1R, IKK-alpha, IKK-beta, IKK-epsilon, INSR, INSRR, IRAK1, IRAK3, IRAK4, ITK, JAK1(JH1domain-catalytic), JAK1 (JH2domain-pseudokinase), JAK2(JH1domain-catalytic), JAK3(JH1domain-catalytic), JNK1, JNK2, JNK3, KIT, KIT(A829P), KIT(D816H), KIT(D816V), KIT(L576P), KIT(V559D), KIT(V559D,T670I), KIT(V559D,V654A), KIT-autoinhibited, LATS1, LATS2, LCK, LKB1, LRRK2, LRRK2(G2019S), LTK, LZK, MAP3K15, MAP3K2, MAP3K3, MAP4K2, MAP4K3, MAP4K4, MAP4K5, MAPKAPK2, MAPKAPK5, MARK2, MARK3, MEK1, MEK2, MEK3, MEK4, MEK5, MEK6, MELK, MERTK, MINK, MKK7, MKNK2, MLCK, MLK1, MLK2, MLK3, MST1, MST2, MST3, MST4, MYLK, MYO3A, MYO3B, NDR2, NEK10, NIK, OSR1, PAK3, PAK4, PAK6, PAK7, PDGFRA, PHKG1, PHKG2, PIK3CA(I800L), PIK3CD, PIK3CG, PIP5K1A, RIOK1, PIP5K1C, PIP5K2B, PIP5K2C, PKNB (*M. tuberculosis*), PLK1, PLK3, PLK4, PRKD1, PRKD2, PRKD3, PRP4, PYK2, RET, RET(M918T), RET(V804L), RET(V804M), RIOK2, RIOK3, RIPK1, RIPK4, RIPK5, ROCK1, ROCK2, ROS1, RPS6KA4(Kin.Dom.2-C-terminal), RPS6KA5 (Kin.Dom.2-C-terminal), RSK1(Kin.Dom.1-N-terminal), RSK2(Kin.Dom.1-N-terminal), RSK3(Kin.Dom.1-N-terminal), RSK3(Kin.Dom.2-C-terminal), RSK4(Kin.Dom.1-N-terminal), SBK1, SGK, SgK110, SIK2, SLK, SNARK, SNRK, SRC, SRPK1, SRPK3, STK16, STK33, STK35, STK39, SYK, TAK1, TAOK1, TAOK3, TBK1, TEC, TIE1, TGFBR1, TNIK, TNK1, TNK2, TRKA, TRKB, TRKC, TSSK1B, TTK, TYK2(JH1domain-catalytic), TYK2 (JH2domain-pseudokinase), ULK1, ULK2, ULK3, VEGFR2, YSK1, YSK4 or ZAP70. The result above indicates that the compounds of examples of the present invention have the activity of inhibiting the listed enzymes above, confirming the usability of the compounds of the invention for the disease relating to the enzymes listed above.

Therefore, the pyrrolo-pyrimidine derivative compounds of the present invention can be effectively used as a pharmaceutical composition for the treatment or prevention of ABL1(E255K)-phosphorylated, ABL1(F317I)-nonphosphorylated, ABL1(F317I)-phosphorylated, ABL1(F317L)-nonphosphorylated, ABL1(F317L)-phosphorylated, ABL1 (H396P)-nonphosphorylated, ABL1(H396P)-phosphorylated, ABL1(M351T)-phosphorylated, ABL1(Q252H)-nonphosphorylated, ABL1(Q252H)-phosphorylated, ABL1 (T315I)-nonphosphorylated, ABL1(T315I)-phosphorylated, ABL1(Y253F)-phosphorylated, ABL1-nonphosphorylated, ABL1-phosphorylated, ABL2, AKT3, ALK, ALK (C1156Y), ALK(L1196M), AMPK-alpha1, AMPK-alpha2, ANKK1, ARK5, ASK1, ASK2, AURKA, AURKB, AURKC, AXL, BIKE, BLK, BMPR1B, BMPR2, BTK, BUB1, CAMK1, CAMK1B, CAMK1D, CAMK1G, CAMK2A, CAMK4, CAMKK1, CAMKK2, CDK7, CHEK1, CHEK2, CLK1, CLK2, CLK3, CLK4, CSF1R, CSF1R-autoinhibited, CSNK1A1, CSNK1A1L, CSNK1D, CSNK1E, CSNK1G1, CSNK1G2, CSNK1G3, CSNK2A1, CSNK2A2, DAPK1, DAPK2, DAPK3, DCAMKL1, DDR2, DLK, DMPK, DMPK2, DRAK1, DRAK2, DYRK1A, DYRK1B, DYRK2, EGFR, EGFR(L858R,T790M), EGFR (T790M), EPHA3, EPHA7, EPHB6, ERK5, ERN1, FAK, FER, FES, FGFR2, FGFR3, FGFR3(G697C), FGFR4, FGR, FLT1, FLT3, FLT3(D835H), FLT3(D835V), FLT3 (D835Y), FLT3(ITD), FLT3(ITD,D835V), FLT3(ITD, F691L), FLT3(K663Q), FLT3(N841I), FLT3(R834Q), FLT3-autoinhibited, FLT4, FYN, GAK, GRK4, GSK3A, HCK, HIPK1, HIPK2, HIPK3, HPK1, HUNK, IGF1R, IKK-alpha, IKK-beta, IKK-epsilon, INSR, INSRR, IRAK1, IRAK3, IRAK4, ITK, JAK1(JH1domain-catalytic), JAK1 (JH2domain-pseudokinase), JAK2(JH1domain-catalytic), JAK3(JH1domain-catalytic), JNK1, JNK2, JNK3, KIT, KIT (A829P), KIT(D816H), KIT(D816V), KIT(L576P), KIT (V559D), KIT(V559D,T670I), KIT(V559D,V654A), KIT-autoinhibited, LATS1, LATS2, LCK, LKB1, LRRK2, LRRK2(G2019S), LTK, LZK, MAP3K15, MAP3K2, MAP3K3, MAP4K2, MAP4K3, MAP4K4, MAP4K5, MAPKAPK2, MAPKAPK5, MARK2, MARK3, MEK1, MEK2, MEK3, MEK4, MEK5, MEK6, MELK, MERTK, MINK, MKK7, MKNK2, MLCK, MLK1, MLK2, MLK3, MST1, MST2, MST3, MST4, MYLK, MYO3A, MYO3B, NDR2, NEK10, NIK, OSR1, PAK3, PAK4, PAK6, PAK7, PDGFRA, PHKG1, PHKG2, PIK3CA(I800L), PIK3CD, PIK3CG, PIP5K1A, RIOK1, PIP5K1C, PIP5K2B, PIP5K2C, PKNB(*M. tuberculosis*), PLK1, PLK3, PLK4, PRKD1, PRKD2, PRKD3, PRP4, PYK2, RET, RET (M918T), RET(V804L), RET(V804M), RIOK2, RIOK3, RIPK1, RIPK4, RIPK5, ROCK1, ROCK2, ROS1, RPS6KA4(Kin.Dom.2-C-terminal), RPS6KA5 (Kin.Dom.2-C-terminal), RSK1(Kin.Dom.1-N-terminal), RSK2 (Kin.Dom.1-N-terminal), RSK3(Kin.Dom.1-N-terminal), RSK3(Kin.Dom.2-C-terminal), RSK4(Kin.Dom.1-N-terminal), SBK1, SGK, SgK110, SIK2, SLK, SNARK, SNRK, SRC, SRPK1, SRPK3, STK16, STK33, STK35, STK39, SYK, TAK1, TAOK1, TAOK3, TBK1, TEC, TIE1, TGFBR1, TNIK, TNK1, TNK2, TRKA, TRKB, TRKC, TSSK1B, TTK, TYK2(JH1domain-catalytic), TYK2 (JH2domain-pseudokinase), ULK1, ULK2, ULK3, VEGFR2, YSK1, YSK4 or ZAP70 related disease.

INDUSTRIAL APPLICABILITY

The compound represented by formula 1, the optical isomer thereof or the pharmaceutically acceptable salt thereof according to the present invention has an excellent activity of inhibiting various protein kinases including LRRK2, so that a pharmaceutical composition comprising the same as an active ingredient can be effectively used for the prevention or treatment of protein kinase related disease.

What is claimed is:
1. A compound represented by formula 1 below, an optical isomer thereof, or a pharmaceutically acceptable salt thereof:

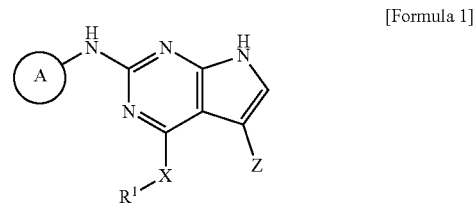

[Formula 1]

wherein,

X is —NH—;

Z is cyano (—CN); or straight or branched C1-C3 alkyl substituted with one or more halogens;

$R^1$ is straight or branched unsubstituted C1-C6 alkyl; C3-C6 cycloalkyl nonsubstituted or substituted with one or more straight or branched C1-C3 alkyls; or unsubstituted 3-8 membered heterocycloalkyl containing one or more heteroatoms selected from the group consisting of N and O; and

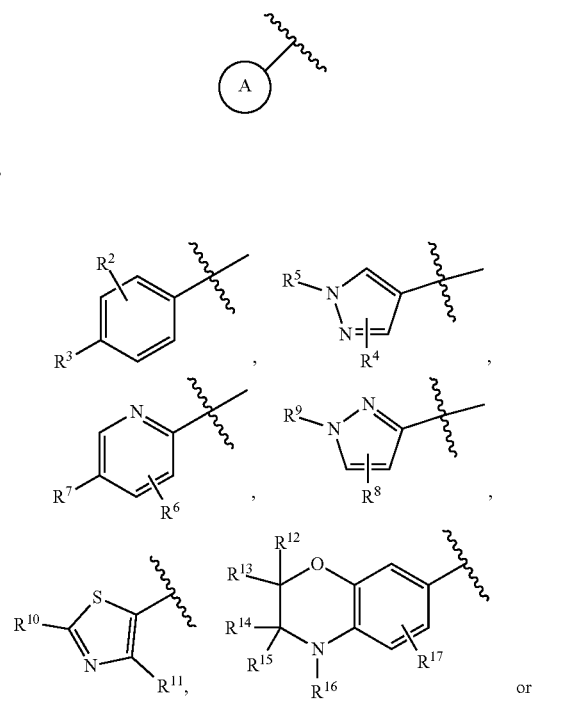

is

-continued

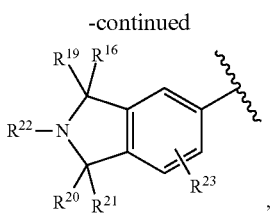

wherein, R² is one or more substituents selected from the group consisting of halogen and straight or branched C1-C3 alkoxy, R⁴, R⁶, R⁸, R¹¹, R¹⁷, and R²³ are independently one or more substituents selected from the group consisting of hydrogen, halogen, straight or branched C1-C3 alkyl and straight or branched C1-C3 alkoxy, R³ is methoxy,

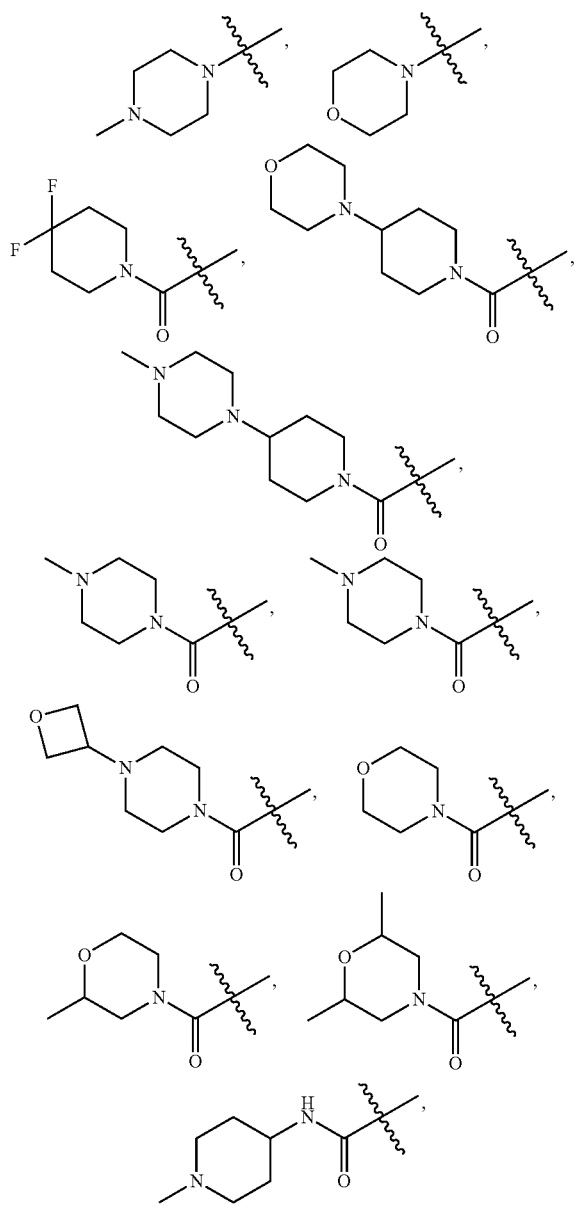

-continued

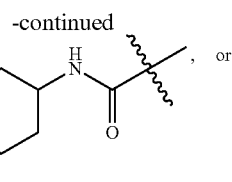

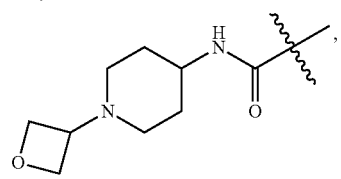

R⁵, R⁷ and R⁹ are independently straight or branched C1-C3 alkyl; straight or branched C1-C3 alkoxy; straight or branched C1-C3 alkyl substituted with one or more substituents selected from the group consisting of hydroxy, straight or branched C1-C3 alkyl, straight or branched C1-C3 alkoxy, aminocarboxy group (—(C═O)NH₂) and —CN; 3-8 membered heterocycloalkyl containing one or more heteroatoms selected from the group consisting of N and O nonsubstituted or substituted with one or more substituents selected from the group consisting of halogen and 3-5 membered heterocycloalkyl containing one or more oxygen atoms; 3-8 membered heterocycloalkyl containing one or more heteroatoms selected from the group consisting of N and O nonsubstituted or substituted with one or more straight or branched C1-C3 alkyls; or —(C═O)NR²⁴R²⁵, wherein, R²⁴ and R²⁵ are independently hydrogen; 3-8 membered heterocycloalkyl containing one or more heteroatoms selected from the group consisting of N and O substituted with straight or branched C1-C3 alkyl or 3-5 membered heterocycloalkyl containing one or more oxygen atoms; or R²⁴ and R²⁵ form 3-8 membered heterocycloalkyl containing one or more heteroatoms selected from the group consisting of N and O along with nitrogen atom to which they are attached, wherein, the substituted heterocycloalkyl is substituted with one or more substituents selected from the group consisting of halogen; straight or branched C1-C3 alkyl; and 3-6 membered heterocycloalkyl containing one or more heteroatoms selected from the group consisting of N and O nonsubstituted or substituted with one or more straight or branched C1-C3 alkyls, R¹⁰ is —CR²⁶R²⁷—CN, wherein R²⁶ and R²⁷ are independently hydrogen, or straight or branched C1-3 alkyl, R¹², R¹³, R¹⁴, R¹⁵, R¹⁸, R¹⁹, R²⁰, and R²¹ are independently hydrogen, or straight or branched C1-3 alkyl, or two of R¹², R¹³, R¹⁴, R¹⁵, R¹⁸, R¹⁹, R²⁰, and R²¹ bonded to the same carbon can form carbonyl along with the carbon to which they are attached, and R¹⁶ and R²² are independently hydrogen, or straight or branched C1-3 alkyl, and wherein when Z is CF₃, R₃ is not OCH₃.

2. The compound, the optical isomer thereof, or the pharmaceutically acceptable salt thereof according to claim 1, wherein:
X is —NH—;
Z is —CN or methyl substituted with one or more halogens;

R¹ is straight or branched unsubstituted C1-C3 alkyl; C3-C5 cycloalkyl nonsubstituted or substituted with one or more methyls; or unsubstituted 5-6 membered heterocycloalkyl containing one or more heteroatoms selected from the group consisting of N and O; and

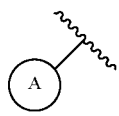

is

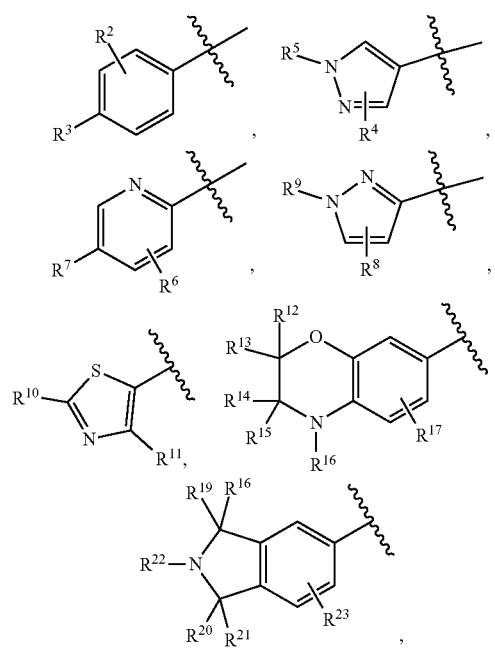

wherein, R² is one or more substituents selected from the group consisting of fluoro, chloro, bromo, methoxy and ethoxy, R⁴, R⁶, R⁸, R¹¹, R¹⁷, and R²³ are independently one or more substituents selected from the group consisting of hydrogen, fluoro, chloro, bromo, methyl, ethyl, methoxy and ethoxy, R⁵, R⁷ and R⁹ are independently methyl; isopropyl; methoxy; straight or branched C1-C3 alkyl substituted with one or more substituents selected from the group consisting of hydroxy, methoxy, methyl, aminocarboxy group (—(C=O)NH₂) and —CN; piperidinyl substituted with one or more substituents selected from the group consisting of fluoro, chloro and oxetanyl; piperazinyl or morpholinyl nonsubstituted or substituted with one or more methyls; or —(C=O)NR²⁴R²⁵, wherein, R²⁴ and R²⁵ are independently hydrogen; piperidinyl substituted with methyl, isopropyl or oxetanyl; or R²⁴ and R²⁵ form nonsubstituted or substituted piperazinyl, morpholinyl or piperidinyl along with nitrogen atom to which they are attached, wherein, the substituted piperazinyl, morpholinyl or piperidinyl can be substituted with one or more substituents selected from the group consisting of fluoro, methyl, oxetanyl, piperazinyl and morpholinyl, R¹⁰ is —CR²⁶R²⁷—CN, wherein R²⁶ and R²⁷ are independently hydrogen, methyl or ethyl, R¹², R¹³, R¹⁴, R¹⁵, R¹⁸, R¹⁹, R²⁰, and R²¹ are independently hydrogen, methyl or ethyl, or two of R¹², R¹³, R¹⁴, R¹⁵, R¹⁸, R¹⁹, R²⁰, and R²¹ bonded to the same carbon can form carbonyl along with the carbon to which they are attached, and R¹⁶ and R²² are independently hydrogen, methyl or ethyl.

3. The compound, the optical isomer thereof, or the pharmaceutically acceptable salt thereof according to claim 1, wherein:

X is —NH—;

Z is —CN or —CF₃;

R¹ is methyl, ethyl, n-propyl, isopropyl, cyclopropyl, 1-methylcyclopropyl, tetrahydropyranyl or tetrahydrofuranyl;

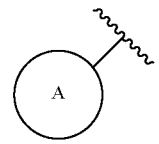

is

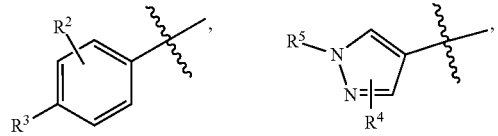

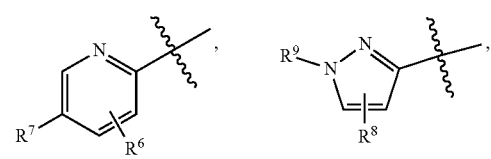

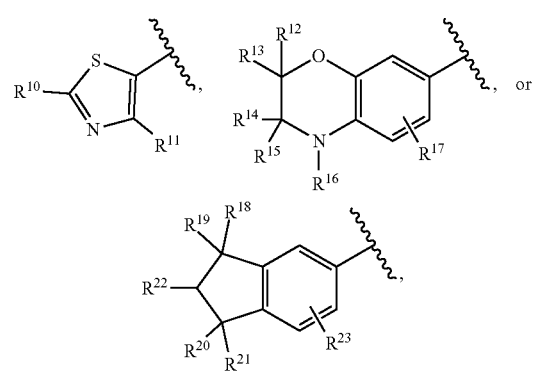

wherein, R² is one or more substituents selected from the group consisting of chloro, fluoro, bromo, and methoxy, R⁴, R⁶, R⁸, R¹¹, R¹⁷, and R²³ are independently one or more substituents selected from the group consisting of hydrogen, chloro, fluoro, bromo, methyl and methoxy;

$R^7$ is methoxy,

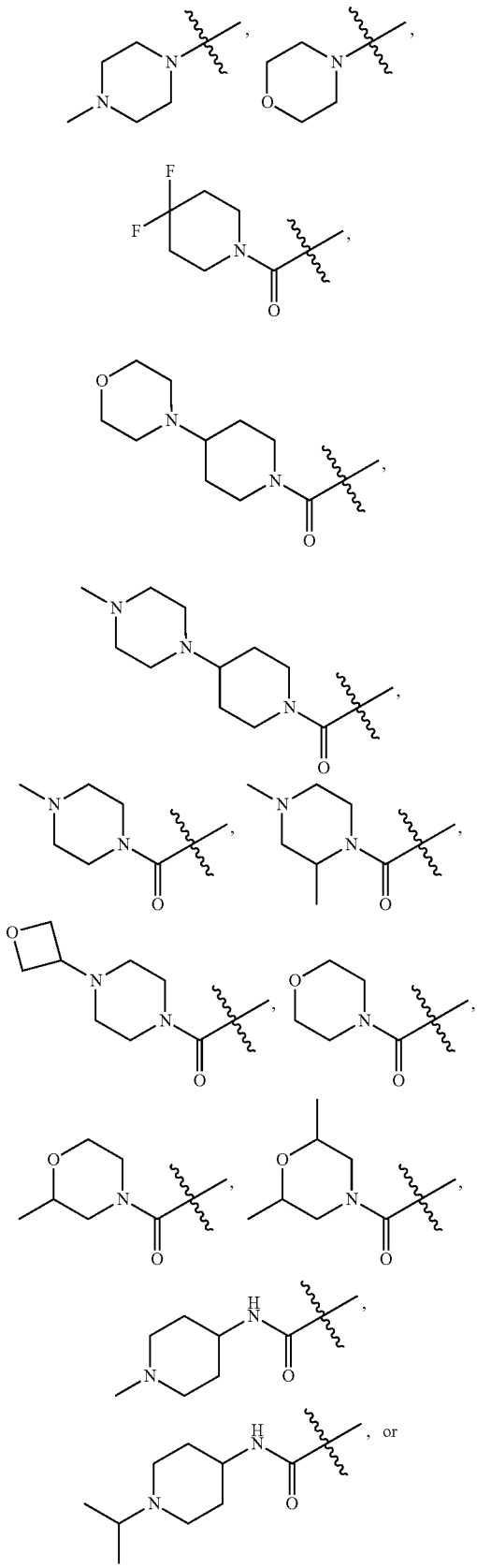

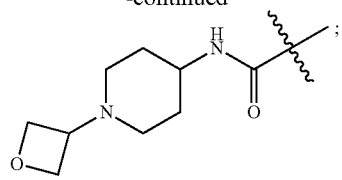

and $R^5$ and $R^9$ are independently methyl, isopropyl,

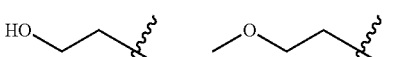

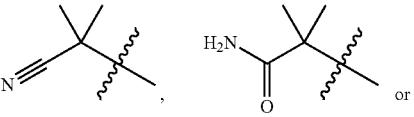

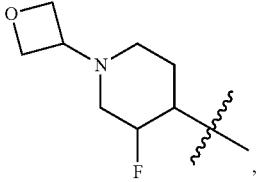

$R^{10}$ is —$CR^{26}R^{27}$—CN, wherein $R^{26}$ and $R^{27}$ are independently hydrogen or methyl, $R^{12}$, $R^{13}$, $R^{14}$, $R^{15}$, $R^{18}$, $R^{19}$, $R^{20}$, and $R^{21}$ are independently hydrogen or methyl, or two of $R^{12}$, $R^{13}$, $R^{14}$, $R^{15}$, $R^{18}$, $R^{19}$, $R^{20}$, and $R^{21}$ bonded to the same carbon can form carbonyl along with the carbon to which they are attached, and $R^{16}$ and $R^{22}$ are independently hydrogen or methyl.

4. The compound, the optical isomer thereof, or the pharmaceutically acceptable salt thereof according to claim 1, wherein:

X is —NH—;

Z is —CN or —$CF_3$;

$R^1$ is methyl, ethyl, n-propyl, isopropyl, cyclopropyl, 1-methylcyclopropyl, tetrahydropyran-4-yl or tetrahydrofuran-3-yl; and

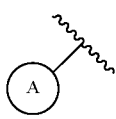

is

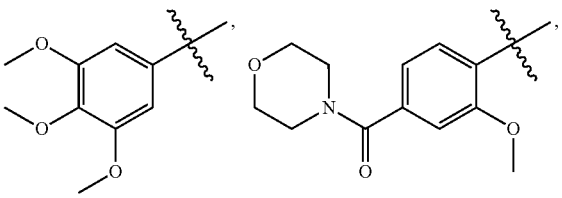

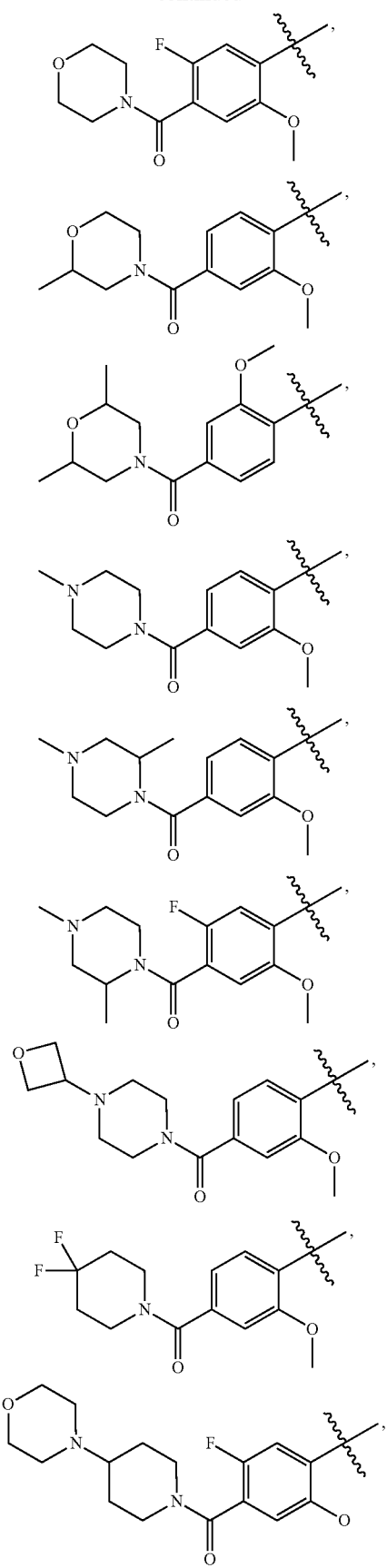
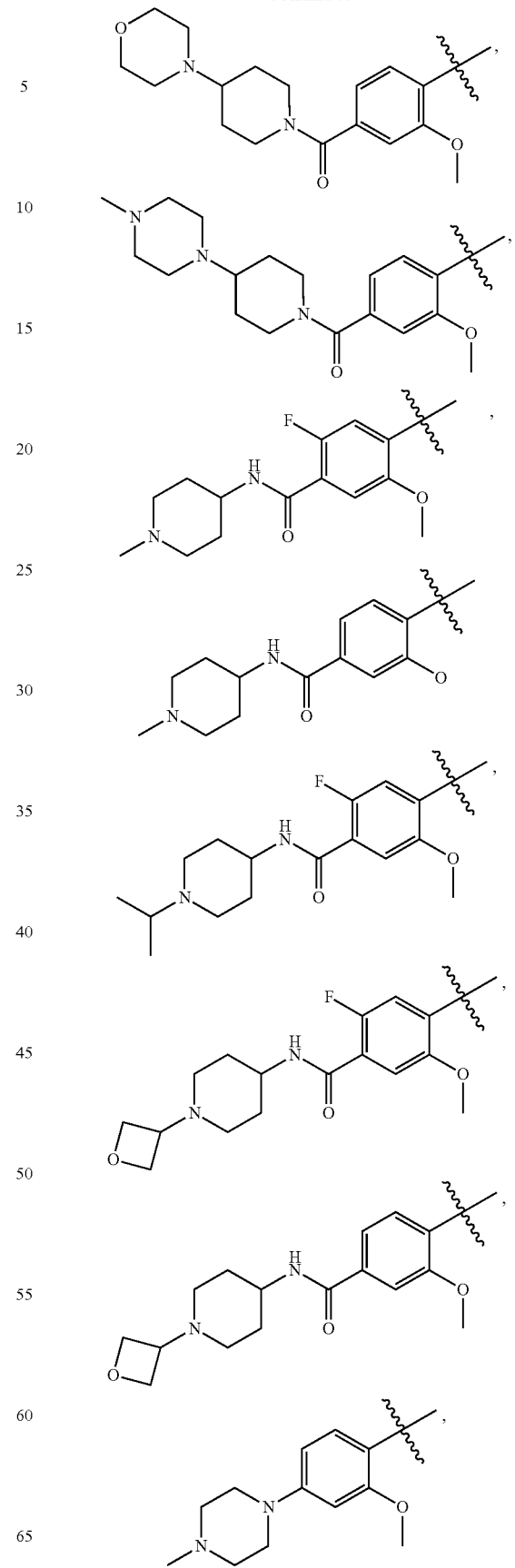

131

-continued

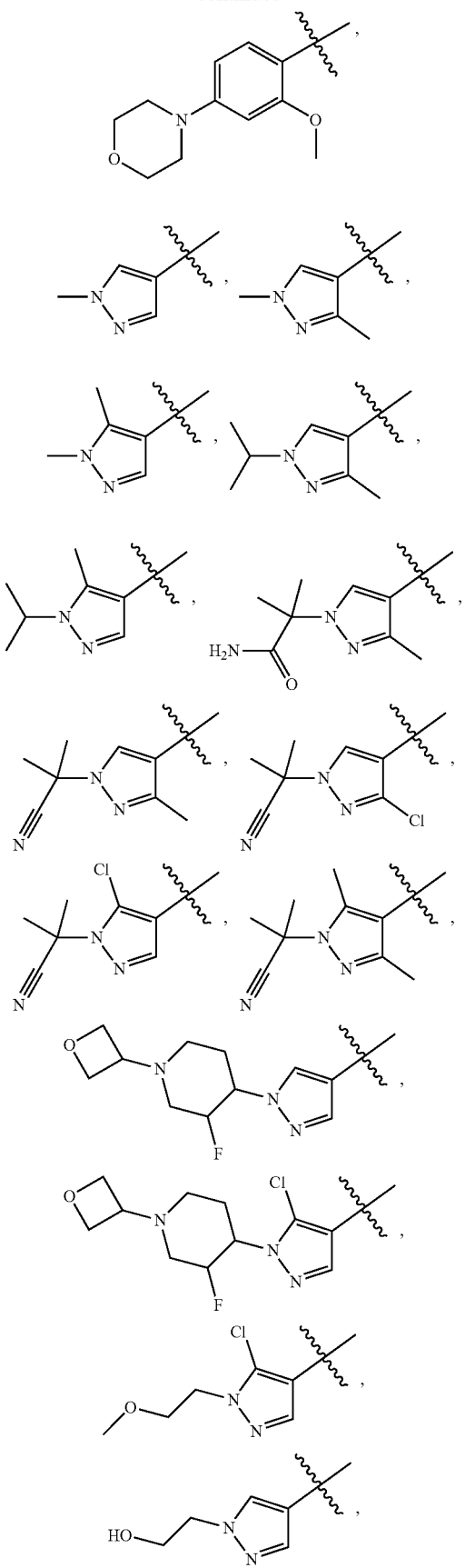

132

-continued

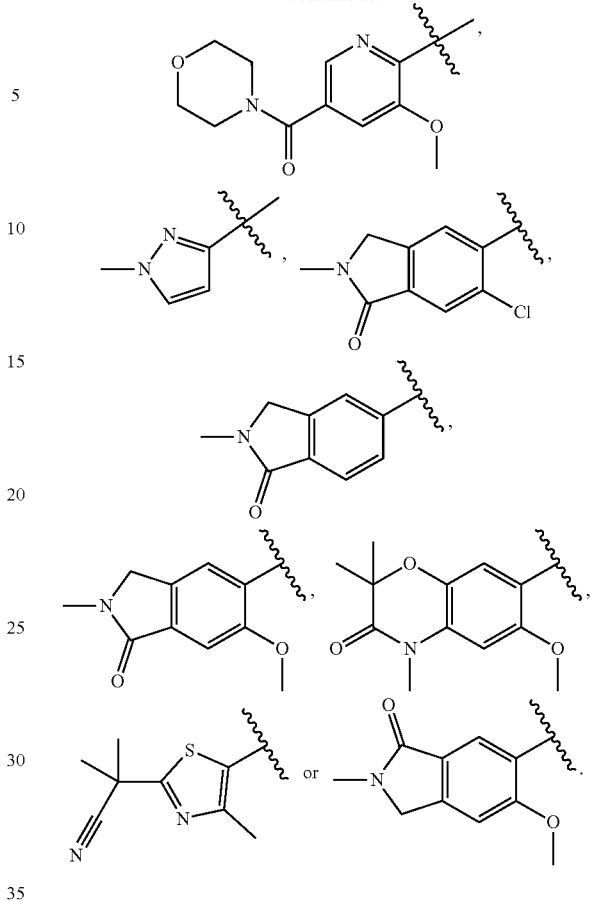

5. The compound, the optical isomer thereof, or the pharmaceutically acceptable salt thereof according to claim 1, wherein the compound represented by formula 1 is selected from the group consisting of the following compounds:

(1) 2-((2-methoxy-4-(morpholine-4-carbonyl)phenyl)amino)-4-(methylamino)-7H-pyrrolo[2,3-d]pyrimidine-5-carbonitrile;

(2) 4-(ethylamino)-2-((2-methoxy-4-(morpholine-4-carbonyl)phenyl)amino)-7H-pyrrolo[2,3-d]pyrimidine-5-carbonitrile;

(3) 4-(ethylamino)-2-((3,4,5-trimethoxyphenyl)amino)-7H-pyrrolo[2,3-d]pyrimidine-5-carbonitrile;

(4) 4-(ethylamino)-2-((1-methyl-1H-pyrazole-4-yl)amino)-7H-pyrrolo[2,3-d]pyrimidine-5-carbonitrile;

(5) 4-(ethylamino)-2-((1-methyl-1H-pyrazole-3-yl)amino)-7H-pyrrolo[2,3-d]pyrimidine-5-carbonitrile;

(6) 4-(ethylamino)-2-((5-fluoro-2-methoxy-4-(morpholine-4-carbonyl)phenyl)amino)-7H-pyrrolo[2,3-d]pyrimidine-5-carbonitrile;

(7) 4-(ethylamino)-2-((5-fluoro-2-methoxy-4-(4-morpholinopiperidine-1-carbonyl)phenyl)amino)-7H-pyrrolo[2,3-d]pyrimidine-5-carbonitrile;

(8) 4-(ethylamino)-2-((2-methoxy-4-(4-morpholinopiperidine-1-carbonyl)phenyl)amino)-7H-pyrrolo[2,3-d]pyrimidine-5-carbonitrile;

(9) 2-((2-methoxy-4-(4-morpholinylpiperidine-1-carbonyl)phenyl)amino)-4-(methylamino)-7H-pyrrolo[2,3-d]pyrimidine-5-carbonitrile;

(10) 2-((5-fluoro-2-methoxy-4-(morpholine-4-carbonyl)phenyl)amino)-4-(methylamino)-7H-pyrrolo[2,3-d]pyrimidine-5-carbonitrile;

(11) 2-((5-fluoro-2-methoxy-4-(4-morpholinopiperidine-1-carbonyl)phenyl)amino)-4-(methyl amino)-7H-pyrrolo[2,3-d]pyrimidine-5-carbonitrile;
(12) 2-((2-methoxy-4-(morpholine-4-carbonyl)phenyl) amino)-4-(propylamino)-7H-pyrrolo[2,3-d]pyrimidine-5-carbonitrile;
(13) 2-((2-methoxy-4-(4-morpholinopiperidine-1-carbonyl)phenyl)amino)-4-(propylamino)-7H-pyrrolo[2,3-d]pyrimidine-5-carbonitrile;
(14) 2-((5-fluoro-2-methoxy-4-(morpholine-4-carbonyl) phenyl)amino)-4-(propylamino)-7H-pyrrolo[2,3-d]pyrimidine-5-carbonitrile;
(15) 2-((5-fluoro-2-methoxy-4-(4-morpholinopiperidine-1-carbonyl) phenyl)amino)-4-(propylamino)-7H-pyrrolo[2,3-d]pyrimidine-5-carbonitrile;
(16) 4-(cyclopropylamino)-2-((2-methoxy-4-(morpholine-4-carbonyl)phenyl)amino)-7H-pyrrolo[2,3-d]pyrimidine-5-carbonitrile;
(17) 4-(cyclopropylamino)-2-((2-methoxy-4-(4-morpholinopiperidine-1-carbonyl)phenyl)amino)-7H-pyrrolo[2,3-d]pyrimidine-5-carbonitrile;
(18) 4-(cyclopropylamino)-2-((5-fluoro-2-methoxy-4-(morpholine-4-carbonyl)phenyl)amino)-7H-pyrrolo[2,3-d]pyrimidine-5-carbonitrile;
(19) 4-(cyclopropylamino)-2-((5-fluoro-2-methoxy-4-(4-morpholinopiperidine-1-carbonyl)phenyl)amino)-7H-pyrrolo[2,3-d]pyrimidine-5-carbonitrile;
(20) (R)-2-((2-methoxy-4-(2-methylmorpholine-4-carbonyl)phenyl)amino)-4-(methylamino)-7H-pyrrolo[2,3-d]pyrimidine-5-carbonitrile;
(21) (S)-2-((2-methoxy-4-(2-methylmorpholine-4-carbonyl)phenyl)amino)-4-(methylamino)-7H-pyrrolo[2,3-d]pyrimidine-5-carbonitrile;
(22) 2-((4-((2R,6S)-2,6-dimethylmorpholine-4-carbonyl)-2-methoxyphenyl)amino)-4-(methylamino)-7H-pyrrolo[2,3-d]pyrimidine-5-carbonitrile;
(23) 2-((4-(4,4-difluoropiperidine-1-carbonyl)-2-methoxyphenyl amino)-4-(methylamino)-7H-pyrrolo[2,3-d]pyrimidine-5-carbonitrile;
(24) 2-((4-((2R,6S)-2,6-dimethylmorpholine-4-carbonyl)-2-methoxyphenyl)amino)-4-(ethylamino)-7H-pyrrolo[2,3-d]pyrimidine-5-carbonitrile;
(25) (R)-4-(ethylamino)-2-((2-methoxy-4-(2-methylmorpholine-4-carbonyl)phenyl)amino)-7H-pyrrolo[2,3-d] pyrimidine-5-carbonitrile;
(26) (S)-4-(ethylamino)-2-((2-methoxy-4-(2-methylmorpholine-4-carbonyl)phenyl)amino)-7H-pyrrolo[2,3-d] pyrimidine-5-carbonitrile;
(27) 2-((4-(4,4-difluoropiperidine-1-carbonyl)-2-methoxyphenyl)amino)-4-(ethylamino)-7H-pyrrolo[2,3-d]pyrimidine-5-carbonitrile;
(28) 6-((1,3-dimethyl-1H-pyrazole-4-yl)amino)-4-(methylamino)-1H-pyrrolo[2,3-b]pyrimidine-3-carbonitrile;
(29) 6-((1,5-dimethyl-1H-pyrazole-4-yl)amino)-4-(methyl amino)-1H-pyrrolo[2,3-b]pyrimidine-3-carbonitrile;
(30) 6-((1-isopropyl-3-methyl-1H-pyrazole-4-yl)amino)-4-(methylamino)-1H-pyrrolo[2,3-b]pyrimidine-3-carbonitrile;
(31) 6-((1-isopropyl-5-methyl-1H-pyrazole-4-yl)amino)-4-(methylamino)-1H-pyrrolo[2,3-b]pyrimidine-3-carbonitrile;
(32) 2-((1,3-dimethyl-1H-pyrazole-4-yl)amino)-4-(ethylamino)-7H-pyrrolo[2,3-d]pyrimidine-5-carbonitrile;
(33) 2-((1,5-dimethyl-1H-pyrazole-4-yl)amino)-4-(ethylamino)-7H-pyrrolo[2,3-d]pyrimidine-5-carbonitrile;
(34) 4-(ethylamino)-2-((1-isopropyl-3-methyl-1H-pyrazole-4-yl)amino)-7H-pyrrolo[2,3-d]pyrimidine-5-carbonitrile;
(35) 4-(ethylamino)-2-((1-isopropyl-5-methyl-1H-pyrazole-4-yl)amino)-7H-pyrrolo[2,3-d]pyrimidine-5-carbonitrile;
(36) 2-((2-methoxy-4-(morpholine-4-carbonyl)phenyl) amino)-4-((1-methylcyclopropyl)amino)-7H-pyrrolo [2,3-d]pyrimidine-5-carbonitrile;
(37) 2-((5-fluoro-2-methoxy-4-(morpholine-4-carbonyl) phenyl)amino)-4-((1-methylcyclopropyl)amino)-7H-pyrrolo[2,3-d]pyrimidine-5-carbonitrile;
(38) 2(1-isopropyl-5-methyl-1H-pyrazole-4-yl)amino)-4-((1-methylcyclopropyl)amino)-7H-pyrrolo[2,3-d]pyrimidine-5-carbonitrile;
(39) 2(1-isopropyl-3-methyl-1H-pyrazole-4-yl)amino)-4-((1-methylcyclopropyl)amino)-7H-pyrrolo[2,3-d]pyrimidine-5-carbonitrile;
(40) 2-((1,3-dimethyl-1H-pyrazole-4-yl)amino)-4-((1-methylcyclopropyl)amino)-7H-pyrrolo[2,3-d]pyrimidine-5-carbonitrile;
(41) 2-((1,5-dimethyl-1H-pyrazole-4-yl)amino)-4-((1-methylcyclopropyl)amino)-7H-pyrrolo[2,3-d]pyrimidine-5-carbonitrile;
(42) (R)-2-((2-methoxy-4-(2-methylmorpholine-4-carbonyl)phenyl)amino)-4-((1-methylcyclopropyl)amino)-7H-pyrrolo[2,3-d]pyrimidine-5-carbonitrile;
(43) (S)-2-((2-methoxy-4-(2-methylmorpholine-4-carbonyl)phenyl)amino)-4-((1-methylcyclopropyl)amino)-7H-pyrrolo[2,3-d]pyrimidine-5-carbonitrile;
(44) 2-((4-((2R,6S)-2,6-dimethylmorpholine-4-carbonyl)-2-methoxyphenyl)amino)-4-((1-methylcyclopropyl)amino)-7H-pyrrolo[2,3-d]pyrimidine-5-carbonitrile;
(45) 2-((4-(4,4-difluoropiperidine-1-carbonyl)-2-methoxyphenyl)amino)-4-((1-methylcyclopropyl) amino)-7H-pyrrolo[2,3-d]pyrimidine-5-carbonitrile;
(46) 2-(4-((5-cyano-4-(methylamino)-7H-pyrrolo[2,3-d] pyrimidine-2-yl)amino)-3-methyl-1H-pyrazole-1-yl)-2-methylpropaneamide;
(47) 2-((1-(2-cyanopropane-2-yl)-3-methyl-1H-pyrazole-4-yl)amino)-4-(methylamino)-7H-pyrrolo[2,3-d]pyrimidine-5-carbonitrile;
(48) 4-(ethylamino)-2-((3-methoxy-5-(morpholine-4-carbonyl)pyridine-2-yl)amino)-7H-pyrrolo[2,3-d]pyrimidine-5-carbonitrile;
(49) 2-((1-(2-cyanopropane-2-yl)-3-methyl-1H-pyrazole-4-yl)amino)-4-((1-methylcyclopropyl)amino)-7H-pyrrolo[2,3-d]pyrimidine-5-carbonitrile;
(50) 2-((5-chloro-1-((3S,4S)-3-fluoro-1-(oxetane-3-yl)piperidine-4-yl)-1H-pyrazole-4-yl)amino)-4-(methylamino)-7H-pyrrolo[2,3-d]pyrimidine-5-carbonitrile;
(51) 2-((5-chloro-1-((3S, 4S)-3-fluoro-1-(oxetane-3-yl) piperidine-4-yl)-1H-pyrazole-4-yl)amino)-4-(ethylamino)-7H-pyrrolo[2,3-d]pyrimidine-5-carbonitrile;
(52) 2-((5-chloro-1-((3S,4S)-3-fluoro-1-(oxetane-3-yl)piperidine-4-yl)-1H-pyrazole-4-yl)amino)((1-methylcyclopropyl)amino)-7H-pyrrolo[2,3-d]pyrimidine-5-carbonitrile;
(53) 4-(ethylamino)-2-((1-(3S, 4S)-3-fluoro-1-(oxetane-3-yl)piperidine-4-yl)-1H-pyrazole-4-yl)amino)-7H-pyrrolo[2,3-d]pyrimidine-5-carbonitrile;
(54) 2-((1-((3S,4S)-3-fluoro-1-(oxetane-3-yl)piperidine-4-yl)-1H-pyrazole-4-yl)amino)-4-((methylcyclopropyl)amino)-7H-pyrrolo[2,3-d]pyrimidine-5-carbonitrile;

(55) 4-((5-cyano-4-(methylamino)-7H-pyrrolo[2,3-d]pyrimidine-2-yl)amino)-3-methoxy-N-(1-methylpiperidine-4-yl)benzamide;
(56) 4-((5-cyano-4-(ethylamino)-7H-pyrrolo[2,3-d]pyrimidine-2-yl)amino)-3-methoxy-N-(1-methylpiperidine-4-yl)benzamide;
(57) 2-((2-methoxy-4-(oxetane-3-yl)piperazine-1-carbonyl)phenyl)amino)-4-(methylamino)-7H-pyrrolo[2,3-d]pyrimidine-5-carbonitrile;
(58) 4-(ethylamino)-2-((2-methoxy-4-(4-(oxetane-3-yl)piperazine-1-carbonyl)phenyl)amino)-7H-pyrrolo[2,3-d]pyrimidine-5-carbonitrile;
(59) 2-((5-chloro-1-(2-methoxyethyl)-1H-pyrazole-4-yl)amino)-4-(methylamino)-7H-pyrrolo[2,3-d]pyrimidine-5-carbonitrile;
(60) 4-((5-cyano-4-(ethylamino)-7H-pyrrolo[2,3-d]pyrimidine-2-yl)amino)-3-methoxy-N-(1-(oxetane-3-yl)piperidine-4-yl)benzylamide;
(61) 4-((5-cyano-4-(methylamino)-7H-pyrrolo[2,3-d]pyrimidine-2-yl)amino)-3-methoxy-N-(1-(oxetane-3-yl)piperidine-4-yl)benzylamide;
(62) 2-((5-chloro-1-(2-methoxyethyl)-1H-pyrazole-4-yl)amino)-4-(ethylamino)-7H-pyrrolo[2,3-d]pyrimidine-5-carbonitrile;
(63) 4(5-cyano-4-(methylamino)-7H-pyrrolo[2,3-d]pyrimidine-2-yl)amino)-2-fluoro-5-methoxy-N-(1-(oxetane-3-pyrrolidine-1-yl)piperidine-4-yl)benzamide;
(64) 4-((5-cyano-4-(ethylamino)-7H-pyrrolo[2,3-d]pyrimidine-2-yl)amino)-2-fluoro-5-methoxy-N-(1-(oxetane-3-pyrrolidine-1-yl)piperidine-4-yl)benzamide;
(65) 4(5-cyano-4-(methylamino)-7H-pyrrolo[2,3-d]pyrimidine-2-yl)amino)-2-fluoro-5-methoxy-N-(1-methylpiperidine-4-yl)benzamide;
(66) 4(5-cyano-4-(ethylamino)-7H-pyrrolo[2,3-d]pyrimidine-2-yl)amino)-2-fluoro-5-methoxy-N-(1-methylpiperidine-4-yl)benzamide;
(67) 4-((5-cyano-4-(methylamino)-7H-pyrrolo[2,3-d]pyrimidine-2-yl)amino)-2-fluoro-N-(1-isopropylpiperidine-4-yl)-5-methoxybenzamide;
(68) 4(5-cyano-4-(ethylamino)-7H-pyrrolo[2,3-d]pyrimidine-2-yl)amino)-2-fluoro-N-(1-isopropylpiperidine-4-yl)-5-methoxybenzamide;
(69) 2-((1-(2-hydroxyethyl)-1H-pyrazole-4-yl)amino)-4-(methylamino)-7H-pyrrolo[2,3-d]pyrimidine-5-carbonitrile;
(70) 4-(ethylamino)-2-((1-(2-hydroxyethyl)-1H-pyrazole-4-yl)amino)-7H-pyrrolo[2,3-d]pyrimidine-5-carbonitrile;
(71) 2-((3-chloro-1-(2-cyanopropane-2-yl)-1H-pyrazole-4-yl)amino)-4-(methylamino)-7H-pyrrolo[2,3-d]pyrimidine-5-carbonitrile;
(72) 2-((3-chloro-1-(2-cyanopropane-2-yl)-1H-pyrazole-4-yl)amino)-4-(ethylamino)-7H-pyrrolo[2,3-d]pyrimidine-5-carbonitrile;
(73) 2-((5-chloro-1-(2-cyanopropane-2-yl)-1H-pyrazole-4-yl)amino)-4-(methylamino)-7H-pyrrolo[2,3-d]pyrimidine-5-carbonitrile;
(74) 2-((5-chloro-1-(2-cyanopropane-2-yl)-1H-pyrazole-4-yl)amino)-4-(ethylamino)-7H-pyrrolo[2,3-d]pyrimidine-5-carbonitrile;
(75) (R)-2-((4-(2,4-dimethylpiperazine-1-carbonyl)-2-methoxyphenyl)amino)-4-(methylamino)-7H-pyrrolo[2,3-d]pyrimidine-5-carbonitrile;
(76) (R)-2-((4-(2,4-dimethylpiperazine-1-carbonyl)-2-methoxyphenyl)amino)-4-(ethylamino)-7H-pyrrolo[2,3-d]pyrimidine-5-carbonitrile;
(77) 2-((1-(2-cyanopropane-2-yl)-3,5-dimethyl-1H-pyrazole-4-yl)amino)-4-(methylamino)-7H-pyrrolo[2,3-d]pyrimidine-5-carbonitrile;
(78) 2-((1-(2-cyanopropane-2-yl)-3,5-dimethyl-1H-pyrazole-4-yl)amino)-4-(ethylamino)-7H-pyrrolo[2,3-d]pyrimidine-5-carbonitrile;
(79) (R)-2-((4-(2,4-dimethylpiperazine-1-carbonyl)-5-fluoro-2-methoxyphenyl)amino)-4-(ethylamino)-7H-pyrrolo[2,3-d]pyrimidine-5-carbonitrile;
(80) (R)-2-((4-(2,4-dimethylpiperazine-1-carbonyl)-5-fluoro-2-methoxyphenyl)amino)-4-(methylamino)-7H-pyrrolo[2,3-d]pyrimidine-5-carbonitrile;
(81) 4-((5-cyano-4-((1-methylcyclopropyl)amino)-7H-pyrrolo[2,3-]pyrimidine-2-yl)amino)-2-fluoro-5-methoxy-N-(1-(oxetane-3-yl)piperidine-4-yl)benzamide;
(82) 4-((5-cyano-4-((1-methylcyclopropyl)amino)-7H-pyrrolo[2,3-d]pyrimidine-2-yl)amino)-2-fluoro-N-(1-isopropylpiperidine-4-yl)-5-methoxybenzamide;
(83) 4-((5-cyano-4-((1-methylcyclopropyl)amino)-7H-pyrrolo[2,3-d]pyrimidine-2-yl)amino)-2-fluoro-5-methoxy-N-(1-methylpiperidine-4-yl)benzamide;
(102) N2-(5-chloro-1-((3S,4S)-3-fluoro-1-(oxetane-3-yl)piperidine-4-yl)-1H-pyrazole-4-yl)-N4-ethyl-5-(trifluoromethyl)-7H-pyrrolo[2,3-d]pyrimidine-2,4-diamine;
(103) 2-(4-((4-(ethylamino)-5-(trifluoromethyl)-7H-pyrrolo[2,3-d]pyrimidine-2-yl)amino)-3-methyl-1H-pyrazole-1-yl)-2-methylpropanenitrile;
(104) (4-((4-(ethylamino)-5-(trifluoromethyl)-7H-pyrrolo[2,3-d]pyrimidine-2-yl)amino)-3-methoxyphenyl)(4-morpholinopiperidine-1-yl)methanone;
(105) (44(4-(ethylamino)-5-(trifluoromethyl)-7H-pyrrolo[2,3-d]pyrimidine-2-yl)amino)-3-methoxyphenyl)(morpholino)methanone;
(106) (4-(ethylamino)-5-(trifluoromethyl)-7H-pyrrolo[2,3-d]pyrimidine-2-yl)amino)-3-methoxyphenyl)(4-(4-methylpiperazine-1-yl)piperidine-1-yl)methanone;
(107) (4-((4-(ethylamino)-5-(trifluoromethyl)-7H-pyrrolo[2,3-d]pyrimidine-2-yl)amino)-3-methoxyphenyl)(4-methylpiperazine-1-yl)methanone;
(108) (R)-(4-((4-(ethylamino)-5-(trifluoromethyl)-7H-pyrrolo[2,3-d]pyrimidine-2-yl)amino)-3-methoxyphenyl)(2-methylmorpholino)methanone;
(109) ((2R,6S)-2,6-dimethylmorpholino)((4-((4-(ethylamino)-5-(trifluoromethyl)-7H-pyrrolo[2,3-d]pyrimidine-2-yl)amino)-3-methoxyphenyl)methanone;
(110) (4,4-difluoropiperidine-1-yl)(4-((4-(ethylamino)-5-(trifluoromethyl)-7H-pyrrolo[2,3-d]pyrimidine-2-yl)amino)-3-methoxy phenyl)methanone;
(111) (S)-(4-((4-(ethylamino)-5-(trifluoromethyl)-7H-pyrrolo[2,3-d]pyrimidine-2-yl)amino)-3-methoxyphenyl)(2-methylmorpholino)methanone;
(112) (3-methoxy-4-((4-(methylamino)-5-(trifluoromethyl)-7H-pyrrolo[2,3-d]pyrimidine-2-yl)amino)phenyl)(morpholino)methanone;
(113) 2-(4-((4-(ethylamino)-5-(trifluoromethyl)-7H-pyrrolo[2,3-d]pyrimidine-2-yl)amino)-3-methyl-1H-pyrazole-1-yl)-2-methylpropaneamide;
(114) N4-ethyl-N2-(2-methoxy-4-(4-methylpiperazine-1-yl)phenyl)-5-(trifluoromethyl)-7H-pyrrolo[2,3-d]pyrimidine-2,4-diamine;
(115) N4-ethyl-N2-(2-methoxy-4-morpholinophenyl)-5-(trifluoromethyl)-7H-pyrrolo[2,3-d]pyrimidine-2,4-diamine;

(116) 4-((4-(ethylamino)-5-(trifluoromethyl)-7H-pyrrolo[2,3-d]pyrimidine-2-yl)amino)-2-fluoro-5-methoxy-N-(1-(oxetanepiperidine-4-yl)benzamide;
(117) N2-(5-chloro-1-((3S,4S)-3-fluoro-1-(oxetane-3-yl)piperidine-4-yl)-1H-pyrazole-4-yl)-N4-cyclopropyl-5-(trifluoromethyl)-7H-pyrrolo[2,3-d]pyrimidine-2,4-diamine;
(118) (4-((4-(cyclopropylamino)-5-(trifluoromethyl)-7H-pyrrolo[2,3-d]pyrimidine-2-yl)amino)-3-methoxyphenyl)(morpholino)methanone;
(119) (4-((4-(cyclopropylamino)-5-(trifluoromethyl)-7H-pyrrolo[2,3-d]pyrimidine-2-yl)amino)-3-methoxyphenyl)(4-methylpiperazine-1-yl)methanone;
(120) (4-((4-(cyclopropylamino)-5-(trifluoromethyl)-7H-pyrrolo[2,3-d]pyrimidine-2-yl)amino)-3-methoxyphenyl)(4-(4-methylpiperazine-1-yl)piperidine-1-yl)methanone;
(121) (3-methoxy-4(4(1-methylcyclopropyl)amino)-5-(trifluoromethyl)-7H-pyrrolo[2,3-d]pyrimidine-2-yl)amino)phenyl)(4-methylpiperazine-1-yl)methanone;
(122) (3-methoxy-4(4(1-methylcyclopropyl)amino)-5-(trifluoromethyl)-7H-pyrrolo[2,3-d]pyrimidine-2-yl)amino)phenyl)(4-(4-methylpiperazine-1-yl)piperidine-1-yl)methanol;
(123) (R)-(2,4-dimethylpiperazine-1-yl)(2-fluoro-5-methoxy-4-((4-(methylamino)-5-(trifluoromethyl)-7H-pyrrolo[2,3-d]pyrimidine-2-yl)amino)phenyl)methanone;
(128) 2-((6-chloro-2-methyl-1-oxoisoindol-5-yl)amino)-4-(ethylamino)-7H-pyrrolo[2,3-d]pyrimidine-5-carbonitrile;
(129) 4-(ethylamino)-2-((2-methyl-1-oxoisoindol-5-yl)amino)-7H-pyrrolo[2,3-d]pyrimidine-5-carbonitrile;
(130) 4-(ethylamino)-2-((6-methoxy-2-methyl-1-oxoisoindol-5-yl)amino)-7H-pyrrolo[2,3-d]pyrimidine-5-carbonitrile;
(131) 4-(ethylamino)-2-((6-methoxy-2,2,4-trimethyl-3-oxo-3,4-dihydro-2H-benzo[b][1,4]oxazine-7-yl)amino)-7H-pyrrolo[2,3-d]pyrimidine-5-carbonitrile;
(132) 2-((2-(2-cyanopropane-2-yl)-4-methylthiazole-5-yl)amino)-4-(ethyl amino)-7H-pyrrolo[2,3-d]pyrimidine-5-carbonitrile;
(133) 5-((4-(ethylamino)-5-(trifluoromethyl)-7H-pyrrolo[2,3-d]pyrimidine-2-yl)amino)-6-methoxy-2-methylisoindolin-1-one;
(134) 6-((4-(ethylamino)-5-(trifluoromethyl)-7H-pyrrolo[2,3-d]pyrimidine-2-yl)amino)-5-methoxy-2-methylisoindolin-1-one;
(135) 6-chloro-5-((4-(ethylamino)-5-(trifluoromethyl)-7H-pyrrolo[2,3-d]pyrimidine-2-yl)amino)-2-methylisoindolin-1-one;
(136) 5-((4-(ethylamino)-5-(trifluoromethyl)-7H-pyrrolo[2,3-d]pyrimidine-2-yl)amino)-2-methylisoindolin-1-one; and
(137) 7-((4-(ethylamino)-5-(trifluoromethyl)-7H-pyrrolo[2,3-d]pyrimidine-2-yl)amino)-6-methoxy-2,2,4-trimethyl-2H-benzo[1,4]oxazine-3(4H)-one.

6. A preparation method of the compound represented by formula 1 of claim 1 comprising the following steps, as shown in reaction formula 1 below:
preparing a compound represented by formula 4 by reacting a compound represented by formula 2 with a compound represented by formula 3 (step 1); and
preparing a compound represented by formula 1 by reacting the compound represented by formula 4 prepared in step 1 above in the presence of an acid (step 2):

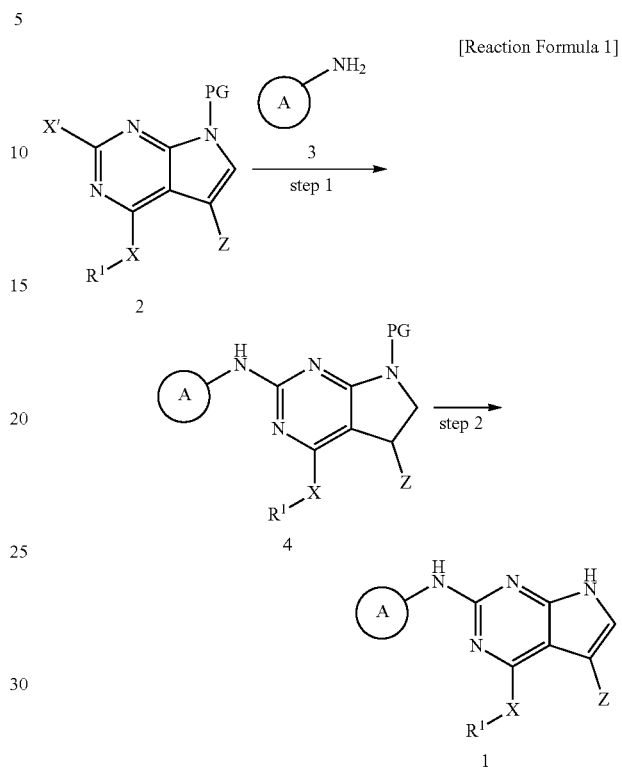

[Reaction Formula 1]

wherein,

X, Z, R$^1$ and are as defined in formula 1 of claim 1;

X' is halogen; and

PG is (2-(trimethylsilyl)methoxy)methyl (SEM), p-methoxybenzyl (PMB), t-butyloxycarbonyl (BOC), carbobenzyloxy (Cbz), 9-fluorenylmethyloxycarbonyl (Fmoc), acetyl (Ac), benzoyl (Bz), benzyl (Bn), 3,4-dimethoxybenzyl (DMPM), p-methoxyphenyl (PMP), tosyl (Ts), 2,2,2-trichloroethoxycarbonyl (Troc), 2-trimethylsilylethoxycarbonyl (Teoc), aryloxycarbonyl (Alloc) or p-methoxybenzyl (PMB).

7. A pharmaceutical composition comprising the compound represented by formula 1 of claim 1, the optical isomer thereof, or the pharmaceutically acceptable salt thereof as an active ingredient for the prevention or treatment of protein kinase related disease.

\* \* \* \* \*